United States Patent
Beiriger et al.

(10) Patent No.: US 8,425,487 B2
(45) Date of Patent: Apr. 23, 2013

(54) DRUG VIAL SPIKES, FLUID LINE SETS, AND RELATED SYSTEMS

(75) Inventors: Michael James Beiriger, Pittsburgh, PA (US); Ryan Kaintz, Allison Park, PA (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 230 days.

(21) Appl. No.: 12/827,207

(22) Filed: Jun. 30, 2010

(65) Prior Publication Data

US 2011/0004145 A1    Jan. 6, 2011

Related U.S. Application Data

(60) Provisional application No. 61/222,146, filed on Jul. 1, 2009.

(51) Int. Cl.
*A61M 5/32* (2006.01)
*A61B 19/00* (2006.01)
*A61M 37/00* (2006.01)
*A61M 31/00* (2006.01)

(52) U.S. Cl.
USPC ............. 604/411; 604/414; 604/403; 604/86; 604/506

(58) Field of Classification Search ............ 604/403, 604/411, 414, 86, 506
See application file for complete search history.

(56) References Cited

U.S. PATENT DOCUMENTS

| | | | |
|---|---|---|---|
| 4,898,578 | A | 2/1990 | Rubalcaba, Jr. |
| 4,915,688 | A | 4/1990 | Bischof et al. |
| 4,925,444 | A | 5/1990 | Orkin et al. |
| 4,943,279 | A | 7/1990 | Samiotes et al. |
| 4,946,439 | A | 8/1990 | Eggers |
| 4,959,050 | A | 9/1990 | Bobo, Jr. |
| 4,966,579 | A | 10/1990 | Polaschegg |
| 4,981,467 | A | 1/1991 | Bobo, Jr. et al. |
| 5,037,390 | A | 8/1991 | Raines et al. |
| 5,041,086 | A | 8/1991 | Koenig et al. |
| 5,047,014 | A | 9/1991 | Mosebach et al. |
| 5,049,129 | A | 9/1991 | Zdeb et al. |
| 5,053,019 | A | 10/1991 | Duffy |
| 5,057,076 | A | 10/1991 | Polaschegg |
| 5,074,756 | A | 12/1991 | Davis |
| 5,078,683 | A | 1/1992 | Sancoff et al. |
| 5,102,392 | A | 4/1992 | Sakai et al. |
| 5,127,618 | A | 7/1992 | Pagé et al. |

(Continued)

FOREIGN PATENT DOCUMENTS

| | | |
|---|---|---|
| EP | 0426273 | 5/1991 |
| EP | 0532432 | 9/1991 |

(Continued)

OTHER PUBLICATIONS

International Search Report and Written Opinion, Application No. PCT/US2010/040547; mailed Oct. 29, 2010; pp. 1-12.

*Primary Examiner* — Jacqueline Stephens
*Assistant Examiner* — Andrew J Mensh
(74) *Attorney, Agent, or Firm* — Fish & Richardson P.C.

(57) ABSTRACT

This disclosure relates to drug vial spikes, fluid line sets, and related systems. In some aspects, a fluid line set includes a frame, multiple spikes extending from the frame, and multiple fluid lines connected to the frame. The frame is configured to hold the fluid lines in a spaced apart configuration.

20 Claims, 28 Drawing Sheets

U.S. PATENT DOCUMENTS

| | | | |
|---|---|---|---|
| 5,176,631 A | 1/1993 | Koenig | |
| 5,193,990 A | 3/1993 | Kamen et al. | |
| 5,207,642 A | 5/1993 | Orkin et al. | |
| 5,211,201 A | 5/1993 | Kamen et al. | |
| 5,213,483 A | 5/1993 | Flaherty et al. | |
| 5,246,347 A | 9/1993 | Davis | |
| 5,252,044 A | 10/1993 | Raines et al. | |
| 5,256,157 A | 10/1993 | Samiotes et al. | |
| 5,304,126 A | 4/1994 | Epstein et al. | |
| 5,304,165 A | 4/1994 | Haber et al. | |
| 5,317,506 A | 5/1994 | Coutré et al. | |
| 5,324,258 A * | 6/1994 | Rohrbough | 604/86 |
| 5,329,976 A | 7/1994 | Haber et al. | |
| 5,378,231 A | 1/1995 | Johnson et al. | |
| 5,382,232 A | 1/1995 | Hague et al. | |
| 5,392,638 A | 2/1995 | Kawahara | |
| 5,401,237 A | 3/1995 | Tachibana et al. | |
| 5,421,812 A | 6/1995 | Langley et al. | |
| 5,431,626 A | 7/1995 | Bryant et al. | |
| 5,431,627 A | 7/1995 | Pastrone et al. | |
| 5,438,510 A | 8/1995 | Bryant et al. | |
| 5,445,621 A | 8/1995 | Poli et al. | |
| 5,464,392 A | 11/1995 | Epstein et al. | |
| 5,494,822 A | 2/1996 | Sadri | |
| 5,496,273 A | 3/1996 | Pastrone et al. | |
| 5,531,697 A | 7/1996 | Olsen et al. | |
| 5,531,698 A | 7/1996 | Olsen | |
| 5,533,389 A | 7/1996 | Kamen et al. | |
| 5,547,470 A | 8/1996 | Johnson et al. | |
| 5,573,502 A | 11/1996 | LeCocq et al. | |
| 5,575,310 A | 11/1996 | Kamen et al. | |
| 5,578,223 A | 11/1996 | Bene et al. | |
| 5,609,575 A | 3/1997 | Larson et al. | |
| 5,616,124 A | 4/1997 | Hague et al. | |
| 5,641,892 A | 6/1997 | Larkins et al. | |
| 5,643,218 A | 7/1997 | Lynn et al. | |
| 5,651,775 A | 7/1997 | Walker et al. | |
| 5,698,090 A | 12/1997 | Bene et al. | |
| 5,713,865 A | 2/1998 | Manning et al. | |
| 5,743,886 A | 4/1998 | Lynn et al. | |
| 5,745,378 A | 4/1998 | Barker et al. | |
| 5,752,931 A | 5/1998 | Nazarian et al. | |
| 5,755,563 A | 5/1998 | Clegg et al. | |
| 5,785,701 A * | 7/1998 | Sams et al. | 604/411 |
| 5,800,387 A | 9/1998 | Duffy et al. | |
| 5,816,779 A | 10/1998 | Lawless et al. | |
| 5,843,035 A | 12/1998 | Bowman et al. | |
| 5,873,872 A | 2/1999 | Thibault et al. | |
| 5,897,526 A | 4/1999 | Vaillancourt | |
| 5,916,197 A | 6/1999 | Reilly et al. | |
| 5,925,011 A | 7/1999 | Faict et al. | |
| 5,935,099 A | 8/1999 | Peterson et al. | |
| 5,935,105 A | 8/1999 | Manning et al. | |
| 5,938,636 A | 8/1999 | Kramer et al. | |
| 5,941,848 A | 8/1999 | Nishimoto et al. | |
| 5,989,423 A | 11/1999 | Kamen et al. | |
| 6,017,318 A | 1/2000 | Gauthier et al. | |
| 6,019,750 A * | 2/2000 | Fowles et al. | 604/403 |
| 6,041,801 A | 3/2000 | Gray et al. | |
| 6,065,941 A | 5/2000 | Gray et al. | |
| 6,068,612 A | 5/2000 | Bowman et al. | |
| 6,070,761 A | 6/2000 | Bloom et al. | |
| 6,077,246 A | 6/2000 | Kullas et al. | |
| 6,099,492 A | 8/2000 | Le Boeuf | |
| 6,110,153 A | 8/2000 | Davis et al. | |
| 6,117,103 A | 9/2000 | Tverskoy et al. | |
| 6,123,686 A | 9/2000 | Olsen et al. | |
| 6,142,008 A | 11/2000 | Cole et al. | |
| 6,210,361 B1 | 4/2001 | Kamen et al. | |
| 6,241,704 B1 | 6/2001 | Peterson et al. | |
| 6,269,340 B1 | 7/2001 | Ford et al. | |
| 6,302,653 B1 | 10/2001 | Bryant et al. | |
| 6,321,941 B1 * | 11/2001 | Argentieri et al. | 222/81 |
| 6,464,667 B1 | 10/2002 | Kamen et al. | |
| 6,468,242 B1 | 10/2002 | Wilson et al. | |
| 6,471,872 B2 | 10/2002 | Kitaevich et al. | |
| 6,475,180 B2 | 11/2002 | Peterson et al. | |
| 6,489,896 B1 | 12/2002 | Platt et al. | |
| 6,527,758 B2 | 3/2003 | Ko | |
| 6,575,930 B1 | 6/2003 | Trombley, III et al. | |
| 6,604,908 B1 | 8/2003 | Bryant et al. | |
| 6,610,024 B1 | 8/2003 | Benatti | |
| 6,616,633 B1 | 9/2003 | Butterfield et al. | |
| 6,622,542 B2 | 9/2003 | Derek et al. | |
| 6,692,478 B1 | 2/2004 | Paradis | |
| 6,695,803 B1 | 2/2004 | Robinson et al. | |
| 6,699,230 B2 | 3/2004 | Jaafar et al. | |
| 6,726,656 B2 | 4/2004 | Kamen et al. | |
| 6,731,971 B2 | 5/2004 | Evans, III et al. | |
| 6,736,972 B1 | 5/2004 | Matson | |
| 6,780,322 B1 | 8/2004 | Bissler et al. | |
| 6,802,892 B2 | 10/2004 | Newman et al. | |
| 6,877,713 B1 | 4/2005 | Gray et al. | |
| 6,985,870 B2 | 1/2006 | Martucci et al. | |
| 7,029,456 B2 | 4/2006 | Ware et al. | |
| 7,060,049 B2 | 6/2006 | Trombley, III et al. | |
| 7,092,796 B2 | 8/2006 | Vanderveen | |
| 7,128,105 B2 | 10/2006 | Tribble et al. | |
| 7,150,735 B2 | 12/2006 | Hickle | |
| 7,204,823 B2 | 4/2007 | Estes et al. | |
| 7,214,210 B2 | 5/2007 | Kamen et al. | |
| 7,326,186 B2 | 2/2008 | Trombley, III et al. | |
| 7,338,470 B2 | 3/2008 | Katz et al. | |
| 7,347,849 B2 | 3/2008 | Brugger et al. | |
| 7,427,281 B2 | 9/2008 | Uber, III | |
| 7,517,332 B2 | 4/2009 | Tonelli et al. | |
| 7,559,524 B2 | 7/2009 | Gray et al. | |
| 7,575,567 B2 | 8/2009 | Simpkins | |
| 7,628,184 B2 | 12/2009 | Py et al. | |
| 7,632,078 B2 | 12/2009 | Demers et al. | |
| 7,641,626 B2 | 1/2010 | Tonelli et al. | |
| 7,654,976 B2 | 2/2010 | Peterson et al. | |
| 7,662,139 B2 | 2/2010 | Demers et al. | |
| 7,668,731 B2 | 2/2010 | Martucci et al. | |
| 7,699,806 B2 | 4/2010 | Ware et al. | |
| 7,762,989 B2 | 7/2010 | Simpson | |
| 7,766,873 B2 | 8/2010 | Moberg et al. | |
| 7,837,647 B2 | 11/2010 | Estes et al. | |
| 7,837,651 B2 | 11/2010 | Bishop et al. | |
| 7,905,861 B2 | 3/2011 | Rhinehart et al. | |
| 7,922,708 B2 | 4/2011 | Estes et al. | |
| 7,967,783 B2 | 6/2011 | Rebours | |
| 7,967,785 B2 | 6/2011 | Morgan et al. | |
| 7,981,101 B2 | 7/2011 | Walsh | |
| 7,981,280 B2 | 7/2011 | Carr et al. | |
| 7,985,198 B2 | 7/2011 | Von Blumenthal et al. | |
| 7,998,115 B2 | 8/2011 | Bedingfield | |
| 2002/0045571 A1 | 4/2002 | Liu et al. | |
| 2003/0191445 A1 | 10/2003 | Wallen et al. | |
| 2005/0085760 A1 | 4/2005 | Ware et al. | |
| 2005/0203329 A1 | 9/2005 | Muto et al. | |
| 2005/0209563 A1 | 9/2005 | Hopping et al. | |
| 2005/0230292 A1 | 10/2005 | Beden et al. | |
| 2006/0025747 A1 | 2/2006 | Sullivan et al. | |
| 2006/0084905 A1 | 4/2006 | Montgomery et al. | |
| 2006/0089594 A1 * | 4/2006 | Landau | 604/68 |
| 2006/0229557 A1 | 10/2006 | Fathallah et al. | |
| 2007/0156089 A1 | 7/2007 | Yu | |
| 2008/0242915 A1 | 10/2008 | Jackson et al. | |
| 2008/0300570 A1 | 12/2008 | Fowles et al. | |
| 2008/0311007 A1 | 12/2008 | Helmerson | |
| 2009/0036864 A1 | 2/2009 | Moy et al. | |
| 2009/0057258 A1 | 3/2009 | Tornqvist | |
| 2009/0069783 A1 | 3/2009 | Ellstrom et al. | |
| 2009/0204066 A1 | 8/2009 | Radmer et al. | |
| 2010/0004602 A1 | 1/2010 | Nord et al. | |
| 2010/0030048 A1 | 2/2010 | Heller et al. | |
| 2010/0042048 A1 | 2/2010 | Christensen | |
| 2010/0084041 A1 | 4/2010 | Fehr et al. | |
| 2010/0113891 A1 | 5/2010 | Barrett et al. | |
| 2011/0004143 A1 | 1/2011 | Beiriger et al. | |
| 2011/0004144 A1 | 1/2011 | Beiriger et al. | |
| 2011/0004145 A1 | 1/2011 | Beiriger | |
| 2011/0004187 A1 | 1/2011 | Beiriger | |
| 2011/0054397 A1 | 3/2011 | Menot et al. | |
| 2011/0077614 A1 | 3/2011 | Shay | |
| 2011/0094619 A1 | 4/2011 | Steel et al. | |

| | | | |
|---|---|---|---|
| 2011/0118662 A1 | 5/2011 | Mhatre et al. | |
| 2011/0125085 A1 | 5/2011 | McGill et al. | |
| 2011/0152770 A1 | 6/2011 | DiPerna et al. | |
| 2011/0160701 A1 | 6/2011 | Wyatt et al. | |
| 2011/0172603 A1 | 7/2011 | Yodfat et al. | |
| 2011/0190702 A1 | 8/2011 | Stumber | |
| 2011/0190703 A1 | 8/2011 | Pratt et al. | |

FOREIGN PATENT DOCUMENTS

| | | |
|---|---|---|
| EP | 1978256 | 10/2008 |
| GB | 1978256 | 11/1982 |
| WO | WO 96/40322 | 12/1996 |
| WO | WO9910027 A1 | 3/1999 |
| WO | WO 2007101798 A2 * | 9/2007 |
| WO | WO 2008/008845 | 1/2008 |
| WO | WO2008064046 A2 | 5/2008 |
| WO | WO2009044221 A1 | 4/2009 |
| WO | WO 2010/099816 | 9/2010 |
| WO | WO 2010/100074 | 9/2010 |
| WO | WO 2011/054693 | 5/2011 |
| WO | WO 2011/092068 | 8/2011 |

* cited by examiner

DRUG VIAL SPIKES, FLUID LINE SETS, AND RELATED SYSTEMS

CROSS-REFERENCE TO RELATED APPLICATIONS

This application claims the benefit of U.S. Provisional Application Ser. No. 61/222,146, filed on Jul. 1, 2009, which is incorporated by reference herein.

TECHNICAL FIELD

This invention relates to drug vial spikes, fluid line sets, and related systems.

BACKGROUND

As soon as kidney failure is diagnosed, patients are typically given medication to help control the symptoms and slow the progress of the damage to the kidneys. Patients with chronic kidney failure generally take drugs to control the balance of minerals in the body and prevent a reduction of red blood cells (anemia).

Healthy kidneys produce the hormone erythropoietin (often shortened to "EPO"), which stimulates the production of red blood cells in the bone marrow. Red blood cells play a key role in the delivery of oxygen to tissues in the body. If the body does not have enough EPO, it can lead to anemia. This often causes a drop in physical and mental performance and an increased risk for cardio-vascular diseases. To prevent anemia, chronic renal patients normally receive a synthetic version of erythropoietin (also referred to as "EPO") that, like the natural erythropoietin, stimulates the production of red blood cells.

Anemia can be managed using a variety of different drugs. For example, since iron is also needed to produce red blood cells, many dialysis patients also take iron preparations. Venofer® (iron sucrose injection, USP) is indicated in the treatment of iron deficiency anemia in patients undergoing chronic hemodialysis who are receiving supplemental EPO therapy.

SUMMARY

In one aspect of the invention, a drug delivery device includes a drug vial holder including an upper member and a lower member. The upper and lower members are configured to receive a drug vial therebetween. The drug delivery device also includes a mechanism configured to move at least one of the upper and lower members relative to the other of the upper and lower members such that, when a drug vial is disposed between the upper and lower members and the at least one of the upper and lower members is moved toward the other, the drug vial is compressed between the upper and lower members.

In another aspect of the invention, a drug delivery system includes a drug delivery device including a drug vial holder having an upper member and a lower member, and a mechanism connected to the drug vial holder. The drug delivery system also includes a drug vial disposed between the upper and lower members of the drug vial holder. The mechanism is configured to move at least one of the upper and lower members relative to the other of the upper and lower members in a manner to compress the drug vial therebetween.

In an additional aspect of the invention, a dialysis system includes a dialysis machine that includes a blood pump. The system further includes a drug delivery device that includes a drug pump, a drug vial holder including an upper member and a lower member, and a mechanism configured to move at least one of the upper and lower members relative to the other of the upper and lower members such that, when a drug vial is disposed between the upper and lower members and the at least one of the upper and lower members is moved toward the other, the drug vial is compressed between the upper and lower members. The system also includes a blood line set including a blood line that is operably connected to the blood pump and a fluid line set including a fluid line that is operably connected to the drug pump and is connected to a spike. The fluid line set is configured such that the spike can be placed in fluid communication with the drug vial retained between the upper and lower members of the drug vial holder by moving the drug vial holder and the drug vial relative to the spike. The fluid line is in fluid communication with the blood line set such that a drug can be delivered from the drug vial to the blood line set when the drug pump is operated.

In a further aspect of the invention, a drug vial spiking device includes a cup-shaped member having a base and a sidewall that at least partially form a recess configured to receive at least a portion of a drug vial, a spike extending from a central region of the base, and multiple springs extending from the base of the cup-shaped member into the recess. The spike defines a channel extending therethrough, and the springs are configured to apply a force to a drug vial in a direction away from the base of the cup-shaped member when at least a portion of the drug vial is positioned in the recess.

In another aspect of the invention, a fluid line set includes multiple fluid lines and multiple drug vial spiking devices, each of which is connected to one of the fluid lines. Each of the drug vial spiking devices includes a cup-shaped member having a base and a sidewall that at least partially form a recess configured to receive at least a portion of a drug vial, a spike extending from a central region of the base, and multiple springs extending from the base of the cup-shaped member into the recess. The spike defines a channel extending therethrough, and the springs are configured to apply a force to a drug vial in a direction away from the base of the cup-shaped member when at least a portion of the drug vial is positioned in the recess.

In an additional aspect of the invention, a fluid line set includes a frame having a top member, a manifold, and at least one connecting member that extends between and is attached to the top member and the manifold. The manifold defines a fluid passage extending therethrough. The fluid line set also includes multiple spikes that extend from the top member and multiple fluid lines connected to the top member and the manifold. Each of the spikes defines a fluid channel. Each of the fluid lines is in fluid communication with the channel of one of the spikes and with the fluid passage extending through the manifold. The frame is configured to hold the fluid lines in a spaced apart configuration.

In a further aspect of the invention, a drug delivery system includes a drug delivery device having a surface from which multiple pumps extend and a fluid line set. The fluid line set includes a frame having a top member, a manifold, and at least one connecting member that extends between and is attached to the top member and the manifold. The manifold defines a fluid passage extending therethrough. The fluid line set also includes multiple spikes that extend from the top member and multiple fluid lines connected to the top member and the manifold. Each of the spikes defines a fluid channel. Each of the fluid lines is in fluid communication with the channel of one of the spikes and with the fluid passage extending through the manifold. The frame is configured to hold the fluid lines in a spaced apart configuration, and the fluid line set is configured to be secured to the drug delivery device in a manner such that each of the fluid lines is operably connected to one of the pumps.

In yet another aspect of the invention, a dialysis system includes a dialysis machine including a blood pump and a blood line set including a blood line that is operably connected to the blood pump. The system further includes a drug delivery device having a surface from which multiple drug pumps extend and a fluid line set. The fluid line set includes a frame having a top member, a manifold, and at least one connecting member that extends between and is attached to the top member and the manifold. The manifold defines a fluid passage extending therethrough. The fluid line set also includes multiple spikes that extend from the top member and multiple fluid lines connected to the top member and the manifold. Each of the spikes defines a fluid channel. Each of the fluid lines is in fluid communication with the channel of one of the spikes and with the fluid passage extending through the manifold. The frame is configured to hold the fluid lines in a spaced apart configuration. The fluid line set is configured to be secured to the drug delivery device in a manner such that each of the fluid lines is operably connected to one of the pumps. The fluid line set is further configured to be placed in fluid communication with the blood line set such that, when one of the spikes of the fluid line set is disposed within a drug vial and the drug pump operably connected to the fluid line that is in fluid communication with the channel of that spike is operated, a drug is delivered from the drug vial to the blood line set via the fluid line set.

In a further aspect of the invention, a drug vial spiking assembly includes a drug vial spike device including a spike extending from a base and a cover secured to the drug vial spike device. The spike has a tip opposite the base, and the cover is movable toward the base from a first position in which the cover at least partially covers the tip of the spike to a second position in which the tip of the spike is fully exposed.

In an additional aspect of the invention, a fluid line set includes multiple fluid lines, multiple drug vial spike devices, and multiple covers. Each of the drug vial spike devices is connected to one of the fluid lines and includes a spike extending from a base. The spike of each drug vial spike device has a tip opposite the base. Each of the covers is secured to one the drug vial spike devices and is movable toward the base from a first position in which the cover at least partially covers the tip of the spike of the spike device to which the cover is secured to a second position in which the tip of the spike of the spike device to which the cover is secured is fully exposed.

In another aspect of the invention, a drug delivery device includes a pump extending from a surface of the drug delivery device and a door having an inner surface and including a spring-loaded member exposed along the inner surface. The spring-loaded member defines a recess configured to receive a portion of the pump when the door is closed. When a fluid line is positioned in the recess and the door is closed, the fluid line is compressed between the spring-loaded member and the pump in a manner such that the fluid line is occluded in at least one location.

In a further aspect of the invention, a drug delivery system includes multiple fluid lines and multiple occluders. Each occluder is operably connected to one of the fluid lines. The system also includes a single pump operably connected to a drug delivery line that is in fluid communication with each of the fluid lines. The drug delivery system is configured to operate the occluders and the pump in a manner such that, when the fluid lines are placed in fluid communication with multiple drug vials, drugs are drawn from the multiple drug vials into the drug delivery line.

In a further aspect of the invention, a dialysis system includes a dialysis machine including a blood pump, a modular drug delivery device including at least one drug pump and a plurality of drug vial holders, and a housing to which the blood pump and the modular drug delivery device are secured. A blood line set including multiple blood lines and a vented chamber in fluid communication with the multiple blood lines is connected to the blood pump in a manner such that, when the blood line set is connected to a patient and the blood pump is operated, blood of the patient is passed through the blood line set. A drug line set including multiple drug lines is connected to the vented chamber of the blood line set and to the at least one drug pump in a manner such that, when the drug line set is fluidly connected to one or more drug vials contained in the multiple drug vial holders and the at least one drug pump is operated, drug is delivered from the one or more drug vials to the vented chamber of the blood line set via the drug line set. The dialysis system also includes a control unit configured to operate the blood pump and the drug pump to simultaneously delivery drug and blood to the vented chamber.

In an additional aspect of the invention, a method includes inserting a spike through a seal of a drug vial to allow fluid communication between an interior of the drug vial and a channel defined by the spike, and deforming a portion of the seal away from a body of the drug vial to facilitate removal of drug from the interior of the drug vial. Deforming the portion of the seal away from the body of the drug vial is carried out by using a mechanism to move the spike relative to the drug vial.

In yet another aspect of the invention, a method includes compressing a seal of a drug vial between a cap of the drug vial and a neck portion or body portion of the drug vial by disposing the drug vial between an upper member and a lower member of a drug vial holder and moving at least one of the upper and lower members of the drug vial holder toward the other of the upper and lower members of the drug vial holder. While maintaining the seal in a compressed state, a spike is inserted through the seal of the drug vial to allow fluid communication between an interior of the drug vial and a channel defined by the spike.

In a further aspect of the invention, a drug delivery method includes passing a first drug through a drug delivery line to a vented chamber, passing a gas bubble through the drug delivery line to the vented chamber, and then passing a second drug through the drug delivery line to the vented chamber. The gas bubble extends across substantially an entire inner diameter of the drug delivery line as the gas bubble passes therethrough.

In another aspect of the invention, a drug delivery method includes determining that a first drug contained in a first container connected to a drug delivery line and a second drug contained in a second container connected to the drug delivery line are not suitable for mixing together prior to being delivered to a patient, and after determining that the first and second drugs are not suitable for mixing, operating a drug delivery device in a manner to deliver the first drug through the drug delivery line and to a patient, deliver a gas bubble through the drug delivery line; and then deliver the second drug through the drug delivery line and to a patient.

In an additional aspect of the invention, a method includes selecting a drug vial combination by comparing a prescribed drug dosage to a dosing schedule. The dosing schedule provides multiple drug vial combinations associated with multiple drug dosages. The selected drug vial combination includes one or more drug vials, and each of the one or more drug vials contains a first drug. The method further includes delivering substantially all of the first drug from each of the one or more drug vials to a patient by operating a pump of a drug delivery device to which the one or more drug vials are connected.

In a further aspect of the invention, a method includes receiving by one or more computers data related to a prescribed drug dosage, and determining by the one or more computers one or more recommended drug vial combinations by comparing the prescribed dosage to a dosing schedule. Each of the one or more recommended drug vial combinations includes one or more drug vials, and the one or more drug vials of each of the one or more recommended drug vial combinations contain an amount of drug substantially equal to the prescribed dosage. The dosing schedule includes data representing a plurality of drug vial combinations associated with a plurality of drug dosages.

In another aspect of the invention, a computer program product resides on a computer readable medium, and the computer program product includes instructions for causing a processor to determine one or more recommended drug vial combinations by comparing a prescribed dosage to a dosing schedule. Each of the one or more recommended drug vial combinations includes one or more drug vials, and the one or more drug vials of each of the one or more recommended drug vial combinations contain an amount of drug substantially equal to the prescribed dosage. The dosing schedule includes data representing multiple different drug vial combinations associated with multiple different drug dosages.

In another aspect of the invention, a method includes fully evacuating and delivering a drug from its vial to a patient in an automated fashion.

In an additional aspect of the invention, a drug delivery device is configured to fully evacuate a drug from its vial and deliver the drug to a patient in an automated fashion.

In a further aspect of the invention, a method includes developing or calculating a dosing schedule that provides guidance to the prescriber and/or administrator regarding the correct average dose to be administered using permutations of multiple vials of a drug per treatment, and/or over multiple treatments.

In another aspect of the invention, a device is configured to calculate a dosing schedule that provides guidance to the prescriber and/or administrator regarding the correct average dose to be administered using permutations of multiple vials of a drug per treatment, and/or over multiple treatments.

In an additional aspect of the invention, a method includes automatically delivering several different drugs in succession using one pumping device, and without allowing the drugs to mix prior to delivery to the patient.

In a further aspect of the invention, a drug delivery device is configured to automatically deliver several different drugs in succession using one pumping device, and without allowing the drugs to mix prior to delivery to the patient.

Implementations can include one or more of the following features.

In certain implementations, the mechanism is configured to compress a seal disposed between a cap of the drug vial and a neck portion of the drug vial when the drug vial is disposed between the upper and lower members and the at least one of the upper and lower members is moved toward the other.

In some implementations, multiple projections extend from a surface of the lower member. The projections are configured to dent adjacent portions of a cap of the drug vial into a seal of the drug vial when the drug vial is compressed between the upper and lower members.

In certain implementations, the projections are configured to pierce the adjacent portions of the cap of the drug vial when the drug vial is compressed between the upper and lower members.

In some implementations, the lower member defines an opening sized to receive a drug vial spike, and the opening is arranged to align with a seal of the drug vial when the drug vial is disposed between the upper and lower members.

In certain implementations, the lower member defines a recess configured to receive a portion of the drug vial therein.

In some implementations, the mechanism is configured to move the upper member, the lower member, and the drug vial disposed therebetween in unison after compressing the drug vial between the upper and lower members.

In certain implementations, the mechanism includes a motor that, when operated, causes the at least one of the upper and lower members to move toward the other.

In some implementations, the mechanism is configured in a manner such that, after operating the motor for a period of time to compress the drug vial between the upper and lower members, continued operation of the motor causes the upper and lower members to move in unison.

In certain implementations, the mechanism is configured to move the upper member of the drug vial holder toward the lower member of the drug vial holder.

In some implementations, the mechanism includes a rotatable, threaded drive shaft to which a threaded drive member is secured, and the drive member is configured such that rotation of the drive shaft causes the drive member to move axially along the drive shaft.

In certain implementations, the drive member includes a ball screw.

In some implementations, the drive member is secured to the upper member of the vial holder in a manner such that axial movement of the drive member causes axial movement of the upper member.

In certain implementations, the drive member is secured to a cross bar that is attached to at least one extension member, and the at least one extension member is attached to the upper member of the drug vial holder.

In some implementations, the mechanism includes at least one resilient member configured to resist downward movement of the lower member of the drug vial holder.

In certain implementations, the at least one resilient member includes a spring.

In some implementations, the at least one resilient member is configured to provide sufficient resistance to downward movement of the lower member to cause a seal of a drug vial disposed between the upper and lower members to be compressed when the at least one of the upper and lower members is moved toward the other.

In certain implementations, the at least one resilient member is configured to collapse and allow the drug vial to move in unison with the upper and lower members after the seal of the drug vial has been compressed.

In some implementations, the drug delivery device further includes at least one spike disposed beneath the drug vial holder, and the mechanism is configured to move the upper and lower members of the drug vial holder in unison relative to the spike to cause the spike to penetrate a drug vial disposed between the upper and lower members.

In certain implementations, the drug delivery device further includes a pump configured to be operably connected to a fluid line that is in fluid communication with a drug vial disposed between the upper and lower members of the drug vial holder such that operation of the pump can draw drug from the drug vial and through the fluid line.

In some implementations, the mechanism is manually operable.

In certain implementations, the springs are leaf springs.

In some implementations, at least one of the leaf springs includes a projection extending from a surface thereof, and the projection is arranged to contact a cap of the drug vial when the drug vial is inserted into the recess.

In certain implementations, the projection and the at least one leaf spring are configured in a manner such that the projection dents a cap of the drug vial when the drug vial is inserted into the recess.

In some implementations, the base defines multiple openings configured to receive the multiple springs when the drug vial is fully inserted into the recess.

In certain implementations, at least one of the springs includes a projection extending therefrom, and the at least one of the springs and the projection are configured such that the projection dents a cap of the drug vial when the drug vial is inserted into the recess with sufficient force to cause the cap of the vial to contact the base of the cup-shaped member.

In some implementations, the drug vial spiking device further includes at least one bi-stable member attached to the base, and the bi-stable member is positioned above an aperture defined in the base.

In certain implementations, the bi-stable member is configured to be stably positioned in a first position and a second position, and at least a portion of the bi-stable member is visible to a user when the bi-stable member is in the second position.

In some implementations, the bi-stable member in the second position indicates that a drug vial has been fully inserted into the recess.

In certain implementations, the portion of the member visible to the user protrudes from an outer surface of the base.

In some implementations, the bi-stable member includes a projection extending from its upper surface.

In certain implementations, the projection is configured to push the bi-stable member from the first position to the second position when the drug vial is fully inserted into the recess such that the vial contacts the base of the cup-shaped member.

In some implementations, the spike includes a portion configured to engage an inner surface of a seal of a drug vial after the spike is inserted into the drug vial.

In certain implementations, the portion of the spike extends laterally in at least one direction to a greater extent than a remainder of the spike.

In some implementations, the portion of the spike is substantially conical.

In certain implementations, the portion of the spike includes a barb.

In some implementations, the spike defines multiple openings along an outer surface of the spike, and each of the openings is in fluid communication with the channel.

In certain implementations, a portion of the sidewall forms a flange that retains the portion of the vial within the recess.

In some implementations, the flange is configured to contact a cap of the vial.

In certain implementations, the frame includes two connecting members that extend between and are attached to the top member and the manifold.

In some implementations, the frame is rectangular.

In certain implementations, the frame further includes a cross bar that extends between and is connected to the two connecting members.

In some implementations, the cross bar defines multiple spaced apart recesses, and each of the recesses is configured to retain one of the fluid lines.

In certain implementations, a projection extends from a surface of the frame, and the projection is configured to mate with a matching hole in a drug delivery device.

In some implementations, the projection is configured to engage the matching hole in the drug delivery device in a manner to releasably secure the fluid line set to the drug delivery device.

In certain implementations, the projection and the matching hole are hexagonal.

In some implementations, each of the top member, the manifold, and the at least one connecting member has a greater rigidity than the fluid lines.

In certain implementations, the fluid line set further includes a cover disposed over at least one of the spikes.

In some implementations, the drug delivery device includes a door, and the door and the surface of the drug delivery device form a cassette compartment configured to receive the frame and the fluid lines of the fluid line set therein when the door is closed.

In certain implementations, an inner surface of the door defines a recessed region configured to receive the frame of the fluid line set.

In some implementations, an inner surface of the door defines a hole configured to receive a projection that extends from a surface of the support frame.

In certain implementations, the hole and the projection are configured to engage one another in a manner to releasably secure the fluid line set to the door of the drug delivery device.

In some implementations, the pumps are peristaltic pumps.

In certain implementations, the drug delivery device further includes multiple air bubble detectors positioned on the surface, and the fluid line set is configured to be disposed adjacent the surface of the dialysis machine in a manner such that each fluid line is aligned with one of the air bubble detectors.

In some implementations, the drug delivery device further includes a drug vial holder that is movable in a manner such that, when a drug vial is disposed in the drug vial holder, the drug vial can be moved with respect to the fluid line set to cause one of the spikes of the fluid line set to penetrate the vial.

In certain implementations, the cover is resilient such that when a force applied to the cover to move the cover from the first position to the second position is removed, the cover returns to approximately the first position.

In some implementations, a length of the cover is greater than a length of the spike when the cover is in the first position, and the length of the cover is less than the length of the spike when the cover is in the second position.

In certain implementations, the cover includes an upper member, a lower member, and at least one elongate structure connecting the upper member to the lower member.

In some implementations, each of the upper and lower members defines an aperture configured to receive the spike therein.

In certain implementations, the at least one elongate structure includes multiple circumferentially spaced, resilient columns.

In some implementations, each of the resilient columns defines a channel along its peripheral surface that facilitates collapse of the column when a force is applied to the column along a longitudinal axis of the column.

In certain implementations, the at least one elongate structure includes a foam tube.

In some implementations, the elongate structure includes a spring.

In certain implementations, the spring is a coil spring that at least partially surrounds the spike.

In some implementations, the member is an inflated member.

In certain implementations, the inflated member is an inflated balloon.

In some implementations, the inflated member at least partially surrounds the spike.

In certain implementations, the inflated member and the spike are configured such that the spike punctures the inflated member when a force is applied to the inflated member in a direction along the spike.

In some implementations, the cover is a coil spring that at least partially surrounds the spike.

In certain implementations, the cover includes an elongate tubular member that fits over the spike.

In some implementations, the drug vial spiking assembly further includes a structure that is fixed relative to the spike and is configured to contact the elongate tubular member and resist further movement of the elongate tubular member when the elongate tubular member has been moved to the second position.

In certain implementations, multiple projections extend from a surface of the cover, and the projections are configured to dent adjacent portions of a cap of a drug vial into a rubber seal of the drug vial when the drug vial is pressed against the cover with sufficient force to cause the cover to move from the first position to the second position.

In some implementations, the pump is configured to pump fluid through the fluid line when the pump is operated, the fluid line is positioned in the recess, the door is closed, and the pump is operated.

In certain implementations, a first spring is connected to a first end region of the spring-loaded member, and a second spring is connected to a second end region of the spring loaded member, and the first and second springs are each secured to a structure of the door.

In some implementations, the pump is rigidly fixed to a housing of the drug delivery device.

In certain implementations, the pump is a peristaltic pump comprising a frame and multiple rollers positioned about a circumference of the frame.

In some implementations, the frame is rotatably secured to a rod that is fixed to a housing of the drug delivery device.

In certain implementations, the drug delivery device further includes a drive mechanism configured to operate the peristaltic pump.

In some implementations, the drive mechanism includes a motor having an output shaft and a worm gear attached to the output shaft, and the worm gear is engaged with a gear secured to the frame such that rotation of the output shaft causes the frame of the peristaltic pump to rotate.

In certain implementations, the drug delivery device includes multiple pumps extending from the surface of the drug delivery device, the door includes multiple spring-loaded members exposed along the inner surface, and each of the spring-loaded members defines a recess configured to receive a portion of one of the pumps when the door is closed.

In some implementations, the inner surface of the door defines a recessed region configured to receive a frame of a fluid line set therein.

In certain implementations, the inner surface of the door further defines multiple recessed channels configured to receive fluid lines of the fluid line set therein.

In some implementations, the drug delivery device further includes multiple air bubble detectors, and each of the air bubble detectors is arranged to substantially align with a fluid line when fluid lines are positioned within the recesses of the door and the door is closed such that the air bubble detectors can detect air within the fluid lines.

In certain implementations, the drug delivery device further includes multiple drug vial holders positioned above the multiple pumps, and each of the drug vial holders is configured to retain at least one drug vial.

In some implementations, the drug delivery device is configured to operate the pumps in a manner such that, when fluid lines are positioned in the recesses of the door, the door is closed, and each of the fluid lines is in fluid communication with a drug vial retained by one of the drug vial holders, an air bubble is passed through a drug delivery line connected to each of the fluid lines between the delivery of drug from consecutive vials.

In certain implementations, the drug delivery device is configured to operate the pumps in a manner to pass an air bubble through the drug delivery line after completion of the delivery of drug from each vial.

In some implementations, the drug delivery device is part of a dialysis machine.

In certain implementations, the fluid line is connected to a blood circuit of the dialysis machine in a manner such that fluid is delivered through the fluid line to the blood circuit when the pump is operated.

In some implementations, the drug delivery system is configured to operate the occluders and the pump in a manner such that drug is only drawn into the drug delivery line from one of the drug vials at a time.

In certain implementations, the drug delivery system further includes multiple air bubble detectors, and each of the air bubble detectors is substantially aligned with one of the fluid lines such that the air bubble detectors can detect air within the fluid lines.

In some implementations, the drug delivery system is configured to operate the occluders and the pump in a manner such that, when the multiple fluid lines are placed in fluid communication with multiple drug vials, an air bubble is passed through the drug delivery line between the delivery of drug from consecutive vials.

In certain implementations, the drug delivery system is configured to operate the occluders and the pump in a manner to pass an air bubble through the drug delivery line after completion of the delivery of drug from each vial.

In some implementations, the drug delivery system is part of a dialysis machine.

In certain implementations, the drug delivery line is connected to a blood circuit of the dialysis machine in a manner such that fluid can be delivered through the drug delivery line to the blood circuit when the pump is operated.

In some implementations, the seal is a rubber seal.

In certain implementations, deforming the portion of the seal includes using the spike to apply a force to the portion of the seal.

In some implementations, the force is a frictional force.

In certain implementations, moving the spike relative to the vial includes applying a force to the body of the drug vial in a direction opposite the force applied to the portion of the seal.

In some implementations, the method further includes maintaining the seal in a compressed state while inserting the spike through the seal.

the seal is compressed between a cap of the drug vial and a neck portion of the drug vial.

In certain implementations, the seal is compressed between a cap of the drug vial and a body portion of the drug vial.

In some implementations, the mechanism includes a spring.

In certain implementations, the mechanism is an automated mechanism.

In some implementations, the seal is compressed between a cap of the drug vial and a neck portion of the drug vial.

In certain implementations, the seal is a rubber seal.

In some implementations, the method further includes denting portions of the cap into the seal.

In certain implementations, denting the portions of the cap into the seal includes forcing the cap against projections extending from a surface of the lower member of the drug vial holder.

In some implementations, denting the portions of the cap into the seal includes piercing portions of the cap.

In certain implementations, the method further includes deforming a portion of the seal away from a body of the drug vial to facilitate removal of drug from the drug vial.

In some implementations, deforming the portion of the seal includes using the spike to apply a force to the portion of the seal.

In certain implementations, the force is a frictional force.

In some implementations, the method of claim further includes applying a force to the body portion of the drug vial in a direction opposite the force applied to the portion of the seal.

In certain implementations, the method further includes applying a force to the neck portion of the drug vial in a direction opposite the force applied to the portion of the seal.

In some implementations, the first and second drugs are the same drug.

In certain implementations, the first and second drugs are different drugs.

In some implementations, the first and second drugs are not suitable for mixing together prior to being delivered to a patient.

In certain implementations, the first drug is synthetic erythropoietin and the second drug is iron sucrose.

In some implementations, the gas bubble pushes some of the first drug through the drug delivery line to the vented chamber as the gas bubble is passed through the drug delivery line to the vented chamber.

In certain implementations, the gas bubble pushes substantially all residual first drug in the drug delivery line to the vented chamber as the gas bubble is passed through the drug delivery line to the vented chamber.

In some implementations, passing the first drug through the drug delivery line includes operating a first pump that is operably connected to a first fluid line to move the first drug into the drug delivery line from the first fluid line, and passing the second drug through the drug delivery line includes operating a second pump that is operably connected to a second fluid line to move the second drug into the drug delivery line from the second fluid line.

In certain implementations, passing the gas bubble through the drug delivery line includes operating the first pump to move the gas bubble into the drug delivery line from the first fluid line.

In some implementations, passing the first drug, the gas bubble, and the second drug through the drug delivery line includes operating a single pump that is operably connected to the drug delivery line.

In certain implementations, the first drug is drawn into the drug delivery line from a first fluid line, and the second drug is drawn into the drug delivery line from a second fluid line.

In some implementations, the drug delivery method further includes occluding the second fluid line while the first drug is being drawn into the drug delivery line, and occluding the first fluid line while the second drug is being drawn into the drug delivery line.

In certain implementations, the gas bubble is drawn into the drug delivery line from the first fluid line.

In some implementations, the first drug is moved into the drug delivery line from a first drug container that is connected to the drug delivery line via a first fluid line, and the second drug is moved into the drug delivery line from a second drug container that is connected to the drug delivery line via a second fluid line.

In certain implementations, passing the gas bubble through the drug delivery line includes moving gas into the drug delivery line from the first drug container.

In some implementations, the drug delivery method further includes detecting gas in the first fluid line and occluding a region of the first fluid line when a desired volume of gas has passed beyond the region of the fluid line.

In certain implementations, the drug delivery method further includes allowing the gas bubble to escape to atmosphere via a vent of the vented chamber.

In some implementations, the drug deliver method further includes introducing blood into the vented chamber.

In certain implementations, the drug delivery method further includes allowing the first drug to mix with the blood in the vented chamber, and then delivering the resulting mixture of the first drug and the blood to a patient.

In some implementations, the gas bubble is an air bubble.

In certain implementations, the drug delivery method further includes passing a third drug through the drug delivery line to the vented chamber.

In some implementations, the drug delivery method further includes passing a gas bubble through the drug delivery line after passing the second drug through the drug delivery line and before passing the third drug through the drug delivery line.

In certain implementations, the drug delivery method further includes venting the gas bubble to atmosphere before the second drug is delivered to the patient such that the gas bubble is not delivered to the patient.

In some implementations, a control unit of the drug delivery device selects the drug vial combination.

In certain implementations, the control unit runs a computer program that automatically selects the drug vial combination based on the prescribed dosage and operator preferences.

In some implementations, the prescribed dosage and operator preferences are entered into the drug delivery device by the operator.

In certain implementations, the prescribed dosage is electronically transmitted to the control unit from a database storing data comprising the prescribed dosage.

In some implementations, the prescribed dosage is entered into the database by or at the direction of a physician of the patient.

In certain implementations, the control unit controls operation of the pump.

In some implementations, the drug vial combinations and associated drug dosages of the dosing schedule are based on a single treatment.

In certain implementations, the drug vial combinations and associated drug dosages of the dosing schedule are based on multiple treatments.

In some implementations, the drug vial combination is selected based at least in part on the number of drug vials required over the course one or more treatments.

In certain implementations, the drug vial combination is selected based at least in part on the number of drug vials required over the course of multiple treatments.

In some implementations, the drug vial combination is selected based in part on a drug dosage consistency that would be provided by the drug vial combination over the course of multiple treatments.

In certain implementations, the method further includes displaying the one or more recommended drug vial combinations on a display.

In some implementations, determining the one or more recommended drug vial combinations includes determining the one or more drug vial combinations from the dosing schedule that utilize the fewest drug vials over the course of one or more treatments and that contain an amount of drug substantially equal to the prescribed drug dosage.

In certain implementations, determining the one or more recommended drug vial combinations further includes determining the one or more drug vial combinations from the dosing schedule that utilize the fewest drug vials over the course of multiple treatments and that contain an amount of drug substantially equal to the prescribed drug dosage.

In some implementations, determining the one or more recommended drug vial combinations includes determining one or more drug vial combinations from the dosing schedule that result in a drug dosage consistency within an acceptable consistency range over the course of one or more treatments and that contain an amount of drug substantially equal to the prescribed drug dosage.

In certain implementations, determining the one or more recommended drug vial combinations further includes determining the one of the one or more drug vial combinations that utilizes the fewest number of drug vials over the course of the one or more treatments and that contains an amount of drug substantially equal to the prescribed drug dosage.

In some implementations, determining the one or more recommended drug vial combinations includes determining one or more drug vial combinations from the dosing schedule that result in a drug dosage consistency within an acceptable consistency range over the course of multiple treatments and that contain an amount of drug substantially equal to the prescribed drug dosage.

In certain implementations, determining the one or more recommended drug vial combinations further includes determining the one of the one or more drug vial combinations from the dosing schedule that utilizes the fewest number of drug vials over the course of the multiple treatments and that contains an amount of drug substantially equal to the prescribed drug dosage.

In some implementations, determining the one or more recommended drug vial combinations includes determining the drug vial combination from the dosing schedule that provides the greatest drug dosage consistency over the course of the one or more treatments and that contains an amount of drug substantially equal to the prescribed drug dosage.

In certain implementations, determining the one or more recommended drug vial combinations includes determining the drug vial combination that provides the greatest drug dosage consistency over the course of multiple treatments and that contains an amount of drug substantially equal to the prescribed drug dosage.

In some implementations, the data is transmitted from a user interface of a medical system.

In certain implementations, the medical system is a hemodialysis system.

In some implementations, the one or more computers is a processor.

Implementations can include one or more of the following advantages.

In some implementations, drug delivery systems and methods permit the drug to be fully evacuated from the vial. Fully evacuating the drug from the vial helps to ensure that substantially all of the drug is delivered to the patient. This reduces the amount of drug that is unused and wasted relative to many conventional drug delivery techniques. In addition, ensuring that substantially all of the drug is removed from the vial increases the accuracy with which drug prescribed drug dosages are delivered to the patients.

In certain implementations, the drug delivery systems and methods allow the seal (e.g., rubber seal or stopper) of the vial to be compressed between the body or neck portion and the cap of the vial to reduce (e.g., prevent) movement of the seal relative to the body or neck portion and the cap of the vial. Limiting the movement of the seal relative to the body and cap of the vial can help to ensure that the seal does not bulge inwardly into the vial as the spike penetrates the seal. This can help to ensure that the drug is fully evacuated from the vial.

In some implementations, the spike is retracted slightly relative to the vial (e.g., by moving the vial away from the spike, by moving the spike away from the vial, or both) after the spike has penetrated the seal. Retracting the spike relative to the vial can cause the portion of the seal surrounding the spike to be deformed outwardly away from the vial, which can help to ensure that the drug is fully evacuated from the vial.

In certain implementations, the drug delivery system includes a mechanism that, during operation, compresses the seal of the vial between the body and cap of the vial and then causes the spike to penetrate the seal. As explained above, compressing the seal helps to ensure that the seal does not bulge inwardly into the vial as the spike penetrates the seal. Providing a single mechanism that can both compress the seal and cause the spike to penetrate the seal can increase the speed and efficiency of the set up and delivery processes associated with the drug delivery system.

In some implementations, the fluid lines connected to the various spikes are retained by a structure (e.g., a frame) that holds the fluid lines in a spaced apart configuration. This arrangement can make it easier for the user to load the fluid lines onto corresponding instruments of the drug delivery device, such as air bubble detectors, occluders, and/or pumps.

In certain implementations the spikes are provided with one or more covers that cover the spikes before they are inserted into the vials. This can help to prevent contamination of the spikes due to inadvertent contact with the spikes prior to their insertion into the vials. In certain implementations, the covers are configured to automatically expand over the spikes when the spikes are removed from the vials. This can help to prevent the operator from pricking himself or herself with the spikes when removing the spikes from the vials and disposing of the spikes.

In some implementations, the drug delivery systems and methods permit multiple different drugs or other therapeutic agents to be delivered in succession without substantial mixing of the drugs or therapeutic agents. By delivering several different drugs or therapeutic agents in succession to the patient without allowing the drugs or therapeutic agents to mix prior to delivery to the patient, adverse patient reactions resulting from the mixing of incompatible drugs or therapeutic agents prior to delivery can be avoided.

In certain implementations, the user is provided with a dosing schedule of the proper combination of vials per treatment, which also helps to reduce (e.g., minimize) the amount of drug that is wasted. Single use drug vials can be used for only one patient and then must generally be discarded. If the combination of vials selected for a treatment contain a greater amount of drug than is prescribed for the particular patient being treated, then some of the drug will not be administered to the patient and must be discarded. The dosing schedule can prevent this from happening by informing the user of all combinations of vials that can be used based on the patient's prescription without wasting any of the drug.

In addition, the dosing schedule can inform the user of the vial combinations that result in the fewest number of vials used per treatment, per week, and/or per month. This allows the user to select vial combinations that reduce (e.g., minimize) the number of vials used and thus reduce (e.g., minimize) the number of vials and the amount of corresponding packaging materials that must be discarded over a given period of time.

The dosing schedule can also inform the user of the dosage consistency that the patient receives throughout a treatment or throughout multiple treatments with different vial combinations. This allows the user to select a vial combination that provides a desired dosage consistency.

Other aspects, features, and advantages will be apparent from the description and drawings, and from the claims.

DETAILED DESCRIPTION

Figure 1:
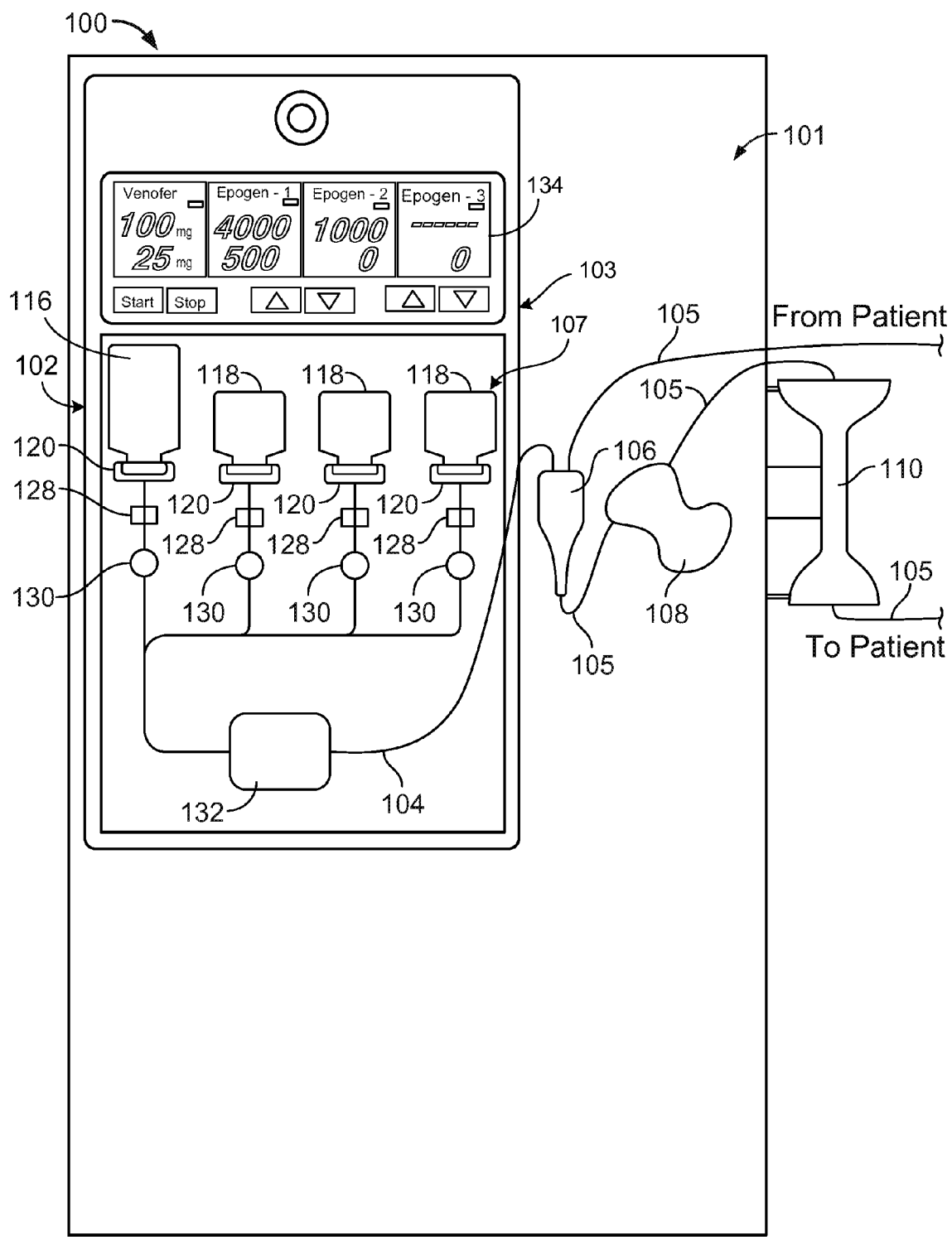
FIG. 1 is a schematic of a hemodialysis machine that includes a modular drug delivery device. A drug administration fluid line set and multiple drug vials are secured to the modular drug delivery device.

Referring to FIG. 1, a hemodialysis system 100 includes a hemodialysis machine 101 that has a drug delivery system 102. The drug delivery system 102 includes a modular drug delivery device 103 and a disposable drug administration fluid line set 107 that is connected to the drug delivery device 103. A drug delivery line 104 of the drug administration fluid line set 107 is fluidly connected to a blood circuit of the hemodialysis system 100. The blood circuit of the hemodialysis system 100 includes, among other things, a series of blood lines 105, a drip chamber 106, and a dialyzer 110. A blood pump (e.g., a peristaltic pump) 108 is configured to pump blood through the blood circuit during treatment. The hemodialysis system 100 also includes a dialysate circuit and various other components that, for the sake of simplicity, are not described in detail. During hemodialysis treatment, blood is drawn from the patient and, after passing through the drip chamber 106, is pumped through the dialyzer 110 where toxins are removed from the blood and collected in dialysate passing through the dialyzer. The cleansed blood is then returned to the patient, and the dialysate including the toxins (referred to as "spent dialysate") is disposed of or recycled and reused. As discussed in greater detail below, during the hemodialysis treatment, drugs (e.g., Epogen® and Venofer®) are also delivered to the drip chamber 106 using the drug delivery system 102. The drugs mix with the patient's blood within the drip chamber 106 and are then delivered to the patient along with the patient's blood.

Figure 2:
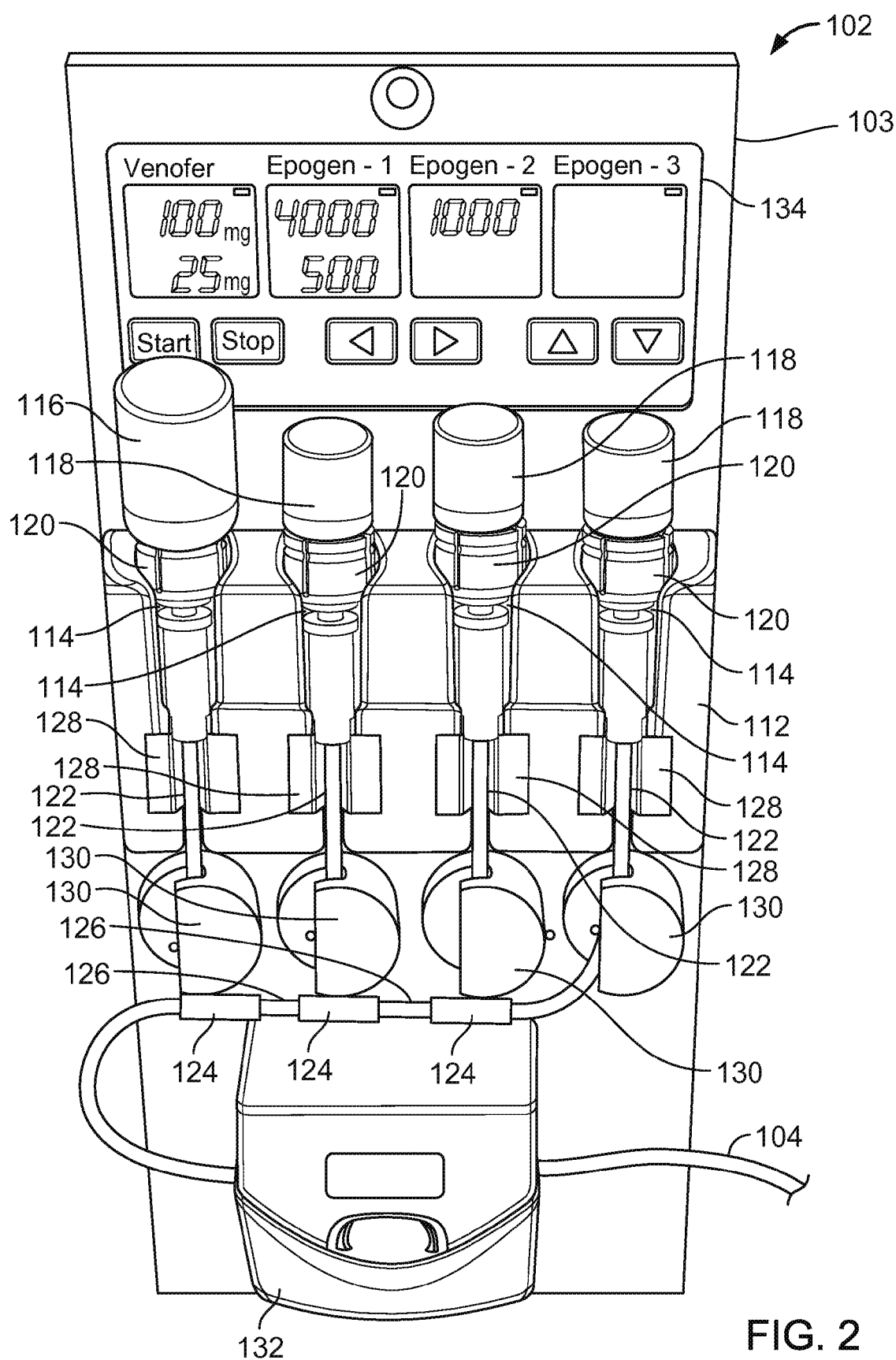
FIG. 2 is a perspective view of the modular drug delivery device of the hemodialysis machine of FIG. 1 and the drug administration fluid line set and drug vials that are secured to the modular drug delivery device.

As shown in FIG. 2, the modular drug delivery device 103 includes a drug vial holder 112 that defines four channels 114. Each of the channels 114 is designed to hold captive a drug vial 116, 118. The channels 114 can, for example, be recesses that are formed within the drug vial holder 112 and that are sized and shaped to receive only the caps and narrow neck portions of the vials 116, 118 such that the larger body portions of the vials sit above the holder 112. In the illustrated implementation, the vial 116 furthest to the left contains Venofer® and the three vials 118 to the right of the Venofer® vial 116 contain Epogen®. Venofer® (iron sucrose injection, USP) is a sterile, aqueous complex of polynuclear iron (III)-hydroxide in sucrose that is manufactured by American Regent, Inc. Venofer® is indicated in the treatment of iron deficiency anemia in patients undergoing chronic hemodialysis who are receiving supplemental erythropoietin therapy. Epogen® is a drug that stimulates the production of red blood cells and is also commonly used in dialysis patients. Epogen® is manufactured by Amgen, Inc.

The disposable drug administration fluid line set 107 is fluidly connected to each of the vials 116, 118. The drug administration fluid line set 107 includes four drug vial spikes 120 that connect to the vials 116, 118 in a manner to allow the drugs within the vials (i.e., the Venofer® and Epogen®) to flow into feeder lines 122 via the drug vial spikes 120. Each of the feeder lines 122 is attached to a T-connector 124. The T-connectors 124 and associated tubing segments 126 connect the feeder lines 124 to the drug delivery line 104. The drug vial spikes 120 can be formed of one or more relatively rigid medical grade plastics, such as polycarbonate or alpha-methylstyrene (AMS), and the various fluid lines can be formed of a more flexible medical grade plastic, such as polyvinylchloride (PVC).

Each of the feeder lines 122, as shown in FIG. 2, passes through (e.g., is threaded through) a bubble detector 128. The bubble detectors 128 are capable of detecting air bubbles within the feeder lines 122. As a result, each of the bubble detectors 128 can determine whether its associated drug vial 116, 118 is empty during treatment, because air is drawn from the vial 116, 118 into the feeder line 122 when the vial is empty. In some implementations, the bubble detectors 122 are optical detectors. The OPB 350 bubble detector made by Optek can, for example, be used. Other types of optical detectors can alternatively or additionally be used. Similarly, other types of sensors, such as sensors utilizing ultrasound technology can be used as the bubble detectors. Examples of such sensors include the AD8/AD9 Integral Ultrasonic Air-In-Line, Air Bubble Detector and the BD8/BD9 Integral Ultrasonic Air Bubble, Air-In-Line & Liquid Level Detection Sensors (manufactured by Introtek International (Edgewood, N.Y.)). In some implementations, the bubble detector 128 includes a sensor that, in addition to sensing the presence of an air bubble within its associated feeder line 122, can sense the presence of the feeder line itself.

Downstream of the bubble detectors 128, the feeder lines 122 pass through (e.g., are threaded through) occluders 130. Each of the occluders 130 can be used to crimp the portion of the feeder line 122 disposed therein to prevent fluid from passing through the feeder line 122. In some implementations, the occluders 130 are solenoid based rams. Alternatively or additionally, other types of automated occluders can be used. The occluders 130 can be collectively operated in a manner such that only one feeder line 122 is unclamped at any particular time.

The drug delivery line 104 to which each of the feeder lines 122 is fluidly connected passes through (e.g., is threaded through) a peristaltic drug pump 132. The drug pump 132 includes multiple rollers that compress the drug delivery line 104 in a manner to create a "pillow" of fluid (i.e., a "pillow" of air or liquid) that is pinched between two points of the drug delivery line 104 that are compressed by the pump rollers. The rollers are arranged around a circumference of a rotatable frame. As the frame is rotated, the rollers force the "pillow" of fluid through the drug delivery line 104 toward the drip chamber 106 (shown in FIG. 1). When the pump 132 is being operated and one of the occluders 130 is open (i.e., not clamping its associated feeder line 122), vacuum pressure is applied to the drug vial 116, 118 that is connected to the feeder line 122 associated with the open occluder 130. In certain cases, the initial pressure in the drug vial 116, 118 is equal to the ambient pressure and when all of the drug has been delivered, the ending pressure within the vial is about −10 psi. In other words, the pressure within the drug vial 116, 118 progresses from ambient to −10 psi as the drug is delivered. The pump 132 is configured to generate a vacuum pressure within the drug delivery line 104 and feeder line 122 that exceeds the competing vacuum within the drug vial 116, 118. As a result, the drug is drawn from the vial 116, 118, through the drug vial spike 120, through the feeder line 122, and into the drug delivery line 104.

In some implementations, each channel 114 of the drug vial holder 112 includes a sensor to sense the presence of a vial or drug container. In certain implementations, each drug channel 114 includes a system which identifies the drug vial installed. The drug vial identification system can, for example, include a bar code reader that reads bar codes on the vials. Different types of sensors can alternatively or additionally be used. In some implementations, for example, the vial identification system uses RFID technology. Other examples of suitable sensors include color sensors for sensing the color of color coded drug vials and/or for sensing the color of the drug within the vial, photo sensors (e.g., cameras) that are equipped with text recognition software to read text on the drug vial, capacitive sensors that permit different size vials to be detected, load cells or scales that detect the mass of the vial, and conductivity or electrical impedance sensors that can be used to determine the type of drug within the vial.

The drug delivery device 103 also includes a control unit (e.g., a microprocessor) that can power the various components of the drug delivery device 103. The control unit can receive signals from and send signals to the various components of the drug delivery device 103, including, but not limited to, the bubble detectors 128, the occluders 130, the drug pump 132, the drug vial ID sensors, and other sensors along the drug lines. The control unit can control the various components of the drug delivery device 103 based on information received from these components. For example, the control unit can control the occluders 130 to ensure that only one of the occluders 130 is open at a time. This helps to ensure that drug is pulled from only one of the vials 116, 118 at a time during treatment. The control unit can also determine the volume of drug delivered based on operation data of the drug pump 132 and can control the occluders 130 based on the drug volume determined to have been delivered. For example, upon determining that the prescribed volume of the drug has been delivered, the control unit can close the occluder 130 associated with that drug vial 116, 118 and open the occluder 130 associated with the next drug to be delivered.

The control unit can also control the timing with which the various occluders 130 are opened and closed. For example, after the full contents of a vial have been evacuated, air will be sucked into the feeder line 122 associated with that vial. As the air passes through the feeder line 122, the bubble detector 128 will detect the air and transmit a signal to the control unit indicating that the vial is empty. In response, the control unit can close the occluder 130 associated with the empty vial and open the occluder 130 associated with the vial containing the next drug to be delivered. Upon receiving information from the bubble detectors 128 indicating that all of the vials have been emptied, the control unit can turn off the drug pump 132.

The control unit can also control certain components of the drug delivery device 103 based on signals received from the drug vial ID sensors, which indicate the presence of a vial and/or the identity of the vial contents. Such an arrangement can help to ensure that the correct vials (e.g., the correct number of vials and the vials containing the correct contents) are used for the treatment. Upon receiving signals from the drug vial ID sensors that do not match the inputted treatment information, for example, an alarm (e.g., an audible and/or visual alarm) can be activated. Alternatively or additionally, the drug delivery device 103 can be configured so that treatment cannot be initiated until the sensors detect the correct combination of vials.

The drug delivery device 103 (e.g., the control unit of the drug delivery device 103) is configured to sense if the blood pump 108 of the dialysis machine 101 is running and to pause drug delivery if the blood pump 108 is stopped. This technique prevents 'pooling' of the delivered drug in the drip chamber 106 during treatment.

Still referring to FIG. 2, the drug delivery device 103 further includes a user interface 134 that is connected to the control unit. The user interface 134 includes right/left arrow keys that allow the user to navigate through displays associated with the vials 116, 118. The user interface 134 also includes up/down arrow keys that enable the user to set the desired dosage for each of the vials 116, 118. In addition, the user interface 134 includes start and stop keys that allow the user to start and stop the drug delivery device 103.

Any of various other types of user interfaces can alternatively or additionally be used. In some implementations, the drug delivery device includes a user interface that allows the user to select a drug to infuse from a menu. In certain implementations, the user may confirm that the drug identified by the drug vial ID sensor is correct and/or make appropriate adjustments. The user interface can be used to input and/or monitor various different treatment parameters. Examples of such parameters include drug dosage, drug delivery rate, amount of drug delivered, status of the drug delivery for each drug channel, time, percent complete, percent remaining, time remaining, time delivered, date, patient ID, patient name, alarms, alerts, etc. Such user interfaces can include a color graphical display. In certain implementations, for example, the user interface is color coded according to drug, dosing, or status of drug delivery (e.g., done, running, ready, etc.).

The drug delivery device 103 also includes an alarm and/or alert system to which the control unit of the drug delivery device 103 is connected. The alarm and/or alert system can be configured to emit a visual and/or audio alarm and/or alert. The alarm and/or alert system can further include pre-programmed alarm and/or alert limitations so that when a user modifies any aspect of the system to be outside of the limitations, or the machine itself detects any aspects of the system to be outside of the limitations, the module emits an alarm and/or alert.

Figure 3:
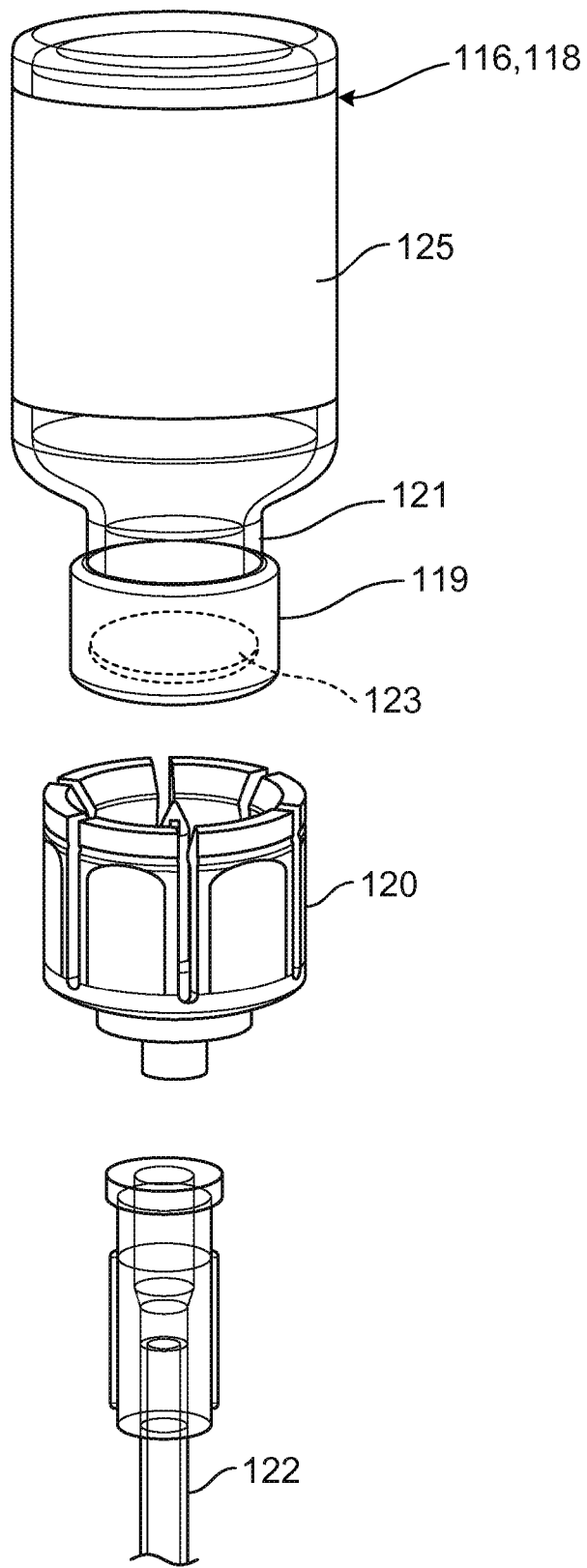
FIG. 3 is an exploded view of a drug vial, a drug vial spike, and a fluid line. The fluid line and drug vial spike are components of the drug administration fluid line set that is used with the modular drug delivery device of the hemodialysis machine of FIG. 1 to deliver a drug from the drug vial to a blood circuit of the hemodialysis machine.

FIG. 3 shows one of the vials 116, 118 and its associated drug vial spike 120 and feeder line 122 in a disconnected state. As shown, the drug vial 116, 118 includes a cap (also referred to as a sleeve) 119 secured to a neck portion 121 of the vial. A rubber seal 123 is positioned between the cap 119 and the neck portion 121. A body portion 125 of the vial is integrally connected to the neck portion 121. Typically, each of the feeder lines 122 and the drug vial spikes 120 includes mating luer lock connectors that permit the feeder lines 122 to be easily connected to and disconnected from the drug vial spikes 120. Alternatively, the feeder lines 122 can be permanently attached to the drug vial spikes 120. The feeder lines 122 can, for example, be welded or adhesively bonded to the drug vial spikes 120.

Figure 4:
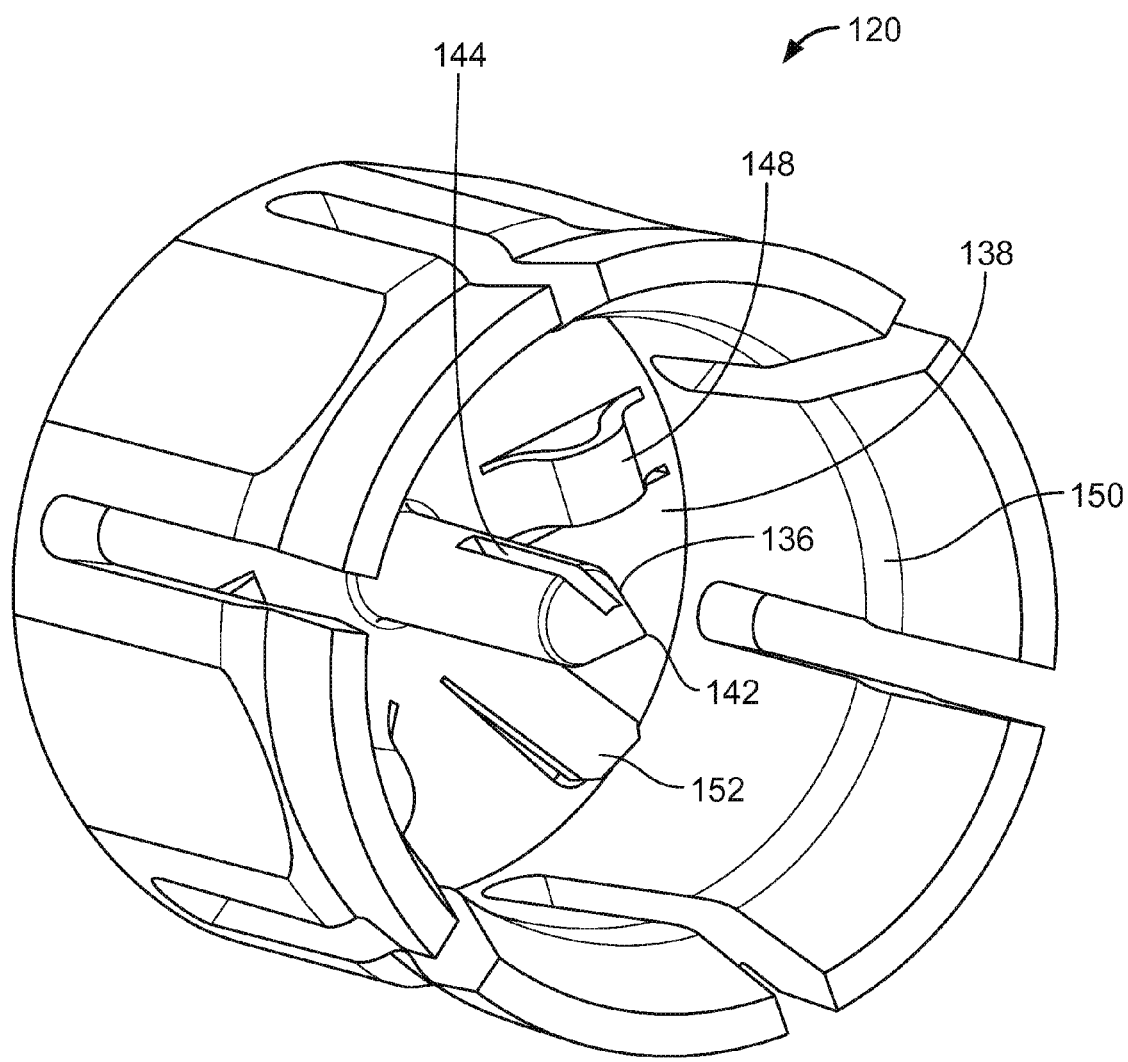
FIGS. 4 and 5 are perspective and top views, respectively, of the drug vial spike shown in FIG. 3.
Figure 5:
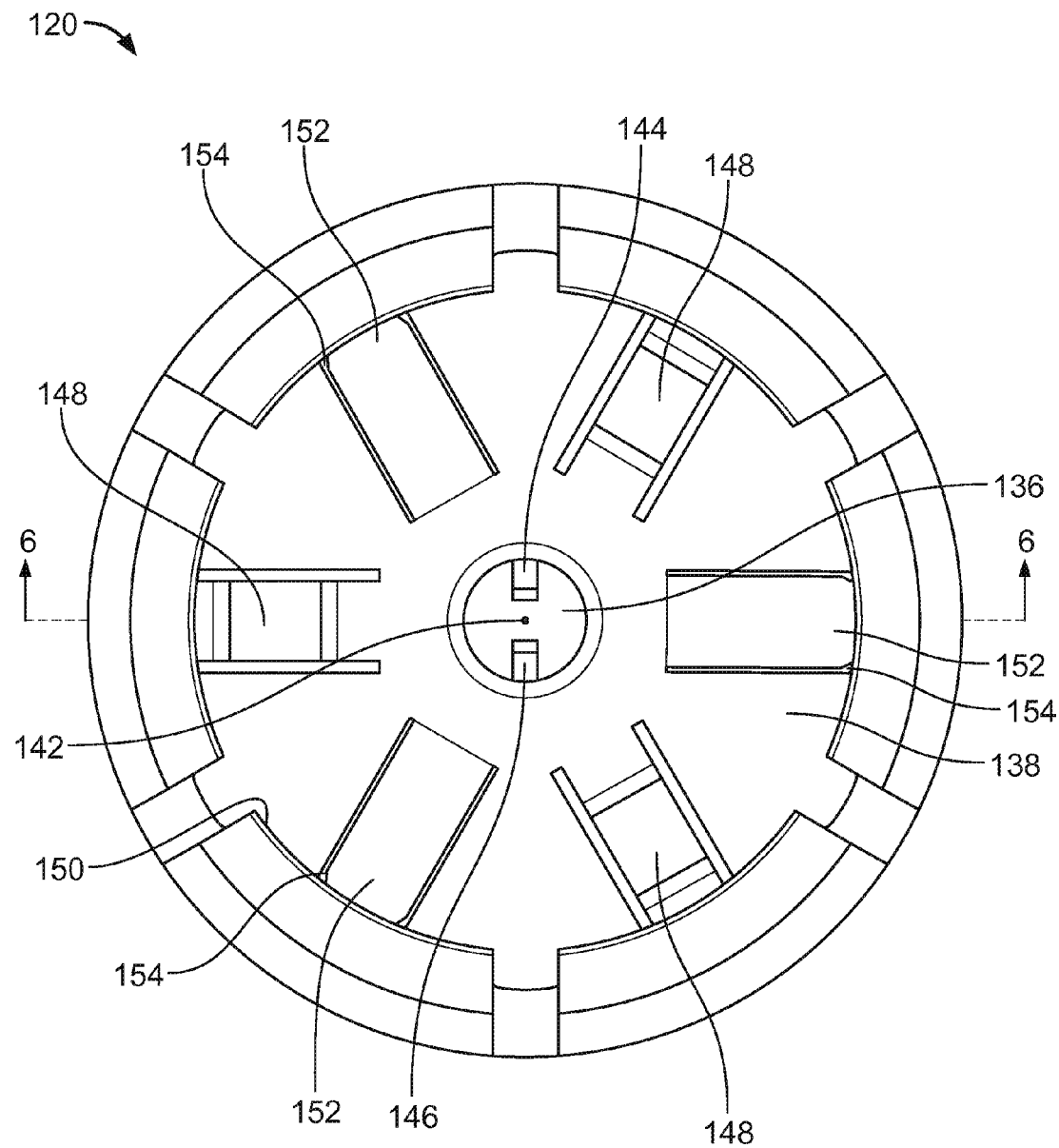
Figure 6:
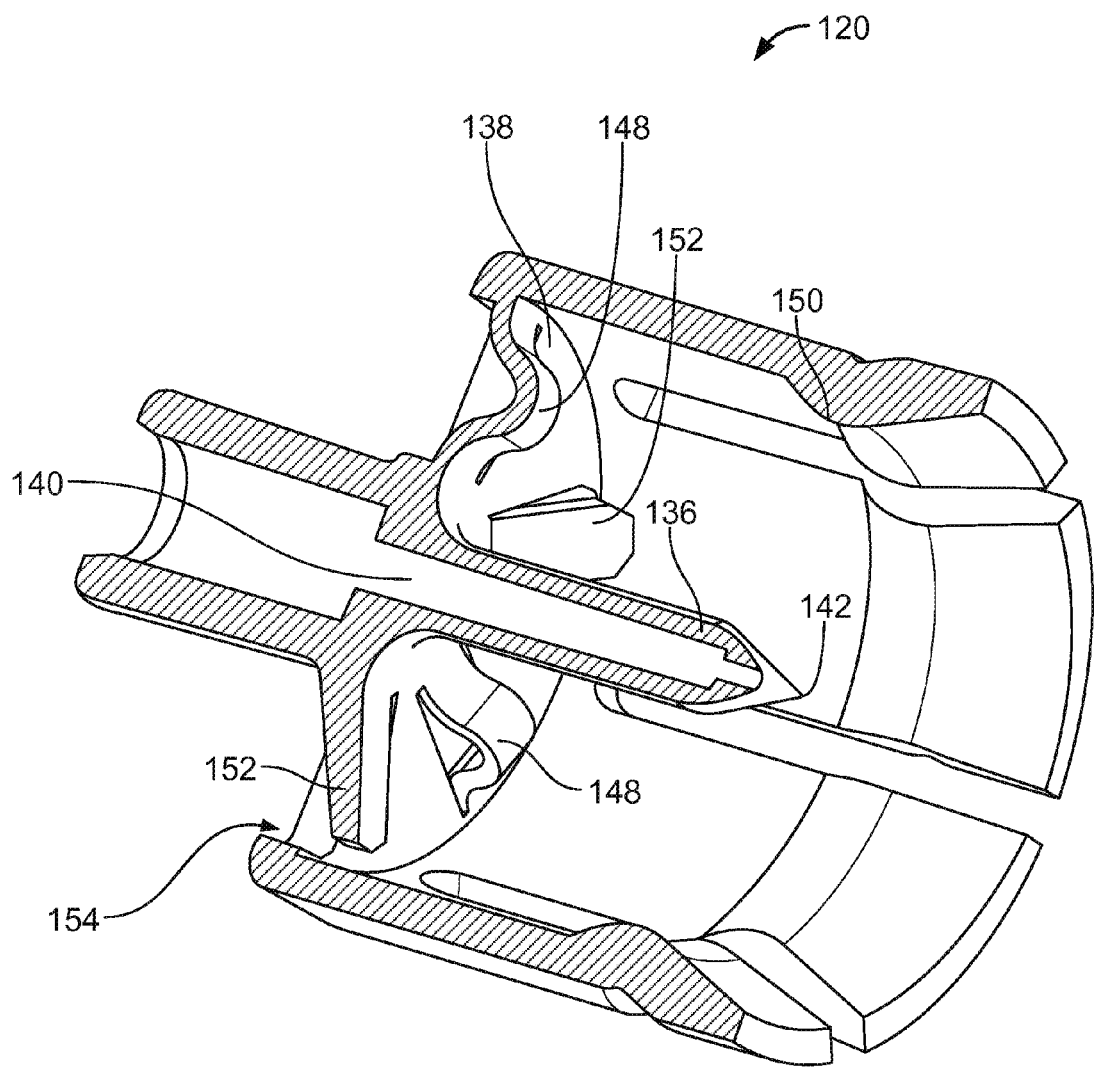
FIG. 6 is a cross-sectional view of the drug vial spike of FIG. 5, taken along line 6-6 in FIG. 5.

Each of the drug vial spikes 120 is configured to grasp and releasably retain the cap 119 of its associated drug vial 116, 118. As shown in FIGS. 4-6, the drug vial spike 120 is a cup-shaped member with a central spike 136 extending from a central region of a base 138 of the cup-shaped member. The central spike 136 includes a relatively sharp tip 142 and forms a channel 140 (shown in FIG. 6) that extends along the length of the central spike 136. During use, the central spike 136 is inserted into its associated drug vial 116, 118 by piercing the rubber seal 123 of the drug vial 116, 118. The user can, for example, grasp the drug vial 116, 118 and press it downward onto the drug vial spike 120 in order to cause the central spike 136 to pierce the rubber seal 123 of the vial 116, 118. The channel 140 of the central spike 136 allows the contents of the drug vial 116, 118 to flow out of the drug vial 116, 118 via the central spike 136. An outer surface of the central spike 136 also forms channels or slots 144, 146 that extend along the central spike 136 to facilitate flow of the drug into the central channel 140.

The base 138 of the cup-shaped drug vial spike 120 includes multiple leaf springs 152. The leaf springs 152 are resilient members that are biased upward (i.e., in the direction of the drug vial 116, 118 when the drug vial 116, 118 has been loaded onto the drug vial spike 120). The leaf springs 152 are disposed over apertures 154 formed in the base. When the drug vial 116, 118 is loaded into place, each leaf spring 152 is depressed, allowing the top edge of the vial cap 119 to temporarily lock into place under an annular flange 150 formed by the side wall of the drug vial spike 120. The resilient leaf springs 152 provide for retraction of the central spike 136 relative to the vial 116, 118 after the spike 136 has been fully inserted into the vial 116, 118 (i.e., after the cap 123 of the vial 116, 118 has contacted the base 138 of the drug vial spike 120). Because the resilient leaf springs 152 are biased toward the drug vial 116, 118, after the drug vial 116, 118 is loaded onto the central spike 136 by deforming the leaf springs 152 inward toward the base 138, the leaf springs 152 force the vial 116, 118 back away from the base 138. Due to the friction forces between the rubber seal 123 of the vial 116, 118 and the central spike 136 of the drug vial spike 120, the portion of the rubber seal 123 contacting the central spike 136 moves away from the base 138 of the drug vial spike 120 to a lesser extent than the remainder of the vial 116, 118 when this outward force is applied to the drug vial 116, 118. In certain implementations, for example, the portion of the rubber seal 123 contacting the central spike 136 does not move at all in response to the outward forces of the leaf springs 152. Because the portion of the rubber seal 123 in contact with the central spike 136 moves a shorter distance relative to the drug vial spike 120 than the remainder of the vial 116, 118, the central portion of the rubber seal 123 tends to bulge away from the vial 116, 118, and the central spike 136 remains embedded in the vial 116, 118 and able to access the drug or fluid contained therein. The rubber seal 123 can, for example, form a concave shape or dish shape, which helps to ensure that the full contents of the drug vial 116, 118 are evacuated from the vial.

By helping to ensure that the full contents of the drug vial 116, 118 are evacuated, the drug vial spike 120 provides significant advantages compared to certain conventional spikes and syringes. For example, when many conventional spikes or syringes puncture the rubber seal of a drug vial, the spike or syringe pushes portions of the rubber seal surrounding the spike or syringe inward. As a result, medication may become adhered to or get lodged behind the surface of the inwardly folded portion of the rubber seal. As a result, some of the drug becomes trapped within the vial and is not used. The trapped portion of the drug is typically discarded with the vial. Certain drugs, such as Epogen®, are very expensive, and thus even one droplet left behind in the vial can be worth a significant price to the patient and/or care provider, especially over the course of multiple treatments. Thus, the drug vial spikes 120 described herein can save patients and/or care providers a significant amount of money over time and can ensure that life-saving drugs are not wasted. In addition, the drug vial spikes 120 can increase the accuracy with which prescribed drug dosages are delivered to patients, which can improve patient health.

Still referring to FIGS. 4-6, the drug vial spike 120 also includes multiple bi-stable members 148 positioned around the central spike 136 of the drug vial spike 120. As provided to the user, the bi-stable members 148 are in a first position (i.e., deformed away from the base 138 into the drug vial recess). Apertures sized and shaped to allow the bi-stable members 148 to pass therethrough are provided in the base 138 below the bi-stable members 148. The bi-stable members 148 are configured to snap into a second position (i.e., deformed away from the base 138 and out of the drug vial recess) when forces of a given magnitude in a direction opposite the vial 116, 118 are applied to the members. As a result, when the vial 116, 118 has been properly seated within the vial recess of the drug vial spike 120, the drug vial applies a force to each of the bi-stable members 148, causing the bi-stable members 148 to snap into this second position. In this second position, at least a portion of each bi-stable member 148 protrudes beyond the bottom surface of the base 138 opposite the vial. Thus, the bi-stable members 148 provide visual confirmation to the user that the vial is properly seated within the vial recess of the drug vial spike 120.

As shown in FIGS. 3 and 6, the circumferential side wall of the drug vial spike 120 extends to a slightly greater height than the central spike 136. This configuration, in addition to helping secure the drug vial within the cavity formed by the drug vial spike 120, helps to ensure that the central spike 136 is not inadvertently contacted (e.g., by the operator) prior to loading of a drug vial onto the spike. This can, for example, help to prevent the central spike 136 from being contaminated before it is inserted into the drug vial.

In some implementations, the drug vial spikes 20 are formed of one or more medical grade plastics, such as PVC or acrylonitrile butadiene styrene (ABS). However, other medical grade plastics can be used to form the drug vial spike 120. Similarly, certain metals, such as stainless steel, could be used to form the drug vial spike 120.

Epogen® is provided in two single-dose 1 ml vials with various concentrations and two multi-dose vials with two different concentrations. The contents of each of these vials are described below.

Single-dose, Preservative-free Vial—1 mL (2,000, 3,000, 4,000, or 10,000 Units/mL). Each 1 mL of solution contains 2,000, 3,000, 4,000 or 10,000 Units of Epoetin alfa, 2.5 mg Albumin (Human), 5.8 mg sodium citrate, 5.8 mg sodium chloride, and 0.06 mg citric acid in Water for Injection, USP (pH 6.9±0.3). This formulation contains no preservative.

Single-dose, Preservative-free Vial—1 mL (40,000 Units/mL). Each 1 mL of solution contains 40,000 Units of Epoetin alfa, 2.5 mg Albumin (Human), 1.2 mg sodium phosphate monobasic monohydrate, 1.8 mg sodium phosphate dibasic anhydrate, 0.7 mg sodium citrate, 5.8 mg sodium chloride, and 6.8 mcg citric acid in Water for Injection, USP (pH 6.9±0.3). This formulation contains no preservative.

Multidose, Preserved Vial—2 mL (20,000 Units, 10,000 Units/mL). Each 1 mL of solution contains 10,000 Units of Epoetin alfa, 2.5 mg Albumin (Human), 1.3 mg sodium citrate, 8.2 mg sodium chloride, 0.11 mg citric acid, and 1% benzyl alcohol as preservative in Water for Injection, USP (pH 6.1±0.3).

Multidose, Preserved Vial—1 mL (20,000 Units/mL). Each 1 mL of solution contains 20,000 Units of Epoetin alfa, 2.5 mg Albumin (Human), 1.3 mg sodium citrate, 8.2 mg sodium chloride, 0.11 mg citric acid, and 1% benzyl alcohol as preservative in Water for Injection, USP (pH 6.1±0.3).

Thus, Epogen® vials are provided in the following standard concentrations: 2,000 units per vial, 3,000 units per vial, 4,000 units per vial, 10,000 units per vial, 20,000 units per vial, and 40,000 units per vial.

The prescribed dosage of Epogen® is individualized for each patient on dialysis, and the prescribed dosage can vary dramatically from one patient to another. However, it has been found that by using from one to three full vials in various different combinations, over 90 percent of patient dosage requirements can be fulfilled. The drug delivery device can be operated in a manner to provide any of various different discrete dosages between 0 and 20,000 units with various different combinations of three vials, and can thus be used to treat over 90 percent of dialysis patients without having to change vials during use or use customized Epogen®. In addition, because substantially all of the Epogen® is drained from each of the vials that is used, very little, if any, Epogen®, which is a very expensive drug, is wasted.

The Epogen® dosing schedule described below can be used by the operator of the drug delivery device to reduce or minimize waste of Epogen®. The dosing schedule has been developed to give guidance to the prescriber such that the correct average dose can be administered using permutations of three vials per treatment and permutations of three weekly treatments. The permutations can be weighted by the measure of dosage variation (standard deviation) or by the minimum number of vials selected.

Table 1 below illustrates that each of the drug channels of the drug vial holder of the drug delivery device can be loaded with a vial containing 2,000 units of Epogen®, 3,000 units of Epogen®, 4,000 units of Epogen®, 10,000 units of Epogen®, 20,000 units of Epogen®, or 40,000 units of Epogen®, or with no vial at all.

TABLE 1

| Vial 1 | Vial 2 | Vial 3 |
|---|---|---|
| 0 | 0 | 0 |
| 2000 | 2000 | 2000 |
| 3000 | 3000 | 3000 |
| 4000 | 4000 | 4000 |
| 10000 | 10000 | 10000 |
| 20000 | 20000 | 20000 |
| 40000 | 40000 | 40000 |

In many cases, a desired Epogen® delivery amount for a single treatment will not equal the amount of Epogen® that is currently manufactured and provided in a single vial. In those cases, two or more vials of Epogen® need to be used to deliver the desired amount. There are multiple permutations that satisfy some of these unique delivery amount requirements. Table 2 below shows these various permutations for a single treatment. In particular the first three columns of the table show the three vials used in each permutation, the fourth column shows the total amount delivered by using those particular three vials, the fifth column shows the standard deviation (i.e., the volume variance experienced throughout the treatment as a result of using the three different vials (the difference between the sum of the volumes and the average volume)), and the sixth column shows the total number of vials used during the treatment.

TABLE 2

| Vial 1 | Vial 2 | Vial 3 | Total Dose | Stdev | Num Vials |
|---|---|---|---|---|---|
| 0 | 0 | 0 | 0 | 0 | 0 |
| 2000 | 0 | 0 | 2000 | 1155 | 1 |
| 3000 | 0 | 0 | 3000 | 1732 | 1 |
| 2000 | 2000 | 0 | 4000 | 1155 | 2 |
| 4000 | 0 | 0 | 4000 | 2309 | 1 |
| 3000 | 2000 | 0 | 5000 | 1528 | 2 |
| 3000 | 3000 | 0 | 6000 | 1732 | 2 |
| 4000 | 2000 | 0 | 6000 | 2000 | 2 |
| 2000 | 2000 | 2000 | 6000 | 0 | 3 |
| 4000 | 3000 | 0 | 7000 | 2082 | 2 |
| 3000 | 2000 | 2000 | 7000 | 577 | 3 |
| 4000 | 4000 | 0 | 8000 | 2309 | 2 |
| 3000 | 3000 | 2000 | 8000 | 577 | 3 |
| 4000 | 2000 | 2000 | 8000 | 1155 | 3 |
| 4000 | 3000 | 2000 | 9000 | 1000 | 3 |
| 3000 | 3000 | 3000 | 9000 | 0 | 3 |
| 10000 | 0 | 0 | 10000 | 5774 | 1 |
| 4000 | 4000 | 2000 | 10000 | 1155 | 3 |
| 4000 | 3000 | 3000 | 10000 | 577 | 3 |
| 4000 | 4000 | 3000 | 11000 | 577 | 3 |
| 10000 | 2000 | 0 | 12000 | 5292 | 2 |
| 4000 | 4000 | 4000 | 12000 | 0 | 3 |
| 10000 | 3000 | 0 | 13000 | 5132 | 2 |
| 10000 | 4000 | 0 | 14000 | 5033 | 2 |
| 10000 | 2000 | 2000 | 14000 | 4619 | 3 |
| 10000 | 3000 | 2000 | 15000 | 4359 | 3 |
| 10000 | 4000 | 2000 | 16000 | 4163 | 3 |
| 10000 | 3000 | 3000 | 16000 | 4041 | 3 |
| 10000 | 4000 | 3000 | 17000 | 3786 | 3 |
| 10000 | 4000 | 4000 | 18000 | 3464 | 3 |
| 10000 | 10000 | 0 | 20000 | 5774 | 2 |
| 20000 | 0 | 0 | 20000 | 11547 | 1 |
| 20000 | 2000 | 0 | 22000 | 11015 | 2 |
| 10000 | 10000 | 2000 | 22000 | 4619 | 3 |
| 20000 | 3000 | 0 | 23000 | 10786 | 2 |
| 10000 | 10000 | 3000 | 23000 | 4041 | 3 |
| 20000 | 4000 | 0 | 24000 | 10583 | 2 |
| 20000 | 2000 | 2000 | 24000 | 10392 | 3 |
| 10000 | 10000 | 4000 | 24000 | 3464 | 3 |
| 20000 | 3000 | 2000 | 25000 | 10116 | 3 |
| 20000 | 4000 | 2000 | 26000 | 9866 | 3 |
| 20000 | 3000 | 3000 | 26000 | 9815 | 3 |
| 20000 | 4000 | 3000 | 27000 | 9539 | 3 |
| 20000 | 4000 | 4000 | 28000 | 9238 | 3 |
| 20000 | 10000 | 0 | 30000 | 10000 | 2 |
| 10000 | 10000 | 10000 | 30000 | 0 | 3 |
| 20000 | 10000 | 2000 | 32000 | 9018 | 3 |
| 20000 | 10000 | 3000 | 33000 | 8544 | 3 |
| 20000 | 10000 | 4000 | 34000 | 8083 | 3 |
| 20000 | 20000 | 0 | 40000 | 11547 | 2 |
| 40000 | 0 | 0 | 40000 | 23094 | 1 |
| 20000 | 10000 | 10000 | 40000 | 5774 | 3 |
| 40000 | 2000 | 0 | 42000 | 22539 | 2 |
| 20000 | 20000 | 2000 | 42000 | 10392 | 3 |
| 40000 | 3000 | 0 | 43000 | 22279 | 2 |
| 20000 | 20000 | 3000 | 43000 | 9815 | 3 |
| 40000 | 4000 | 0 | 44000 | 22030 | 2 |
| 40000 | 2000 | 2000 | 44000 | 21939 | 3 |
| 20000 | 20000 | 4000 | 44000 | 9238 | 3 |
| 40000 | 3000 | 2000 | 45000 | 21656 | 3 |
| 40000 | 4000 | 2000 | 46000 | 21385 | 3 |
| 40000 | 3000 | 3000 | 46000 | 21362 | 3 |
| 40000 | 4000 | 3000 | 47000 | 21079 | 3 |
| 40000 | 4000 | 4000 | 48000 | 20785 | 3 |
| 40000 | 10000 | 0 | 50000 | 20817 | 2 |
| 20000 | 20000 | 10000 | 50000 | 5774 | 3 |
| 40000 | 10000 | 2000 | 52000 | 20033 | 3 |
| 40000 | 10000 | 3000 | 53000 | 19655 | 3 |
| 40000 | 10000 | 4000 | 54000 | 19287 | 3 |
| 40000 | 20000 | 0 | 60000 | 20000 | 2 |
| 40000 | 10000 | 10000 | 60000 | 17321 | 3 |
| 20000 | 20000 | 20000 | 60000 | 0 | 3 |
| 40000 | 20000 | 2000 | 62000 | 19009 | 3 |
| 40000 | 20000 | 3000 | 63000 | 18520 | 3 |
| 40000 | 20000 | 4000 | 64000 | 18037 | 3 |
| 40000 | 20000 | 10000 | 70000 | 15275 | 3 |
| 40000 | 40000 | 0 | 80000 | 23094 | 2 |
| 40000 | 20000 | 20000 | 80000 | 11547 | 3 |
| 40000 | 40000 | 2000 | 82000 | 21939 | 3 |
| 40000 | 40000 | 3000 | 83000 | 21362 | 3 |
| 40000 | 40000 | 4000 | 84000 | 20785 | 3 |
| 40000 | 40000 | 10000 | 90000 | 17321 | 3 |
| 40000 | 40000 | 20000 | 100000 | 11547 | 3 |
| 40000 | 40000 | 40000 | 120000 | 0 | 3 |

The operator can consult the above table to determine the most desirable combination of vials. The operator may, for example, select the combination that requires the fewest vials to deliver the desired amount of drug for the treatment. The user may alternatively select the combination of vials based on the variation in drug delivery amount throughout the drug delivery process or the amount of time required to deliver the drug (not shown in the table above).

This vial selection strategy can also be extended to permutations of the treatment doses to give an average weekly dose with better resolution. For example, with the above combinations, the same permutation schedule can be used to achieve an average weekly dose. In Table 3 below, the first three columns show the dosage used for each of three weekly treatments, the fourth columns shows the average dosage achieved over those three weekly treatments, and the fifth column shows the standard deviation (i.e., the variance in dosage over the three weekly treatments (the difference between the sum of the dosages and the average dosage)).

TABLE 3

| Treatment Dosage (3 Treatments per Week) | | | Average Dosage | Stdev |
|---|---|---|---|---|
| 2000 | 2000 | 2000 | 2000 | 0 |
| 2000 | 2000 | 3000 | 2333 | 577 |
| 2000 | 3000 | 2000 | 2333 | 577 |
| 3000 | 2000 | 2000 | 2333 | 577 |
| 2000 | 2000 | 4000 | 2667 | 1155 |
| 2000 | 3000 | 3000 | 2667 | 577 |
| 2000 | 4000 | 2000 | 2667 | 1155 |
| 3000 | 2000 | 3000 | 2667 | 577 |
| 3000 | 3000 | 2000 | 2667 | 577 |
| 4000 | 2000 | 2000 | 2667 | 1155 |
| 2000 | 2000 | 5000 | 3000 | 1732 |
| ... | ... | ... | ... | ... |
| 20000 | 20000 | 17000 | 19000 | 1732 |
| 18000 | 20000 | 20000 | 19333 | 1155 |
| 20000 | 18000 | 20000 | 19333 | 1155 |
| 20000 | 20000 | 18000 | 19333 | 1155 |
| 20000 | 20000 | 20000 | 20000 | 0 |

The above tables can be consulted to minimize the number of vials used per week while maintaining the dosage variation over the three weekly treatments within an acceptable range. As an example, if the prescribed dosage is 16,000 units of Epogen®, the user first consults Table 2 above to determine which combinations of vials add up to this dosage. Table 2 above shows that the user can use: one 10,000 unit vial, one 4,000 unit vial, and one 2,000 unit vial; or one 10,000 unit vial and two 3,000 unit vials. Thus, the fewest number of vials that the user could use for the treatment would be three vials. This would mean that nine vials were required per week (three vials per treatment and three treatments per week). However, the user can then consult Table 3 above to determine whether it is possible to reduce the number of vials used per week by focusing on the average dosage per week as opposed to the dosage per individual treatment. To do this, the user would look to Table 3 to determine the different treatment dosages that could be used for each of the three weekly treatments in order to achieve an average dosage of 16,000 units. If any of those options had a standard deviation (or dosage variance) that was below an acceptable maximum dosage variance, the user would look back to the first table to determine the vial combinations that could be used to achieve each of those treatment dosages. Based on those vial combinations, the user could determine the total number of vials that would be required for the week and compare that number to the total number of required vials determined from Table 2 (i.e., nine vials). If any of the alternative vial combinations result in fewer than nine vials per week, then the user could use the dosing schedule provided by Table 3.

Although Epogen® dosages are generally prescribed based on a single treatment, Table 3 above can be consulted by physicians when prescribing Epogen® and those physicians can prescribe dosages that are provided on the table. Prescribing Epogen® in this manner can help to ensure that treatments can be carried out on average with fewer vials and can thus reduce the amount of material (e.g., used vials) that need to be discarded after treatment and the inventory of vials that need to be maintained. In addition, by purchasing the same volume of drug in fewer vials, the overall cost of that drug can be reduced.

While Table 3 above relates to treatments over a period of one week, similar tables can be prepared and consulted for any of various other time periods (e.g., two weeks, one month, two months, six months, etc.).

The calculations described above relating to maximizing the effective dosages of Epogen® may be used for other drugs as well. For example, a dosing schedule of the type described above can be used to determine the most desirable approach for delivering the Venofer® over multiple treatments. Unlike Epogen®, however, Venofer® is relatively inexpensive, so it is generally of less concern from a cost standpoint to minimize the number of vials of Venofer® used over a given period of time (e.g., one week or one month). However, such a dosing schedule can reduce (e.g., minimize) the amount of materials (e.g., used vials) to be discarded and can reduce the effort and time required to set up the device for drug delivery.

The above-described dosing schedules can be provided to the user in any of various different formats. In some implementations, the tables are simply printed on a document (e.g., a user manual, a laminated card, etc.) that the user can consult during treatment. In certain implementations, the tables are provided to the user in the form of electronic files that can be saved to a computer or viewed online.

In some implementations, the dosing schedule is provided as a computer program installed in the drug delivery device 103. In such implementations, the user would input the prescribed dosage information and the control unit of the drug delivery device 103 would display the relevant portions of the tables on the user interface. The user could then examine the displayed portions of the tables on the user interface and, based on that displayed information, determine a desirable combination of vials to use for the treatment. Alternatively or additionally, the computer program could be designed to automatically determine the best combination of vials to use for the treatment (e.g., based on preferences input by the user) and display that vial combination for the user.

Figure 7:
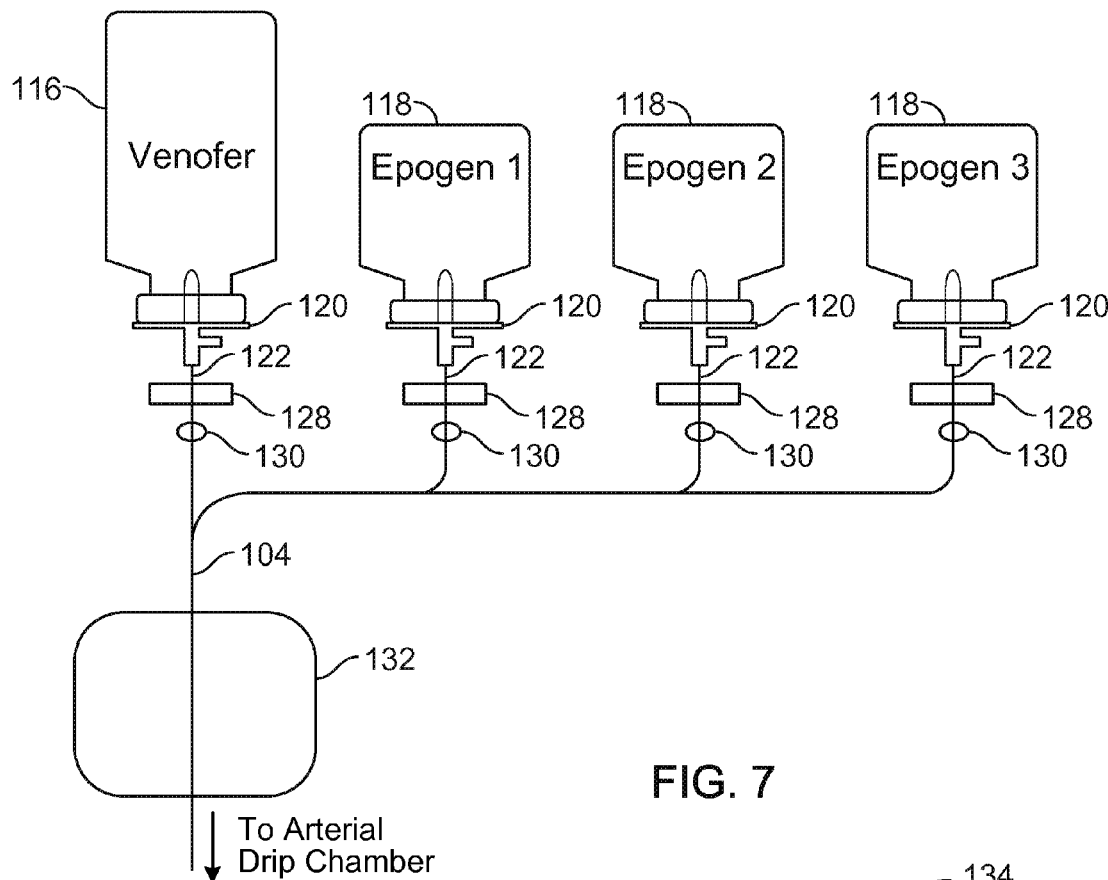
FIG. 7 is a schematic of certain components of the modular drug delivery device of the hemodialysis machine of FIG. 1 in use with the drug vials and the drug administration fluid line set secured thereto. The drug administration fluid line set includes a series of fluid lines and a drug vial spike connected to each of the drug vials.

Referring to FIGS. 1 and 7, prior to beginning hemodialysis treatment on a patient, the various lines that make up the blood circuit and dialysate circuit of the hemodialysis machine are primed, and then the patient lines 105 are connected to the patient. After connecting the patient lines 105 to the patient, the blood pump 108 is activated to circulate blood through the blood circuit. A dialysate pump is also activated to pump dialysate through the dialysate circuit of the hemodialysis machine. The blood is drawn from the patient and delivered to the drip chamber 106 via the arterial patient line. The drip chamber 106 acts as an air trap such that any air in the blood is released as the blood passes through the drip chamber 106. In particular, the drip chamber 106 includes a vent through which air released from the blood can be vented from the drip chamber 106. The blood is then pumped from the drip chamber 106 to the dialyzer 110, which includes a semi-permeable membrane that divides the dialyzer 110 into two chambers. As the blood passes through one of the chambers of the dialyzer 110, dialysate from the dialysate circuit passes through the other chamber. As the blood flows by the dialysis fluid, impurities, such as urea and creatinine, diffuse through the semi-permeable membrane into the dialysate. The spent dialysate is either disposed of or recycled and reused. The cleansed blood exiting the dialyzer 110 is returned to the patient via the venous patient line.

Since the drug delivery process is usually shorter than the overall hemodialysis process, the set up of the drug delivery device 103 and its associated components typically occurs after hemodialysis treatment has begun. In order to prepare the drug delivery device 103 for use, the user first determines the prescribed Epogen® dose and then consults a dosing schedule for the different vial combinations that can be used to deliver the prescribed Epogen® dose. The user then selects one of the Epogen® vial combinations provided based on the user's preference. The user can, for example, choose the vial combination that requires the fewest number of vials for the upcoming treatment or for multiple treatments over a given time (e.g., one week, one month, etc.), or the vial combination that provides the most consistent amount of drug delivered per treatment (e.g., based on one week worth of treatments, one month worth of treatments, etc.). Alternatively, the user can consider both the number of vials required and the consistency of the drug amount delivered over a given number of treatments to select a vial combination. As discussed above, in certain implementations, the best combination of vials (based on the user's preferences) is automatically displayed on the user interface for the user to read. After choosing a desired combination, the user gathers the necessary Epogen® vials from a vial storage supply (e.g., a refrigerator).

The user then connects the disposable drug administration fluid line set 107, which includes the drug vial spikes 120, the drug feeder lines 122, and the drug delivery line 104, to the drug delivery device 103. The drug administration fluid line set 107 is typically provided to the user in a sterile bag. To connect the drug administration fluid line set 107 to the drug delivery device 103, the user first opens the sterile bag and removes the drug administration fluid line set 107. The user then positions each of the drug vial spikes 120 within one of the drug channels 114 of the drug vial holder 112, threads the feeder lines 122 through their respective bubble detectors 128 and occluders 130, and connects the drug delivery line 104 to the drip chamber 106 using an aseptic technique. This last step typically involves connecting a luer lock fitting on the end of the drug delivery line 104 to a mating luer lock fitting on a drip chamber level adjust line extending from the drip chamber 106. However, other types of connectors can be used.

Once the drug administration fluid line set 107 is in place, the Venofer® vial 116 and Epogen® vials 118 are loaded into the channels 114 of the drug vial holder 112. In particular, each vial 116, 118 is inverted and inserted into its associated channel 114 so that the central spike 136 of the associated drug vial spike 120 pierces the rubber seal 123 of the vial 116, 118. As discussed above, this arrangement allows the drug within the vial 116, 118 to pass through the drug vial spike 120 and into the feeder line 122 connected to the drug vial spike 120. Use of the drug vial spikes 120 is advantageous because the drugs can be directly delivered from their sterile vial 116, 118 without using an intermediary needle to transfer the drug from the vial 116, 118 to the patient.

While FIG. 1 illustrates the use of four vials (i.e., one Venofer® vial 116 and three Epogen® vials 118) in the four-channel vial holder 112, it should be understood that fewer vials may be used, depending on the prescribed dosage requirement and the operator's preferences. In such cases, one or more of the drug vial holder's channels 112 would simply be empty (i.e., no drug vial would be disposed in one or more of the channels 112).

After loading the Venofer® and Epogen® vials 116, 118, the prescribed dosages of Venofer® and Epogen® are entered into the drug delivery device 103 using the user interface 134. As discussed below, it is often the case that the full amount of Venofer® in the Venofer® vial is not required to achieve the prescribed dosage. Therefore, it may be important to input the prescribed dosage of Venofer® to ensure that the proper amount of Venofer® is delivered to the patient. On the other hand, the combination of Epogen® vials generally amount to the prescribed Epogen® dosage. Thus, even without entering the prescribed Epogen® dosage, the prescribed dosage should be achieved by simply fully evacuating each of the Epogen® vials 118. Entering the prescribed Epogen® dosage, however, can enable the drug delivery device 103 to confirm that the actual amount of Epogen® delivered from the vials is equal to the prescribed Epogen® dosage.

After entering the prescribed dosages of Venofer® and Epogen®, each of the feeder lines 122 is primed. Priming can be an automated process that begins after the operator confirms that the vials have been loaded (e.g., by pressing a button on the user interface 134) or after the drug delivery device 103 confirms that all necessary vials are in place. To prime the feeder lines 122, the drug pump 132 is activated and the occluders 130 are sequentially opened. Each occluder 130 remains open for a predetermined time after the drug from its associated vial is detected by the bubble detector 128. After detection of the drug by the air bubble detector 128 associated with the Venofer® vial 116 (i.e., the first vial that is to be emptied during the drug delivery process), the drug pump 132 continues to operate and the occluder 130 associated with the feeder line 122 connected to that vial remains open for a sufficient period of time to cause the Venofer® to substantially fill the drug delivery line 104. Substantially filling the feeder line with the Venofer® ensures that as additional Venofer® is drawn from the vial 116, Venofer® will enter the drip chamber 106. After filling the drug delivery line 104 with the Venofer®, the occluder 130 associated with the feeder line 122 connected to the vial 116 pinches that feeder line 122 and one of the other occluders 130 is opened to prime the feeder line 122 associated with the open occluder 130. This process is repeated until each of the feeder lines 122 has been primed.

If the drug is not detected by one of the air bubble detectors 128 during the priming process, an alarm is activated. This indicates a problem with either the drug delivery device 103 (e.g., the bubble detector 128 of the drug delivery device 103) or the drug administration fluid line set 107 (e.g., the drug vial spike 120 or feeder line 122 of the drug administration fluid line set 107). In response to the alarm, the user typically replaces the drug administration fluid line set 107 or adjusts the drug administration fluid line set 107 and repeats the process.

Priming the feeder lines in this manner is advantageous in that it increases the probability of the clinician (if being used in a clinic setting) being nearby to quickly replace the drug administration fluid line set 107 if a malfunction is detected. Without priming the feeder lines 122, for example, a defect in the administration set might not be detected until the middle of the drug delivery process when the drug is first pulled from the drug vial associated with the portion of the drug administration fluid line set 107 including the defect. In that case, the treatment would have to be stopped until the clinician made his or her way over to the machine to rectify the problem.

After priming the feeder lines 122, Venofer® is delivered from the Venofer® vial 116 to the drip chamber 106 where it mixes with the patient's blood. The Venofer® is delivered to the patient by opening the occluder 130 associated with the Venofer® vial 116 (while leaving all of the other occluders 130 closed) and running the drug pump 132. Venofer® is a relatively inexpensive drug, so it is less important to ensure that all of the Venofer® is fully evacuated from the vial 116, as compared to the Epogen®. In some cases, the prescribed dosage of the Venofer® will be less than the amount of Venofer® contained in the vial 116 such that some of the Venofer® will remain in the vial after prescribed volume of the drug is delivered. The volume of Venofer® delivered to the patient is monitored and controlled by the control unit and the drug pump 132 of the drug delivery device 103. The peristaltic drug pump 132 works by compressing the drug delivery line 104 and moving a "pillow" of fluid that is pinched between two points of the drug delivery line 104 by the pump rollers. Each "pillow" of fluid is of a volume determined by the roller spacing and the inside diameter of the drug delivery line 104. When the pump 132 operates at a given speed, a series of these "pillow" shaped volumes of fluid are delivered to the drip chamber 106. By changing the speed of the pump 132, the rate of fluid delivery is changed. The pump speed can be controlled by adjusting the voltage delivered to the pump 132. The voltage delivered to the motor of the pump 132 can, for example, be adjusted by the control unit (e.g., software of the control unit) until the correct speed (i.e., the speed that corresponds to the desired flow rate) is measured on the encoder.

As discussed above, the drip chamber 106 of the hemodialysis system 100 functions as an air trap. Thus, any gases (e.g., air) introduced into the system (for example, air drawn in from one of the vials 116, 118) are able to escape from the drug and blood within the drip chamber 106. In addition to removing air from the system, the drip chamber 106 provides other benefits. For example, the drip chamber 106 provides visual confirmation of drug delivery and allows the delivered drug to mix with the patient's blood prior to reaching the patient. In addition, the drip chamber 106 allows for simple luer connection to the drug administration fluid line set 107. As a result, the patient need not be stuck with an additional needle in order to receive the drugs from the vials 116, 118.

Figure 8:
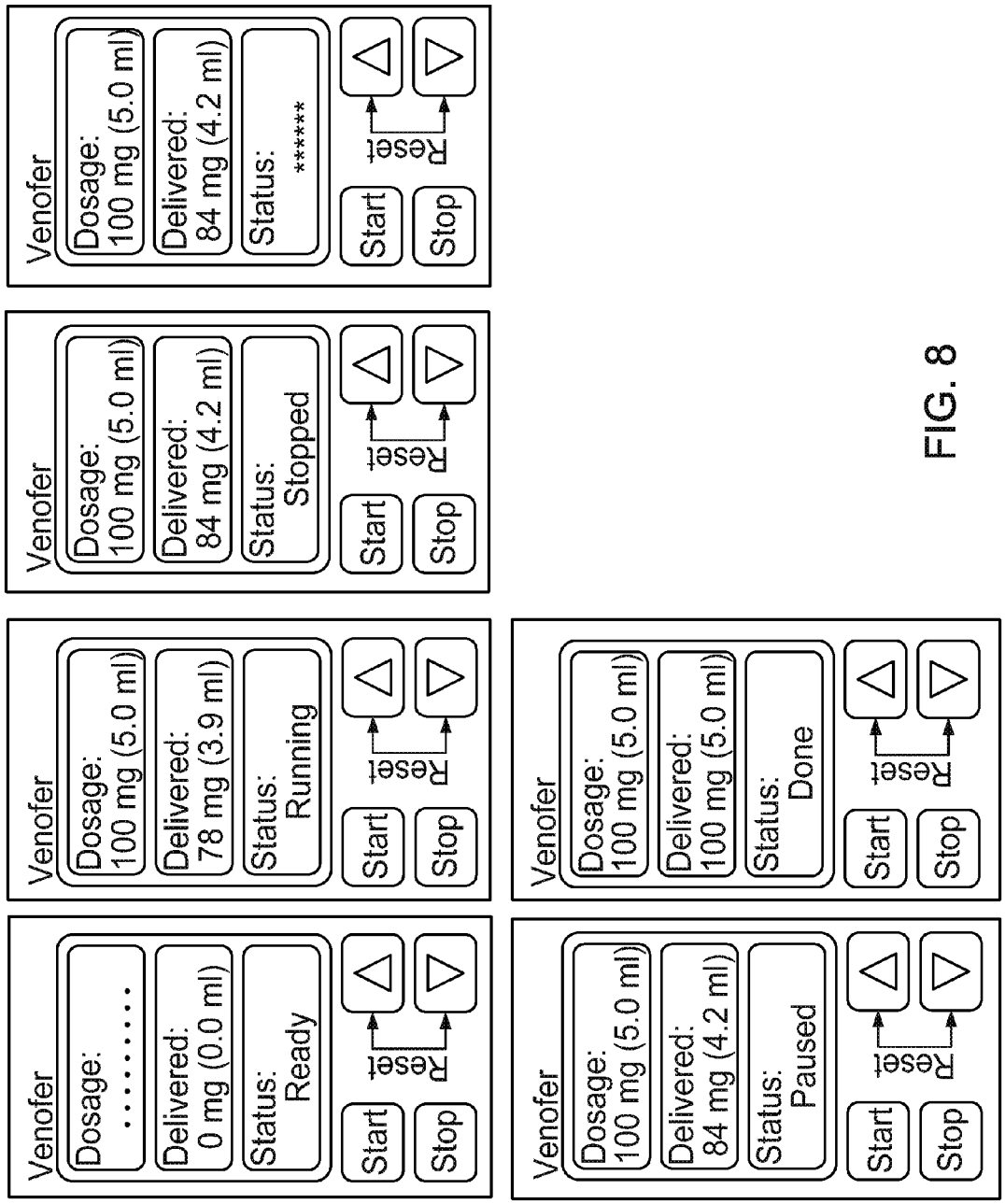
FIG. 8 illustrates a portion of a user interface of the modular drug delivery device during various different stages of the drug delivery.

FIG. 8 illustrates a series of user interface screen shots during the Venofer® delivery processes. As shown, the user interface displays the prescribed dosage and the dosage delivered. When the dosage delivered is equal to the prescribed dosage, that indicates to the user that the Venofer® delivery process is complete. In situations where the prescribed dosage of Venofer® exceeds the number of units provided in the vial, the status would alternatively read "Replace Vial" after delivering the full contents of the first vial. This would prompt the operator to replace the first Venofer® vial with a second Venofer® in order to enable the prescribed dosage to be achieved. Upon determining that the prescribed dosage of Venofer® has been delivered to the drip chamber 106, the control unit causes the occluder 130 associated with the Venofer® feeder line to be closed.

Venofer® reaches its full potential through precise delivery over an extended period of time. With controlled drug infusion using the peristaltic drug pump 132 and the drip chamber 106, the Venofer® can be delivered at a precise rate that will keep the drug concentration within the therapeutic margin and out of the toxic range. The peristaltic drug pump 132 is able to provide appropriate drug delivery to the patient at a controllable rate, which does not require frequent medical attention.

Referring again to FIGS. 1 and 7, after the desired amount of Venofer® has been delivered to the drip chamber 106 and its associated occluder 130 has been closed, the occluder 130 associated with the first Epogen® vial 118 (i.e., the Epogen® vial directly to the right of the Venofer® vial 116) is opened such that Epogen® is delivered to the drip chamber 106. The combination of Epogen® vials 118 has been selected so that the prescribed dosage of Epogen® is equal to the Epogen® contained in the three Epogen® vials 118. Thus, it is not generally necessary to monitor the volume of Epogen® delivered to the drip chamber 106. However, in many cases, the peristaltic drug pump 132 (or the control unit that is connected to the drug pump 132) monitors the amount of Epogen® delivered to confirm that the amount of Epogen® delivered is equal to the prescribed amount. This can, for example, help to identify a situation in which an incorrect Epogen® vial was used (e.g., due to user error or mislabeling). Because the full volume of the Epogen® vial 118 is to be used, the occluder 130 associated with the Epogen® vial 118 is simply kept open until the bubble detector 128 detects an air bubble in the feeder line 122, indicating that the full volume of Epogen® was evacuated from the vial 118 (i.e., indicating that the vial 118 is empty). When the bubble detector 128 detects air in the feeder line 122, a signal is sent to the control unit, indicating that the first Epogen® vial 118 is empty. The control system then sends a signal to the occluder 130 associated with the first Epogen® vial 118 to clamp off the feeder line 122 associated with the first Epogen® vial 118 after assuring that an additional known volume is pumped so that the Epogen® in the line downstream of the bubble detector 128 is flushed down to a segment where the Epogen® from the next vial can push that Epogen® remaining in the line to the drip chamber 106. In particular, the control unit ensures that the additional pumped volume is sufficient to push the Epogen® past the occluder 130 such that the next volume delivered will push the Epogen® into and through the drug delivery line 104 to the drip chamber 106. The control unit also sends a signal to the occluder 130 associated with the second Epogen® vial 118 (i.e., the Epogen® vial directly to the right of the first Epogen® vial) to open the feeder line 122 associated with the second Epogen® vial 118. The Epogen® delivery process described above is then repeated for the second and third Epogen® vials.

Figure 9:
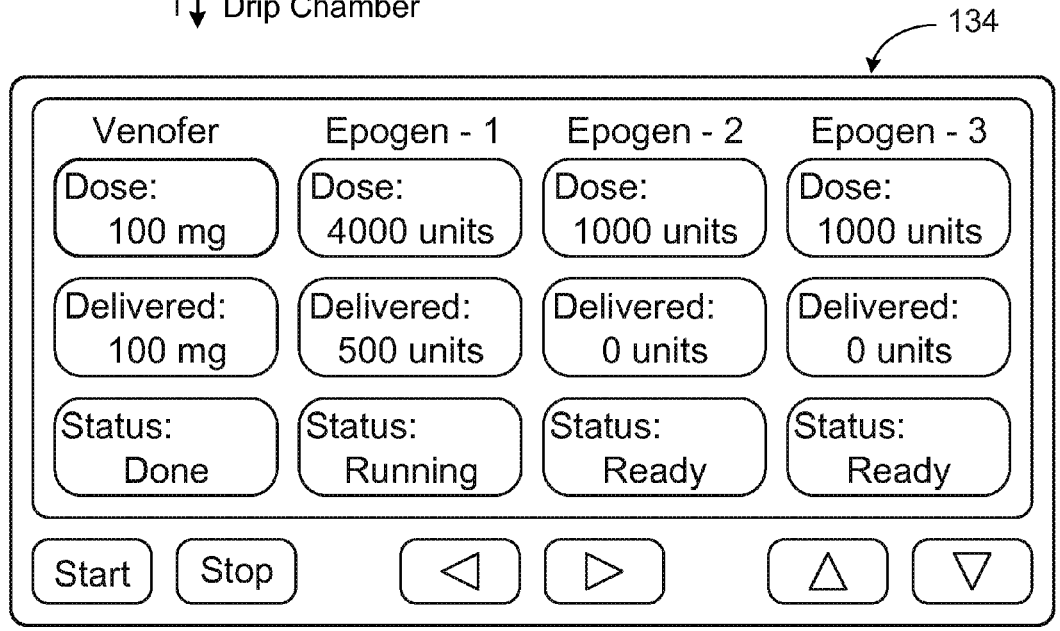
FIG. 9 illustrates a snapshot of the user interface of the modular drug delivery device during the drug delivery.

FIG. 9 is a screen shot of the user interface 134 of the drug delivery device 103 during the delivery of Epogen® from the first Epogen® vial 118. As shown, the portion of the display dedicated to the Venofer® vial indicates that the full prescribed dosage of the Venofer® has been delivered and that the Venofer® delivery process is thus complete. The portion of the screen dedicated to the first Epogen® vial indicates that the Epogen® from that vial is in the process of being delivered to the patient. In particular, it shows that 500 units of the 4,000 unit vial have been delivered. The screen further shows that delivery for the second and third Epogen® vials has not yet begun and that each of those vials contains 1,000 units of Epogen®. In treatments where fewer than three Epogen® vials are to be delivered, the portion of the screen dedicated to the missing vials would indicate that no drug is to be delivered from that/those channel(s).

As discussed above, the design of the drug vial spikes 120 helps to ensure that the Venofer® and Epogen® vials 116, 118 are fully evacuated during treatment. In particular, the outward bulge created in the rubber seal 123 of each vial 116, 118 creates a dish-shaped recess along the inner surface of the rubber seal 123. This recess functions as a funnel to ensure that substantially all of the drug flows out of the vial 116, 118 and into the feeder line 122. Traditionally, drug vials have been filled in a manner to include a slightly greater volume of drug in the vials than the vial label indicates. This has been due to the inability of conventional drug delivery mechanisms to evacuate all of the drug from the vial. The drug vial spikes 120 described herein can help to prevent the drug from being trapped in the vial and discarded with the vial. Thus, the vials 116, 118 used in the drug delivery system 102 need not be overfilled.

After delivering the desired amounts of Venofer® and Epogen®, the drug delivery device 103 is deactivated and the drug administration fluid line set 107 and vials 116, 118 are removed from the drug delivery device 103 and discarded.

In some implementations, between each transition from one vial to the next, an air bubble is pulled into the drug delivery line 104 via the feeder line 122. In particular, air is pulled into the feeder line 122 from the newly empty vial, and the resulting air bubble is delivered to the drip chamber 106, where the air bubble is removed from the system. As the air bubble moves from the feeder line 122 to the drip chamber 106, it clears any remaining medicament from the previously used vial out of the feeder line 122, the drug delivery line 104, and the various lines and connections therebetween. This helps to ensure that all of the drug evacuated from the vial is delivered to the patient. It also reduces (e.g., eliminates) mixing of two distinct drugs that are delivered by the same line running through the same/singular pump. Many drugs may cause an adverse reaction by the patient if they are mixed prior to delivery to the patient. This techniques is advantageous in that it can help to prevent mixing of such drugs before they reach the patient's blood.

In certain implementations, the control unit operates the components of the drug delivery device 103 in a manner so that an air bubble is passed through the feeder line 122, the drug delivery line 104, and the line segments and connection positioned therebetween only between vials that contain incompatible drugs. For example, the control system may allow an air bubble to pass through the bubble detector 128 and the occluder 130 toward the drug delivery line 104 if the control unit detects another vial of a different medication in the next drug channel. Thus in the exemplary method described above, an air bubble would be passed through the feeder line 122 associated with the Venofer® vial 116 and beyond the occluder 130 after delivery of the prescribed amount of Venofer® but no such air bubbles would be passed through the lines to the drip chamber when transitioning between the three Epogen® vials 118.

It has been found that having a relatively small inner diameter improves the ability of the air bubble to remove substantially all of the drug from the feeder lines and drug delivery line. In some implementations, the feeder lines 122, the drug delivery line 104, and the line segments and connectors therebetween have inside diameters of about 0.030 inch and outside diameters of about 0.125 inch. However, the lines and connectors can have different dimensions that are suitable for this process.

In certain implementations, the operating speed of the pump 132 is gradually increased as the quantity of drug in the vial 116, 118 from which the drug is being drawn decreases. As the quantity of drug in that vial decreases, a slight vacuum is produced in the vial. This vacuum can result in a decreased flow rate of the drug from the vial if the pump speed remains constant. Thus, gradually increasing the pump speed as the drug is drawn from the vial can help to maintain a substantially constant flow rate of the drug from the vial throughout the drug delivery process.

While certain implementations have been described, other implementations are possible.

While the top surfaces of the bi-stable members 148 have been illustrated as being substantially smooth, in certain implementations, each of the bi-stable members 148 is provided with a raised feature (e.g., a raised member) that extends from its top surface. The raised feature can help to ensure that the insertion of the drug vial into the drug vial recess of the drug vial spike 120 moves the bi-stable member 148 a sufficient distance into its associated aperture to cause the bi-stable member 148 to snap into the second position. The projection can, for example, be an elongate rod that has a sufficient length or height to ensure that the bi-stable member is pushed far enough down into its associate opening in the base 138 of the drug vial spike 120 to cause the bi-stable member to snap into the second position when the drug vial 116, 118 is fully inserted into the vial recess of the drug vial spike 120 (e.g., when the cap 119 of the drug vial 116, 118 contacts the base 138 of the drug vial spike 120).

While the surfaces of the leaf springs 152 that are contacted by the drug vial spike 120 when the drug vial 116, 118 is loaded onto the drug vial spike 120 have been illustrated as being substantially smooth, in certain implementations, a pointed projection extends from the surface of each leaf spring 152. The leaf spring 152 can provide sufficient resistance to deflection and the projections can be sufficiently pointed to dent the cap 119 of the vial 116, 118 into the rubber seal 123 when the operator presses the vial 116, 118 downward against the leaf springs 152 to load the drug vial 116, 118 onto the drug vial spike 120. In certain implementations, the leaf springs 152 each provide a resistance force of about 1 pound to about 20 pounds (e.g., about 1 pound to about 10 pounds, about 1 pound to about 5 pounds, about 5 pounds to about 10 pounds) prior to deflecting toward the base 138 of the drug vial spike 120.

While the drug vial spike 120 has been described as including leaf springs 152 to force the drug vial 116, 118 away from the base 138 of the drug vial spike 120 after insertion of the drug vial 116, 118, other types of springs, such as coil springs, can be used. The springs can be separate components that are attached to the drug vial spike (e.g., the base or side wall of the drug vial spike) or can be integrally formed with the drug vial spike (e.g., the base or side wall of the drug vial spike).

While the drug vial spike 120 has been described as including a flange that releasably holds the drug vial 116, 118, other temporary vial locking mechanisms or techniques including but not limited to clips, clamps, plastic friction slip fits, elastomeric cap fits, magnetic clamps, vial neck clips or clamps, vial body spring clips, bungee cords, etc. can be used.

Figure 10:
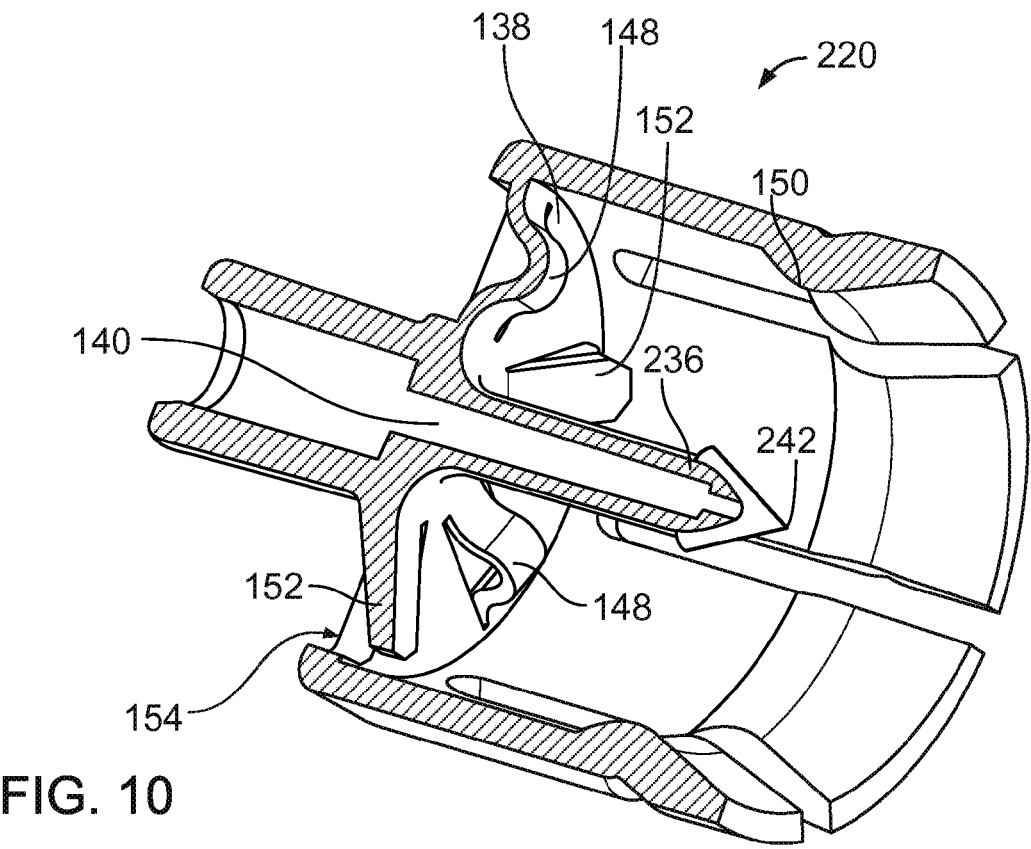
FIG. 10 is a cross-sectional view of a drug vial spike including a central spike with a conical tip.

While the central spike 136 of the drug vial spike 120 discussed above relies only on friction between its peripheral surface and the rubber seal 123 of the vial 116, 118 to pull the rubber seal 123 outward, other techniques are possible. In certain implementations, as shown in FIG. 10, a central spike 236 of a drug vial spike 220 includes an enlarged cone-shaped tip 242. After the conical tip 242 of the central spike 236 is inserted into the drug vial 116, 118 and the vial is pushed away from the drug vial spike 220 by the springs 152 extending from the base 138 of the drug vial spike 220, the conical tip 242 engages the inner surface of the rubber seal 123 of the vial 116, 118. This construction helps to ensure that the central portion of the rubber seal 123 is pulled away from the vial 116, 118 to create a depression along the inner surface of the rubber seal 123 of the inserted vial. As a result, this construction helps to ensure that all of the drug contained within the vial 116, 118 can be evacuated.

Figure 11:
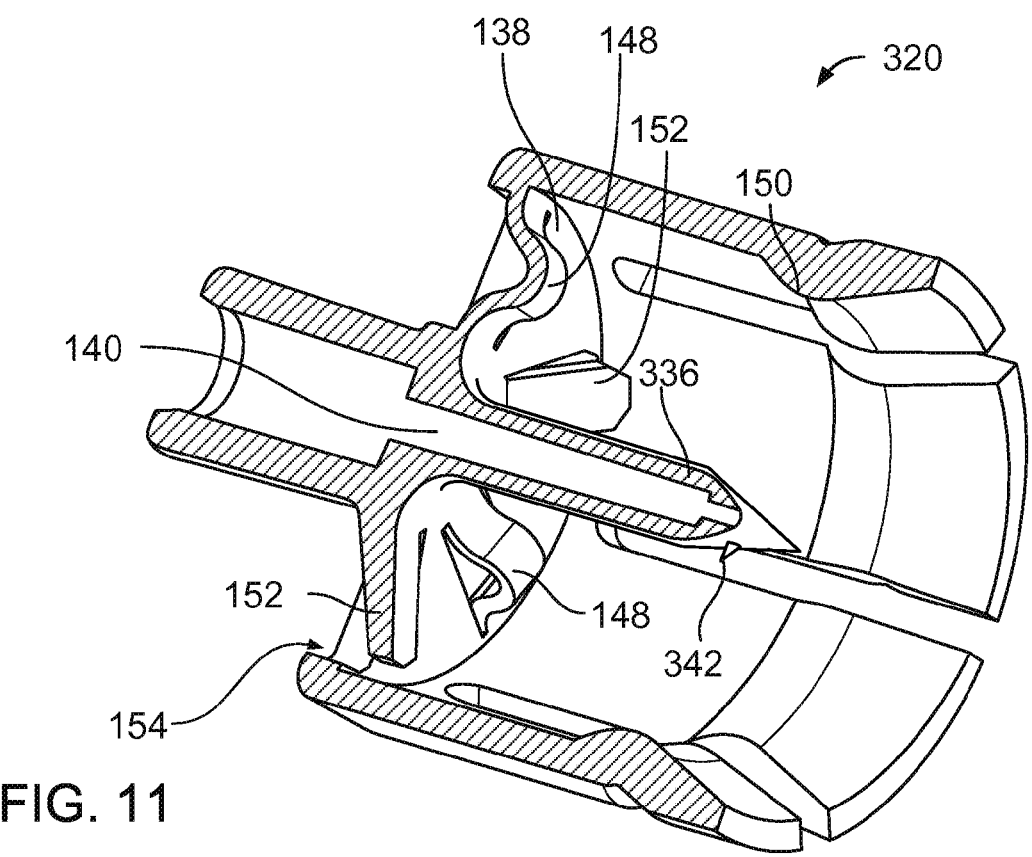
FIG. 11 is a cross-sectional view of a drug vial spike including a central spike with a barb.

While the enlarged tip 242 of the spike 236 has been described as being cone-shaped, enlarged features of any of various other shapes that allow the spike to pierce the rubber seal 123 of the vial 116, 118 and then engage the inner surface of the seal 123 can be used. In certain implementations, for example, as shown in FIG. 11, a central spike 336 of a drug vial spike 320 includes a barb 342 extending from its side surface.

As discussed above, circumferential sidewalls of the cup-shaped drug vial spikes 120, 220, 320 help to prevent the central spike 136, 236, 336 from being inadvertently contacted prior to its insertion into the vial 116, 118. Other spike protection devices can alternatively or additionally be used with any of the drug vial spikes described above. In certain implementations, the spikes of the above-described spike assemblies are provided with protective covers that can be removed prior to loading the drug vials onto the spikes. The covers can help to prevent the spikes from coming into physical contact with objects that might contaminate the spikes. For example, the covers can help to ensure that the user does not accidentally spike himself or herself while loading the drug vials onto the spikes. The covers can also help to prevent the spikes from puncturing the sterile bags in which the drug administration fluid line sets, which include the spikes, are provided to the user.

Figure 12:
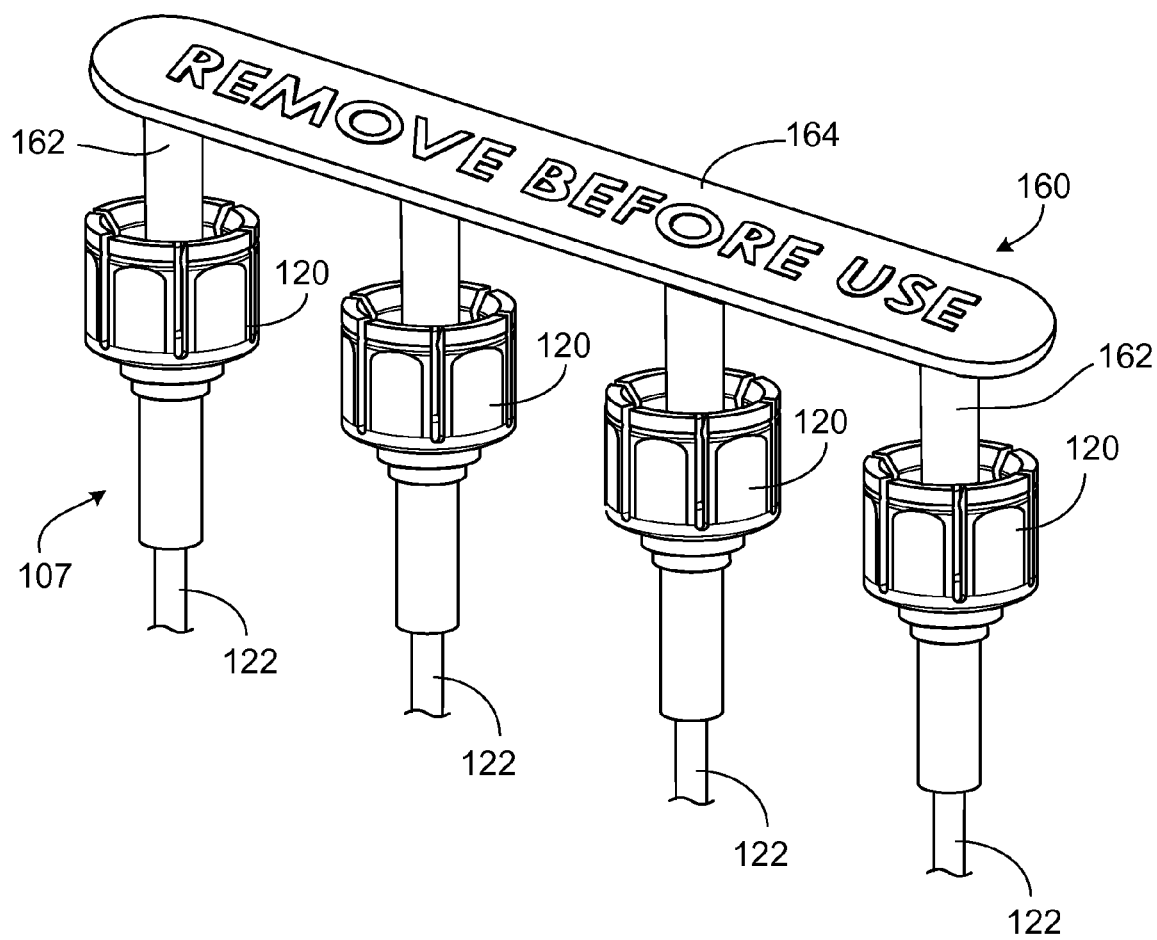
FIG. 12 is a perspective view a portion of the drug administration fluid line set illustrated in FIG. 1 with a spike cover disposed over the spikes of the drug administration fluid line set.

Referring to FIG. 12, one such spike cover 160 is a unitary plastic structure that includes tubular members 162 extending downward from an elongate structure 164. The tubular members 162 form cavities in which the multiple central spikes 136 of the drug vial spikes 120 of the drug administration fluid line set 107 are disposed prior to their insertion into the vials 116, 118. The cavities are sized and shaped so that the portions of the tubular members 162 forming those cavities grip their associated spikes 136 with sufficient force to prevent the cover 160 from falling off or being inadvertently knocked off the spikes 136 prior to loading the vials 116, 118 onto the spikes 136, while allowing the operator of the system to manually remove the cover 160 from the spikes 136 at the desired time. A lip or overhang extends around the circumference of the elongate member 164 of the cover 160 to allow the operator to easily grasp the cover 160 for removal from the spikes 136. As an alternative to or in addition to this lip or overhang, the cover 160 can include a tab extending from one end to allow the user to sequentially peel the cover 160 away from the spikes.

While the drug administration fluid line set 107 has been described as including multiple feeder lines 122 that connect to the main drug delivery line 104 via T-connectors 124 and line segments 126, other arrangements are possible. In some implementations, for example, the feeder lines 122 are welded or adhesively bonded to the drug delivery line 104 in a manner such that drug can be fed directly from the feeder lines 122 into the drug delivery line 104. Alternatively, the feeder lines 122 and the drug delivery line 104 can be integral with one another to achieve the same effect.

Figure 13:
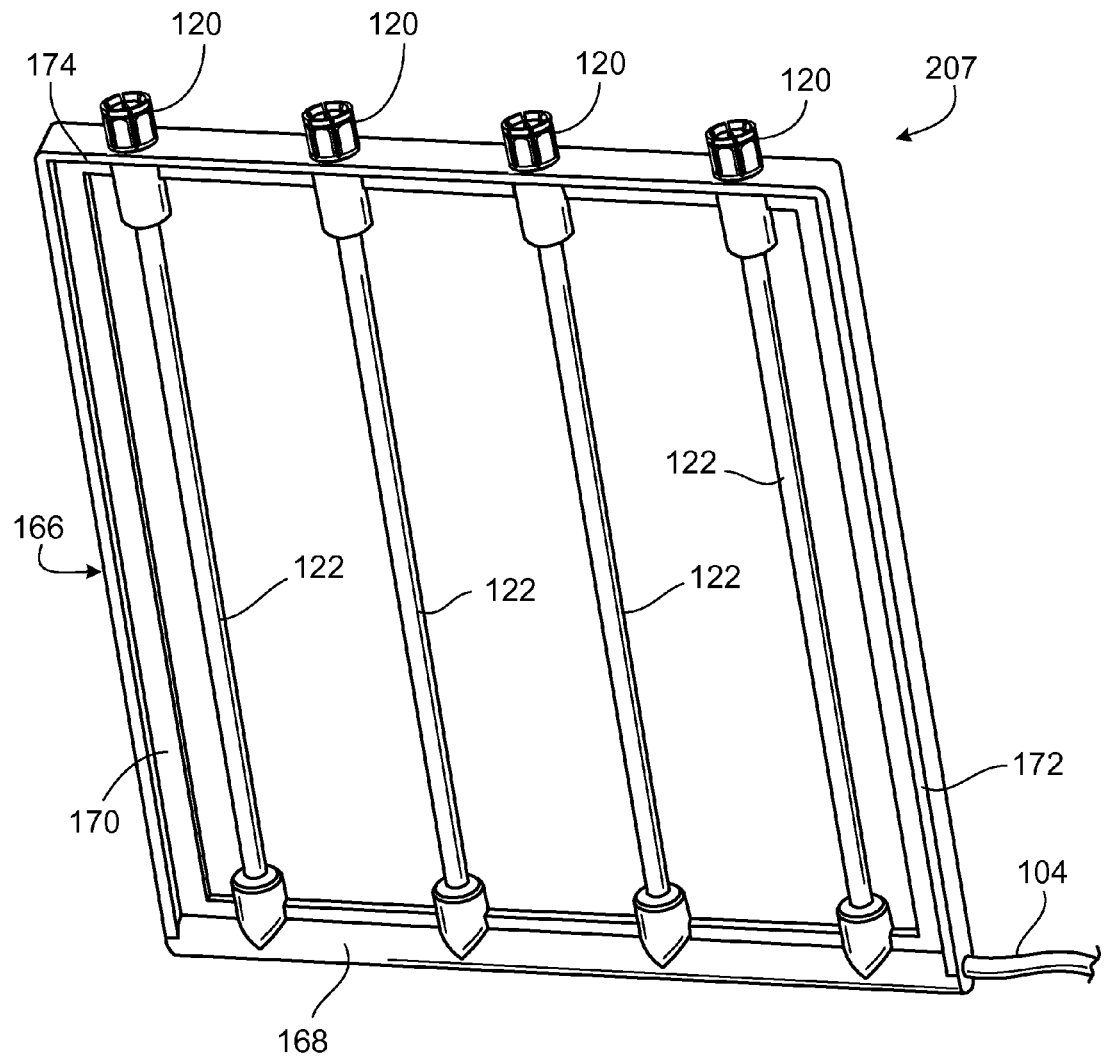
FIG. 13 is a perspective view of a drug administration fluid line set that includes a frame that holds fluid lines of the drug administration fluid line set in a spaced configuration.

FIG. 13 shows a slightly modified drug administration fluid line set 207 in which the feeder lines 122 are retained in a spaced apart configuration by a frame 166. The frame 166 includes along its bottom edge a manifold 168 that functions in a manner similar to the T-connectors 124 and line segments 126 illustrated above in FIG. 2, two side support members 170, 172 that extend from the manifold 168, and a top support member 174 that extends between the two side support members 170, 172. The side support members 170, 172 are attached (e.g., thermally bonded, adhesively bonded, or mechanically attached) at their bottom and top ends to the manifold 168 and top support member 174, respectively. The feeder lines 122 similarly extend between and are attached (e.g., thermally bonded, adhesively bonded, or mechanically attached) to the manifold 168 and top support member 174.

The manifold 168, side support members 170, 172, and top support member 174 are typically formed of one or more materials that are more rigid than the material or materials from which the feeder lines 122 are made. In certain implementations, the manifold 168, side support members 170, 172, and top support member 174 are formed of polycarbonate or AMS. However, other relatively rigid materials can alternatively or additionally be used. Due to the construction and materials of the frame 166, the frame 166 is sufficiently rigid to maintain its general rectangular shape, and is thus capable of maintaining the feeder lines 122 in substantially fixed positions relative to one another.

Still referring to FIG. 13, the drug vial spikes 120 are secured to the top support member 174 of the frame 166. The drug vial spikes 120 can, for example, be thermally bonded, adhesively bonded, or mechanically attached to the top support member 174. The feeder lines 122 are in fluid communication with their associated drug vial spike 120 and with a central passage that extends along the length of the manifold 168. Thus, when the central spikes 136 of the drug vial spikes 120 penetrate the rubber seals 123 of the vials 116, 118, drugs can flow through the feeder lines 122 and into the central passage of the manifold 168. The drug delivery line 104 is similarly connected to the manifold 168 and is in fluid communication with the central passage of the manifold 168. As a result, during use, drugs can travel from the vials 116, 118 to the drug delivery line 104 and ultimately to the drip chamber 106 of the blood circuit where the drugs mix with the patient's blood.

Because the frame 166 holds the feeder lines 122 in substantially fixed positions relative to one another, loading of the above-described drug administration fluid line set 207 is simplified. For example, after loading one of the feeder lines 122 into its associated components (e.g., air bubble detector 128 and occluder 130) on the drug delivery device 130, the remaining feeder lines 122 will be generally aligned with their associated components of the drug delivery device 103 due to the rigidity of the frame 166. Thus, the operator can more easily load the remaining feeder lines 122 into their associated drug delivery device components without having to first identify and untangle those feeder lines.

While the drug delivery device 103 described above includes a single drug pump 132 and multiple occluders 130 that are operated in a manner to control drug flow from the feeder lines 122 to the drug delivery line 104, other arrangements for controlling the drug flow can be used. In certain implementations, for example, each of the feeder lines 122 can be connected to (e.g., threaded through) its own associated pump (e.g., a peristaltic pump). In some such implementations, the drug delivery device 103 does not include a pump connected to the drug delivery line 104 and does not include separate occluders for occluding the feeder lines 122. Rather, the pumps of the drug delivery device, which are connected to the feeder lines 122, can be individually operated to selectively draw the drug from its associated vial 116, 118 and to occlude its associated feeder line 122 when the pump is not in operation.

While methods of using the drug delivery device 103 have described in which the drug vials 116, 118 are manually pressed onto the central spikes 136, 236, 336 of the drug vial spikes 120, 220, 320 so that the central spikes 136, 236, 336 pierce the rubber seals 123 of the vials 116, 118, the drug delivery device 103 can alternatively or additionally be equipped with one or more moveable drug vial holders so that the drug vials 116, 118 can be automatically loaded onto the drug vial spikes 120, 220, 320. The drug delivery device 103 can, for example, include vial holders that are moveable relative to the drug vial spikes 120, 220, 320 such that the vial holders and the vials 116, 118 contained therein can be moved (e.g., moved downward) relative to the drug vial spikes 120, 220, 320 causing the central spikes 136, 236, 336 to pierce the rubber seals 123 of the vials 116, 118. In certain implementations, the vial holders are configured to be moved manually. The vial holders can, for example, be connected to a mechanism that permits a user to simultaneously spike all of the vials 116, 118 (e.g., by manipulating a lever of the mechanism). Movement of the vial holders can alternatively or additionally be automated. The mechanism for moving the vial holders relative to the drug vial spikes 120, 220, 320 can, for example, be connected to one or more motors that can be operated to move the vial holders and vials 116, 118 therein relative to the drug vial spikes 120, 220, 320.

Similarly, while the drug delivery system 102 has been described as including drug vial spikes 120, 220, 320 that are configured to cause the vials 116, 118 to be forced in the upward direction after the vials 116, 118 are loaded onto the drug vial spikes 120, 220, 320 and/or as including pointed projections that form dents in the caps 119 of the vials 116, 118 in order to inhibit the rubber seals 123 of the drug vials from bulging inwardly into the vials 116, 118 during the spiking process, other mechanisms for inhibiting inward bulging of the rubber seals of drug vials can be used. The drug delivery device can, for example, include vial holders that have top and bottom members that are configured to hold a vial therebetween and that are moveable relative to one another such that the vial can be compressed between the top and bottom members. The rubber seal positioned between the neck portion and cap of the vial is compressed as the top and bottom members are moved toward one another. It has been found that a sufficient compressive force can be applied to the rubber seal using this technique to substantially prevent the rubber seal from bulging inwardly into the body of the vial when the rubber seal is pierced by its associated spike. In certain implementations, the drug delivery device 103 is equipped with vial holders that are configured to move relative to associated drug vial spikes and include top and bottom members that are moveable relative to one another to allow the vials 116, 118 to be compressed therebetween. Such vial holders can be operated in two stages. During the first stage, the top and bottom members of the vial holders are moved together to compress the vials 116, 118 therebetween, and during the second stage, the vial holders are moved relative to the spikes to cause the associated drug vial spikes to pierce the rubber seals 123 of the vials 116, 118.

While the drug delivery device 103 has been described as including a control unit that can control various functions of the drug delivery device 103, in certain implementations, the drug delivery device is instead connected to a control unit of the hemodialysis machine, which is programmed to cause the drug delivery device to operate in the manner described above. Similarly, while the drug delivery device 103 has been described as including a user interface that can be used to enter information, such as prescribed drug dosages, into the drug delivery device 103, in certain implementations, the drug delivery device includes no such user interface and instead a user interface of the hemodialysis machine to which it is attached is used to enter the information required for operating the drug delivery device.

Figure 14:
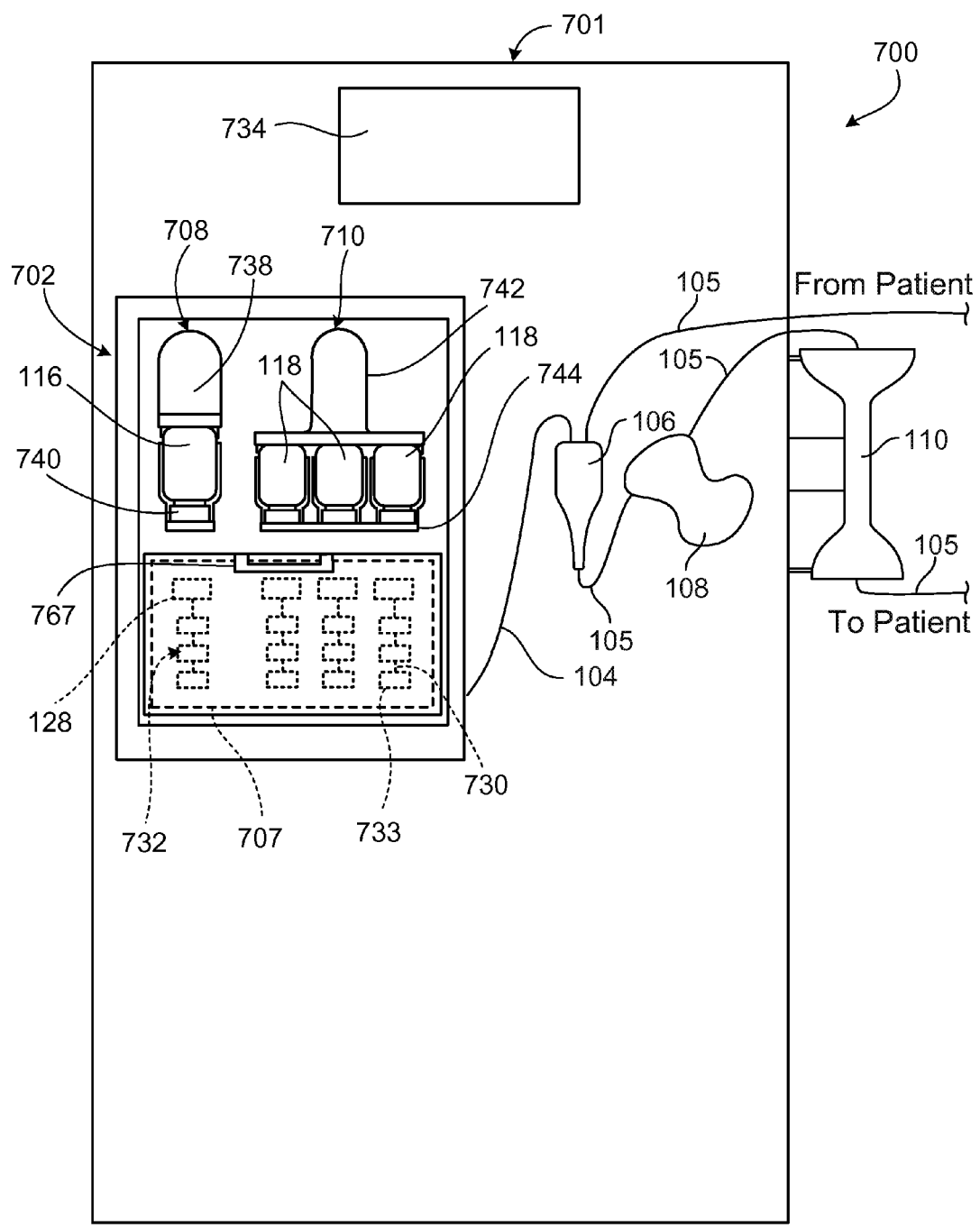
FIG. 14 is a front view of a hemodialysis system that includes a hemodialysis machine with a different type modular drug delivery device integrated therein. A drug administration fluid line cassette and drug vials are secured between a door and inner face of the modular drug delivery device.

FIG. 14 illustrates another hemodialysis system 700 that includes a drug delivery system 702 for delivering drugs, such as Epogen® and Venofer®, to the blood circuit connected to a hemodialysis machine 701. The drug delivery system 702 includes a modular drug delivery device 703 that is attached to and exposed on the face of the hemodialysis machine 701 and a disposable drug administration fluid line set (also referred to herein as a drug administration fluid line cassette) 707 that is connected to the drug delivery device 703. The disposable drug administration fluid line cassette 707, which is similar to the drug administration fluid line set described with respect to FIG. 13, is disposed in a cassette compartment formed between a door 704 and an inner face of the drug delivery device 703 and is used to transport the drugs from the drug vials 116, 118 to the drip chamber 106 of the blood circuit connected to a hemodialysis machine 701.

Figure 15:
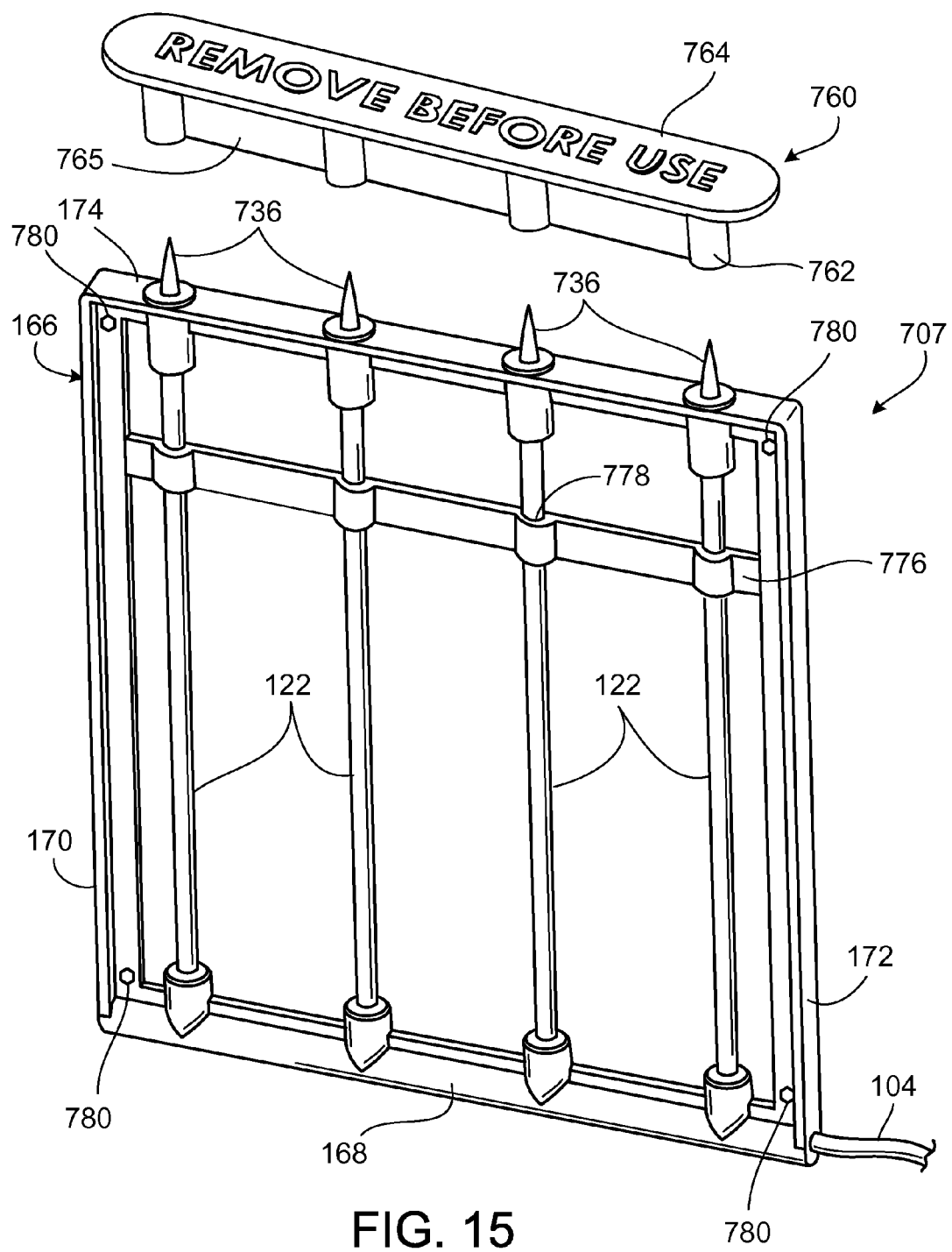
FIG. 15 is a perspective, exploded view of the drug administration fluid line cassette that is partially illustrated in FIG. 14 and a spike cover that is disposed over spikes of the drug administration fluid line cassette prior to use.

FIG. 15 illustrates the drug administration fluid line cassette 707 with its protective spike cover 760 removed from its spikes 736. As shown, the feeder lines 122 are retained in a spaced apart configuration by the frame 166 of the cassette 707. In addition to the frame 166, which includes the manifold 168, the two side support members 170, 172, and the top support member 174, the cassette 707 includes a crossbar 776 that extends between the two side support members 170, 172. The crossbar 776 includes recessed regions 778 into which the feeder lines 122 are received and retained. In addition, hexagonal holes 780 are provided in the front surface of the cassette 707 (i.e., the surface of the cassette 707 that contacts the inner surface of the door 704 of the drug delivery device 703 when the cassette 707 is loaded in the cassette compartment of the drug delivery device 703). As described below, these holes 780 mate with hexagonal projections 706 extending from the inner surface of the door 704 to secure the cassette 707 to the door 704 during use and to help ensure that only appropriate cassettes (e.g., cassettes intended for use with the drug delivery device 703 by the drug delivery device manufacturer) are used with the drug delivery device 703.

Still referring to FIG. 15, the spikes 736 are attached (e.g., thermally bonded, adhesively bonded, and/or mechanically attached) to and extend upward from the top support member 174 of the cassette 707. The spikes 736 can have a construction similar to the construction of the central spikes 136 described above with respect to the drug vial spikes 120. For example, each of the spikes 736 can include a central channel that extends along the length of the spike and two openings (e.g., channels or slots) along the outer surface of the spike that lead to the central channel. The central channel of each spike is aligned with and fluidly connected to a vertical passage extending through the top support member 174.

The feeder lines 122 are in fluid communication with their associated spikes 736 via the vertical passages extending through the top support member 174. The feeder lines are also in fluid communication (via openings in the top surface of the manifold 168) with the central passage that extends through the manifold 168. The drug delivery line 104 is similarly connected to the manifold 168 and is in fluid communication with the central passage of the manifold 168. Thus, when the spikes 736 penetrate the rubber seals 123 of the vials 116, 118 during use, drug can flow through the feeder lines 122, the manifold 168, the drug delivery line 104, and into the drip chamber 106.

The manifold 168, the side support members 170, 172, the top support member 174, and the crossbar 776 are typically formed of one or more materials that are more rigid than the material or materials from which the feeder lines 122 are made. Examples of such relatively rigid materials include polycarbonate and AMS. However, other relatively rigid materials can alternatively or additionally be used. Due to the construction and materials of the frame 166 and cross bar 776 of the cassette 707, the feeder lines 122 are held in substantially fixed positions relative to one another. As a result of this configuration, loading of the drug administration fluid line cassette 707 into the cassette compartment of the drug delivery device 703 is simplified.

Still referring to FIG. 15, the spike cover 760 includes multiple tubular members 762 that extend from a top structure 764. The various tubular members 762 are interconnected by wall segments 765 that provide the spike cover 760 with added rigidity. The spike cover 760 is used in the same manner as the spike cover 160 described above with respect to FIG. 12. The spike cover 760 is removed form the spikes 736 of the cassette 707 prior to loading the vials 116, 118 onto the spikes 736.

Referring again to FIG. 14, which illustrates the cassette 707 in the cassette compartment of the drug delivery device 703, the spikes 736 of the cassette 707 have been inserted into the vials 116 and 118, which are retained in vial holders 708 and 710, respectively. Peristaltic pumps 732 extend from the inner face of the drug delivery device 703 and align with the feeder lines 122 (between the cross bar 776 and the manifold 168 of the cassette 707) such that when one of the pumps 732 is operated, the drug is drawn from the vial 116, 118 associated with that pump and delivered via the feeder lines 122, the manifold 168, and the drug delivery line 104 to the drip chamber 106 of the blood circuit.

Figure 16:
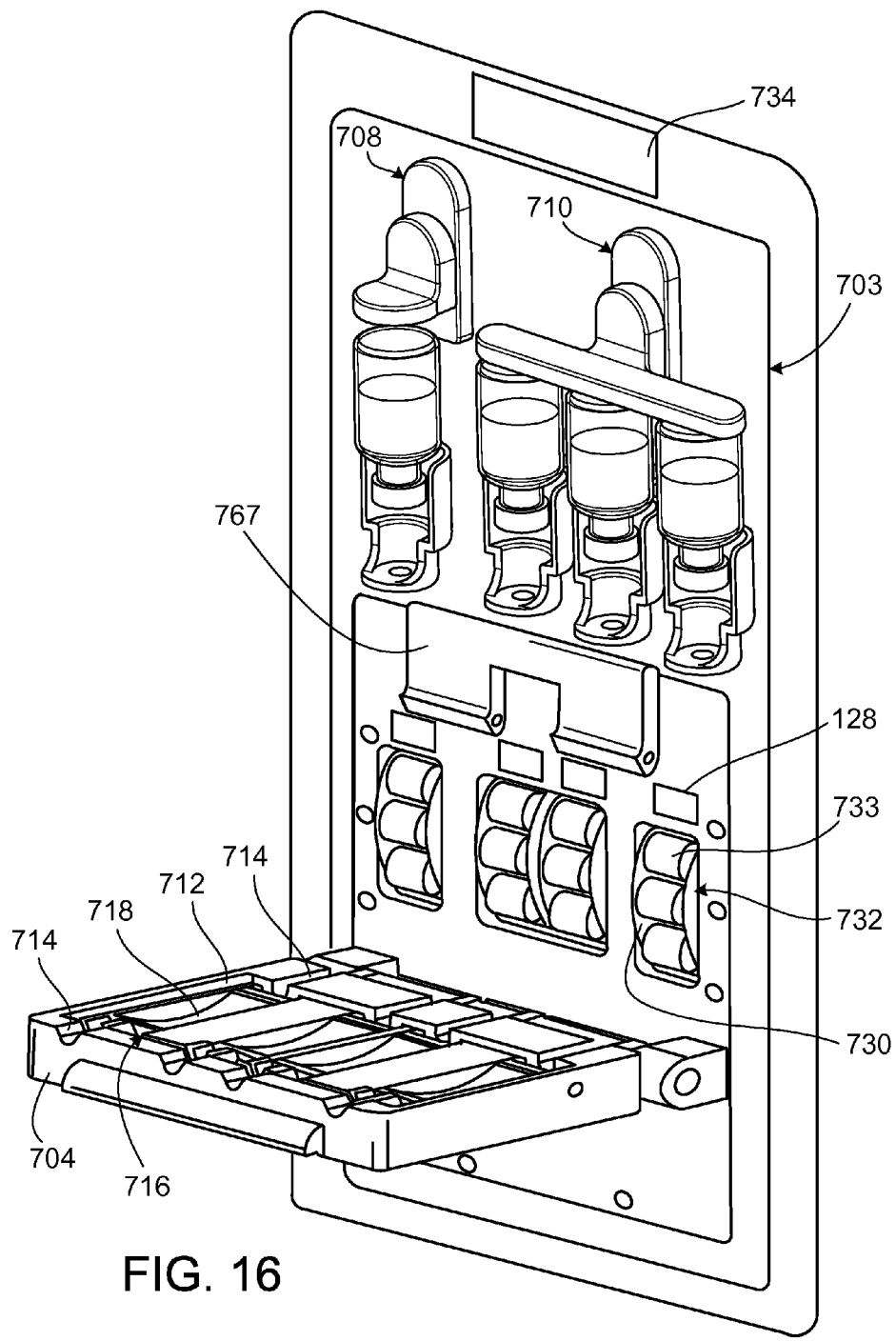
FIG. 16 is a perspective view of the hemodialysis machine of FIG. 14 with the door of the drug delivery device opened and the drug administration fluid line cassette and vials removed to expose various components of the drug delivery device.

FIG. 16 illustrates the drug delivery device 703 with the door 704 opened and the drug administration fluid line cassette 707 removed. As shown, the inner surface of the door 704 includes a recessed region 712 that is configured to receive the rigid frame 166 of the cassette 707 and elongate slots 714 that are configured to receive the feeder lines 122 of the cassette 707 without substantially deforming the feeder lines 122. In certain implementations, the recessed region 712 and slots 714 are sized so that the frame 166 and feeder lines 122 of the cassette 707 can be snapped into the recessed region 712 and slots 714, respectively, and thus releasably secured to the door 704. The inner surface of the door 704 also includes the hexagonal projections 706 that are configured fit into the hexagonal holes 780 formed in the cassette 707 when the cassette 707 is loaded into the door 704. The hexagonal projections 706 can be sized and shaped to create a snap fit or a snug press fit that secures the drug administration fluid line cassette 707 to the door 704.

In addition, the inner surface of the door 704 includes spring-loaded members 716 that define recesses or raceways 718 that receive roller members of the peristaltic pumps 732 of the drug delivery device 703 when the door 704 is closed. Springs are connected to top and bottom regions of each member 716 and to an internal fixed member in the door 704 to allow the members 716 to flex in response to contact with the rollers of the peristaltic pumps 732 or in response to contact with the feeder lines 122 positioned between the members 716 and the rollers of the peristaltic pumps 732.

Still referring to FIG. 16, the peristaltic pumps 732 are positioned in a spaced configuration across the face of the drug delivery device 703. Each peristaltic pump 732 includes a rotatable frame 730 and multiple rollers 733 rotatably positioned around the circumference of the frame. The peristaltic pumps 732 are configured to rotate about an axis that extends in a direction that is substantially parallel to the face of the drug delivery device 703. When the cassette 707 is positioned in the cassette compartment between the inner face of the drug delivery device 703 and the closed door 704, the feeder lines 122 align with the pumps 732 and are thus pressed into the raceways 718 of the spring-loaded members 716 in the door 704. The spring force provided by the springs of the spring-loaded members 716 help to take up tolerance between the raceways 718 and the rollers 733 and thus help to ensure that a fixed compression force is applied to the feeder lines positioned between the raceways 718 and the rollers 733. During operation of the pumps 732, the rollers are rotated from top to bottom (in the view show in FIG. 16) and thus force pillows of fluid downward through the associated feeder lines 122. This draws a vacuum on the associated vial 116, 118 causing drug to be drawn into the feeder lines 122 from the vials 116, 118.

The spacing of the rollers 733 about the circumference of the rotatable frame 730 of the peristaltic pumps 732 is selected so that at least one of the rollers 733 is positioned in the raceway 718 of the associated spring-loaded member 716 when the door 704 of the drug delivery device 703 is closed. This helps to ensure that the feeder lines 122 positioned between the pumps 732 and the raceways 718 are always occluded in at least one location and thus helps to prevent the drugs from passing through the feeder lines 122 to the manifold 168 when the pumps 732 are not in operation.

In certain implementations, the springs that connect the members 716 to the internal structure of the door 704 can be adjusted or replaced to change the force applied to the rollers of the peristaltic pumps 732 during operation of the pumps 732. The relatively easy accessibility to the door 704 of the drug delivery device 703 can facilitate this process. In addition, spring loading the raceway members 716 rather than the peristaltic pumps 732 themselves can simplify the design of, and thus reduce the manufacturing cost of, the drug delivery device 703.

Figure 17:
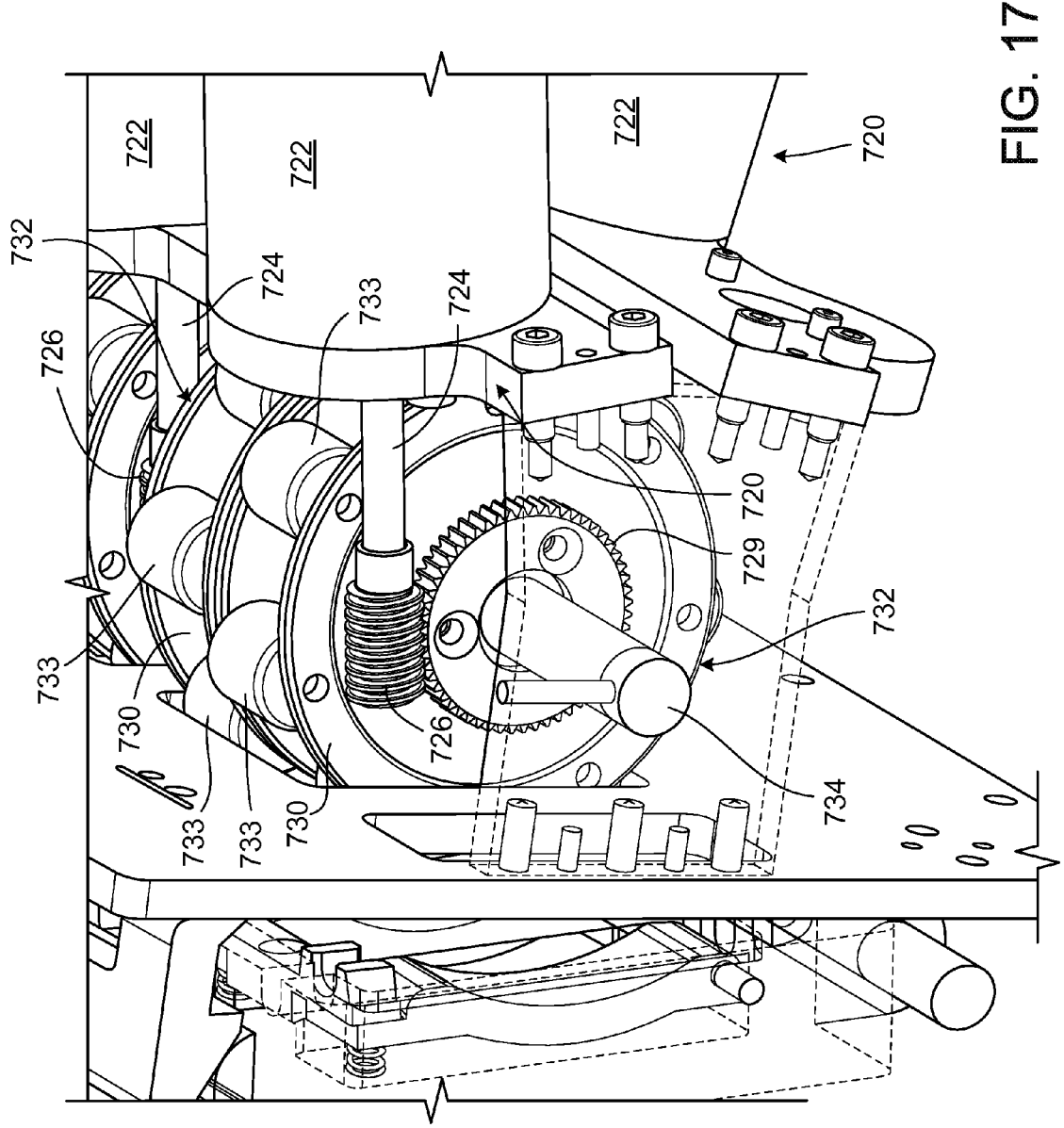
FIG. 17 is a perspective view of certain components of the drug delivery device of FIG. 14, including peristaltic pumps and their drive mechanisms.

FIG. 17 shows drive mechanisms 720 of the peristaltic pumps 732. Each of the drive mechanisms includes an electric motor 722 having an output shaft 724. A worm gear 726 is positioned on the end of the output shaft 724 and is configured to engage a gear 729 that is secured to the frame 730 of the associated peristaltic pump 732. To drive the peristaltic pump 732, electrical power is supplied to the motor 722, causing the output shaft 724 and the worm gear 726 attached thereto to rotate. The engagement of the worm gear 726 with the gear 729 of the frame 730 causes the frame 730 and the rollers 733 attached thereto to rotate about a fixed support rod 734. Because each peristaltic pump 732 has its own drive mechanism 720, the peristaltic pumps 732 can be independently operated such that drug can be drawn from one drug vial 116, 118 at a time. The speed of the peristaltic pumps 732, and thus the rate at which the drugs are withdrawn from the vials 116, 118, can be altered by altering the power or voltage supplied to the motors 722.

Referring again to FIG. 16, bubble detectors 128, which were described in greater detail above, are also arranged in a spaced configuration across the inner face of the drug delivery device 703 above the peristaltic pumps 732. As discussed above, the bubble detectors 128 are capable of detecting air bubbles within the feeder lines 122 and can thus be used to determine whether the drug vial 116, 118 associated with a particular feeder line 122 is empty during treatment.

The drug vial holder 708 of the modular drug delivery device 703 is configured to hold a single Venofer® vial 116, and the drug vial holder 710 is configured to hold up to three Epogen® vials 118. The drug vial holder 708 includes a top member 738 and a bottom member 740 that can retain the single Venofer® vial 116 therebetween. The bottom member 740 has a top surface on which the cap of the inverted Venofer® vial 116 can rest. In certain implementations, the bottom member 740 includes a recess that is sized and shaped to receive the cap 119 (or a portion of the cap 119) of the vial 116. This recess can help to ensure that the vial 116 is properly positioned in the vial holder 708. The bottom member 740 of the drug vial holder 708 also defines a through opening that allows an associated spike 736 of the drug administration fluid line cassette 707 to pass through the bottom member 740 and pierce the rubber seal 123 of the Venofer® vial 116 during use.

The top and bottom members 738, 740 of the drug vial holder 708 are moveable relative to one another such that a drug vial can be compressed therebetween. In addition, the drug vial holder 708 as a whole is moveable in the vertical direction relative to the inner face of the drug delivery device 703 and relative to an associated spike 736 of the drug administration fluid line cassette 707 when the cassette 707 is disposed in the cassette compartment of the drug delivery device 703. As a result, when the cassette 707 is disposed in the cassette compartment, the top and bottom members 738, 740 of the drug vial holder 708 can be moved in unison along with the Venofer® vial 116 to cause the associated spike 736 of the cassette 707 to pierce the rubber seal 123 of the vial 116.

The drug vial holder 710, which holds the Epogen® vials 118 during use, is similar to the drug vial holder 708 described above. In particular, this drug vial holder 710 also includes top and bottom members 742, 744 between which three Epogen® vials 118 can be held, and the bottom member 744 defines three openings through which spikes 736 of the cassette 707 can pass to pierce the rubber seals 123 of the vials 118. In some implementations, the upper surface of the bottom member 744 defines recesses that receive the caps 119 of the Epogen® vials 118 and help to ensure that the vials 118 are properly positioned in the vial holder 710. These recesses can, for example, help to ensure that the vials 118 are aligned with the openings in the bottom member 744 to allow the spikes 736 of the cassette 707 to pierce the rubber seals 123 of the vials 118.

Figure 18:
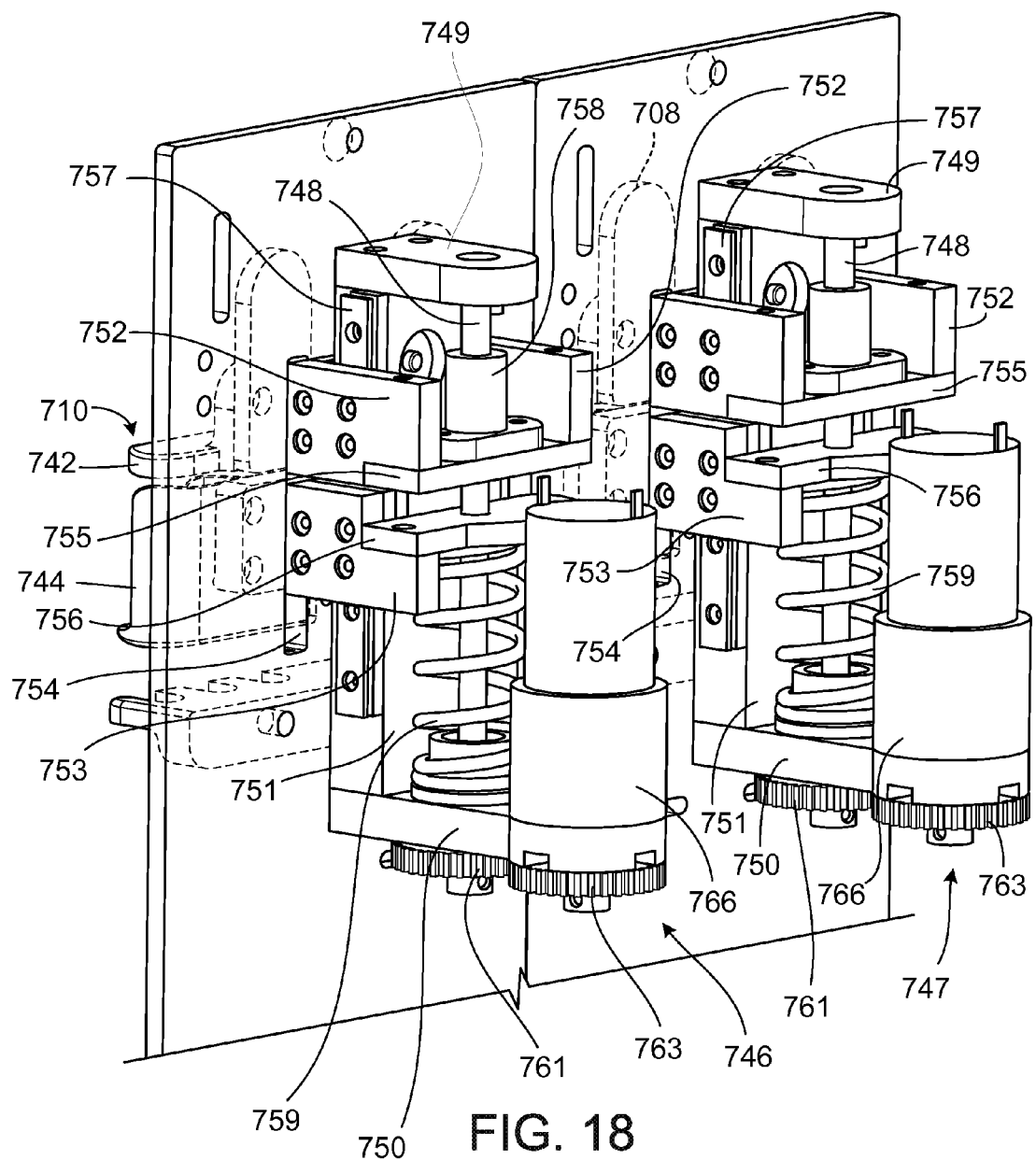
FIG. 18 is a perspective view of drive mechanisms that are used to operate drug vial holders of the drug delivery device of FIG. 14.

FIG. 18 shows drive mechanisms 746 and 747 that can be used to operate the drug vial holders 710 and 708, respectively. The drive mechanism 746 can move the top and bottom members 742, 744 of the drug vial holder 710 in order to clamp or compress the rubber seals 123 of the Epogen® vials 118 between their caps 119 and neck portions 121 and to cause the spikes 736 of the drug administration fluid line cassette 707 to pierce the rubber seals 123 of the vials 118. Similarly, the drive mechanism 748 can move the top and bottom members 738, 740 of the drug vial holder 708 in order to clamp or compress the rubber seal 123 of the Venofer® vial 118 between its cap 119 and neck portion 121 and to cause one of the spikes 736 of the cassette 707 to pierce the rubber seal 123 of the vial 118. The drive mechanisms 746, 747 are positioned within the housing of the hemodialysis machine 701 behind the inner face of the drug delivery device 703. Thus, the drive mechanisms 746, 747 would not typically be visible to the user. Because the drive mechanisms 746, 747 have generally the same structure and function, we only describe the structure and function of the drive mechanism 746 in detail.

Still referring to FIG. 18, the drive mechanism 746 includes a drive shaft 748 that is rotatably disposed within bores in top and bottom supports 749, 750 that are fixed to the face or housing of the drug delivery device 703. The top and bottom end regions of the drive shaft 748 can, for example, be connected to the top and bottom supports 749, 750 by bearings (e.g., ball bearings) that allow the drive shaft 748 to rotate with respect to the top and bottom supports 749, 750. At least a top region of the drive shaft 748 is threaded. A vertical support wall 751 is fixed at its top and bottom ends to the top support 749 and bottom support 750, respectively. The vertical support wall 751 is fixed relative to the face or housing of the drug delivery device 703.

Top and bottom member extensions 752 and 753 extend from the rear of each of the top and bottom members 742 and 744, respectively, of the drug vial holder 710, near right and left end regions of those top and bottom members 742, 744. The top and bottom member extensions 752, 753 pass through vertical slots 754 in the face of the drug delivery device 703 and are thus free to move up and down with respect to the face of the drug delivery device 703. As a result, the top and bottom members 742, 744 of the drug vial holder 710 are allowed to move up and down with respect to the face of the drug delivery device 703. A cross bar 755 extends horizontally between the two top member extensions 752 and is attached in opposite end regions to those extensions 752. Similarly, a cross bar 756 extends horizontally between the two bottom member extensions 753 and is attached in opposite end regions to those extensions 753. Each of the cross bars 755, 756 includes a hole through which the drive shaft 748 passes. The holes typically have larger diameters than the outer diameter of the drive shaft 748 such that the cross bars 755, 756 can move vertically along the drive shaft 748 without contacting the drive shaft 748.

The inside surfaces (i.e., the surfaces facing the drive shaft 748) of the top and bottom member extensions 752, 753 include vertical channels that are configured to receive linear guides 757 that extend from opposite side surfaces of the vertical support wall 751. This arrangement helps to ensure that the two top member extensions 752 remain substantially level with one another and remain substantially perpendicular to the face of the drug delivery device 703 as those extensions move up and down along the slots 754. The same effect is achieved with respect to the two bottom member extensions 753. The linear guides 757 can be formed of a low-friction material, such as polyoxymethylene (marketed under the tradename Delrin and available from Dupont of Wilmington, Del.), in order to reduce the resistance applied to the sliding top and bottom member extensions 752, 753.

Still referring to FIG. 18, a drive member (e.g., ball screw) 758 is attached to the top cross bar 755 in a manner such that the drive member 758 is substantially prevented from moving vertically or rotationally relative to the cross bar 755. The drive member 758 includes a central passage with threads that are configured to engage threads of the top threaded region of the drive shaft 748. The engagement of these threads in combination with the substantial inability of the drive member 758 to rotate with respect to the drive shaft 748 causes the drive member 758 to move vertically along the drive shaft 748 as the drive shaft 748 is rotated. Whether the drive member 758 moves up or down along the drive shaft 748 depends on the direction of rotation of the drive shaft 748. Because the drive member 758 is fixed to the cross bar 755, which is fixed to the top member extensions 752, which are attached to the top member 742 of the vial holder 710, rotation of the drive shaft 748 can move the top member 742 of the vial holder 710 up and down with respect to the face of the drug delivery device 703.

As discussed above, both the top member extensions 752 and the bottom member extensions 753 ride along the linear guides 757. The top and bottom member extensions 752, 753 are positioned such that, when the vials 118 are disposed in the vial holder 710, the top and bottom member extensions 752, 753 will not contact one another even as the top member extensions 752 are moved downward. At some point, as the top member extensions 752 move downward relative to the bottom member extensions 753, the top member 742 of the drug vial holder 710 will contact the vials 118 and the vials 118 will be compressed between the top and bottom members 742, 744 of the drug vial holder 710.

A spring 759 is disposed between and attached to the bottom cross bar 756 and the bottom support 750. As the top member 742 of the drug vial holder 710 is moved downward toward the bottom member 744 and contacts the bottom surfaces (facing up) of the inverted vials 118, a force is applied to the spring 759. The spring force coefficient is selected so that this force does not initially permit the bottom member 744 of the drug vial holder 710 to move downward. Instead, the downward movement of the top member 742 causes the rubber seals 123 of the vials 118 to be compressed between the caps 119 and neck portions 121 of the vials 118. To achieve this effect, the spring 759 has a spring force coefficient that is greater than a collective spring force coefficient of the rubber seals 123 of the vials 118. In certain implementations, the spring is configured to provide a resistance force of about 1 pound to about 20 pounds (e.g., about 1 pound to about 10 pounds, about 1 pound to about 5 pounds, about 5 pounds to about 10 pounds). The compression of the rubber seals 123 between the caps 119 and neck portions 121 of the vials 118 inhibits movement of the rubber seal 123 relative to the caps 119 and neck portions 121 of the vials 118. This can advantageously inhibit or prevent the rubber seals 123 from bulging into the vials as the spikes 736 of the drug administration fluid line cassette 707 pierce the rubber seals 123. This spiking technique is described in greater detail below.

A gear 761 is attached to a bottom end region of the drive shaft 748. This drive shaft gear 761 is engaged with a gear 763 that is connected to an output shaft of a motor (e.g., an electric motor) 766. When the motor 766 is operated, the output shaft and the gear 763 connected thereto rotate. This causes the drive shaft gear 761 and the drive shaft 748 to rotate. As a result, operation of the motor 766 can be used to move the top member 742 of the drug vial holder 710 relative to the bottom member 744 of the drug vial holder 710 and, after compressing the vials 118 between the top and bottom members 742, 744, to move the top and bottom members 742, 744 and the vials 118 therebetween in unison relative to the spikes 736 of the drug administration fluid line cassette 707, which is substantially fixed relative to the face of the drug delivery device 703.

Referring again to FIGS. 14-16, the drug vial holders 708, 710 of the drug delivery device 703 can be equipped with any of the various types of sensors described above for sensing the presence of a vial, identifying the type drug vial installed, detecting the size of the drug vials, and/or detecting the mass of the drug vials.

The drug delivery device 703 also includes a control unit similar to the control unit described above with respect to the drug delivery device 103. The control unit can power and control the various components of the drug delivery device 703, including the bubble detectors 128, the drug pumps 732, and the various sensors. For example, the control unit can control the pumps 732 to ensure that only one of the pumps 732 is in operation at a time. This helps to ensure that drug is pulled from only one of the vials 116, 118 at a time during treatment. Upon determining that the prescribed volume of the drug has been delivered (based on monitoring the operation of the pumps 732), the control unit can turn off the pump 732 associated with that drug vial 116, 118 and turn on the pump 732 associated with the drug vial 116, 118 containing the next drug to be delivered. In addition, after the full contents of a vial have been evacuated, air will be sucked into the feeder line 122 associated with that vial and will be detected by the bubble detector 128. In response, the control unit can turn off the pump 732 associated with the empty vial and turn on the pump 732 associated with the vial containing the next drug to be delivered.

In addition, upon receiving signals from the drug vial ID sensors that do not match the inputted treatment information, an alarm (e.g., an audible and/or visual alarm) can be activated. Alternatively or additionally, the drug delivery device 103 can be configured so that treatment cannot be initiated until the sensors detect the correct combination of vials.

Like the drug delivery device 103, the drug delivery device 703 is configured to sense if the blood pump 108 of the dialysis machine 701 is running and to pause drug delivery if the blood pump 108 is stopped. This technique prevents 'pooling' of the delivered drug in the drip chamber 106.

Still referring to FIGS. 14-16, a method of using the hemodialysis system 700 to perform hemodialysis on a patient will now be described. Prior to beginning the hemodialysis treatment, the various lines and passages that make up the blood circuit and dialysate circuit of the hemodialysis machine 701 are primed, and then the patient lines 105 are connected to the patient. The hemodialysis treatment is then initiated by activating the blood pump 108 and dialysate pump of the dialysis machine 701 to circulate blood and dialysate through the blood and dialysate circuits, respectively.

After initiating the hemodialysis treatment, the operator of the hemodialysis system 700 (e.g., the physician, nurse, medical assistant, or patient) determines the prescribed Epogen® dose and then consults a dosing schedule for the different vial combinations that can be used to deliver the prescribed Epogen® dose. The operator then selects one of the Epogen® vial combinations provided based on the operator's preference and loads the selected Epogen® vials into the drug vial holders. The operator also loads a vial of Venofer® into one of the drug vial holders.

The operator of the system then connects the disposable drug administration fluid line cassette 707 to the inner surface of the door 704 by inserting the frame 166 and feeder lines 122 into their corresponding recessed regions 712 and slots 714. As a result of this, the hexagonal shaped projections 706 that extend from the inner surface of the door 704 slide into the matching holes 780 formed in the frame 166 of the drug administration fluid line cassette 707. The mating engagement of the hexagonal shaped projections 706 and openings 780, along with the snap fit of the cassette frame 166 and feeder lines 122 into their corresponding recessed regions 712 and slots 714, helps ensure that the cassette 707 remains securely fixed to the door 704. In addition, the unique hexagonal shape of the projections 706 and openings 780 can help to ensure that only drug administration fluid line cassettes intended for use with the drug delivery device 703 can be used. For example, drug administration fluid line cassettes that do not include holes capable of receiving the hexagonal projections 706 of the door 704 could not be properly secured to the door 704. This would indicate to the operator that an incorrect cassette was loaded into the cassette compartment of the drug delivery device 703 and, in many cases, will prevent the door 704 from shutting and thus prevent the drug delivery device 703 from being operated with that cassette.

After loading the drug administration fluid line cassette 707 onto the door 704, the operator closes the door 704 and secures a latch 767 to hold the door 704 in the closed position. Because the cassette 707 is securely fastened to the door 704 in a desired position, the feeder lines 122 align with their associated pumps 732 and bubble detectors 128 when the door 704 is closed. Thus, as the door 704 is closed, the protruding peristaltic pumps 732 press the feeder lines 122 into the raceways 718 formed along the inner surface of the door 704, and the inner surface of the door 704 presses the feeder lines 122 into engagement with the bubble detectors 128. With the door 704 in the closed position, the spikes 736 of the cassette 707 rest directly below the holes formed in the bottom members 740, 744 of the vial holder 708, 710.

The prescribed dosages of Venofer® and Epogen® are then entered into the drug delivery device 703 using the user interface 734 of the hemodialysis machine 701 with which the control unit of the drug delivery device 703 is in communication. Alternatively or additionally, the prescribed dosage of Venofer® and Epogen® can be electronically transmitted to the control unit of the drug delivery device 703 from a database or website accessible by the patient's prescribing physician. The operator, after reviewing the prescribed dosage entered into or transmitted to the machine, confirms that the prescribed dosage is correct by pressing a button (e.g., an "Accept" or "Confirm" button) on the user interface 734 of the hemodialysis machine 701, which initiates the spiking and priming process.

Referring briefly again to FIG. 18, the vial spiking process begins by activating the motors 766 of the drive mechanisms 746, 747 connected to the vial holders 708, 710, which first causes the vial holders 708, 710 to compress the rubber seals 123 of the vials 116, 118 between the caps 119 and necks 121 of the vials 116, 118, and then, upon continued operation of the drive mechanisms 746, 747, causes the vials 116, 118 to move sufficiently downward so that the spikes 736 of the cassette 707 pierce the rubber seals 123 of the vials 116, 118. In particular, operation of the motors 766 of the drive mechanisms 746, 747 causes the top members 738, 742 of the drug vial holders 708, 710 to move downward and squeeze the vials 116, 118 between the top members 738, 742 and bottom members 740, 744 of the drug vial holders 708, 710. Before the subsequent step of causing the top members 738, 742 and bottom members 740, 744 of the drug vial holders 708, 710 to move downward in unison so that the spikes 736 of the drug administration fluid line cassette 707 pierce the rubber seals 123 of the vials 116, 118, the rubber seals 123 are compressed to a sufficient degree to inhibit movement of the rubber seals 123 relative to the caps 119 and neck portions 121 of the vials 116, 118. The compression of the rubber seals 123 results from the initial resistance to downward force of the bottom members 740, 744 of the drug vial holders 708, 710 as the downward moving top members 738, 742 contact the vials 116, 118 and squeeze the vials between the top and bottom members. This resistance to downward force is provided by the springs 759 disposed between the bottom cross bars 756 and the bottom supports 750. After the rubber seals 123 are sufficiently compressed, the motors 766 of the drive mechanisms 746, 747 continue to run and the force applied to the bottom members 740, 744 of the drug vial holders 708, 710, and thus to the bottom member extensions 753, rises to a sufficient level to cause the springs 759 to collapse, which results in downward movement of the bottom members 740, 744 along with the top members 738, 742 and the vials 116, 118. The motors 766 continue to run until the vial holders 708, 710 are moved downward a sufficient distance to cause the spikes 736 to pass through the openings in the bottom members 740, 744 of the drug vial holders 708, 710 and pierce the rubber seals 123 of the vials 116, 118. Because the rubber seals 123 are held in a compressed state while they are pierced by the spikes 736, bulging of the rubber seals 123 into the neck portion 121 of the vials 116, 118 can be inhibited or prevented.

In certain implementations, to counteract any inward bulging of the rubber seals 123 that might have occurred during the spiking process, the motors 766 are operated in the reverse direction for a brief period of time after the spikes 736 have been fully inserted into the vials 116, 118 (e.g., after the bottom members 740, 744 of the drug vial holders 708, 710 or the caps 119 of the drug vials 116, 118 have contacted the bases or support members from which the spikes 136 extend) in order to move the vial holders 708, 710 up slightly. As the vial holders 708, 710 move upward, friction between the spikes 736 and the rubbers seals 123 of the vials 116, 118 causes a downward force to be applied to the rubber seals 123. Depending on the period of time for which the motors 766 are operated in the reverse direction, the rubber seals 123 can be returned to their neural resting position (i.e., not bulged inward and not bulged outward), or the rubber seals 123 can be caused to bulge slightly outward from the vials 116, 118. Either configuration will help to ensure that the drugs are fully evacuated from the vials during the drug delivery process.

After spiking the vials 116, 118, the feeder lines 122 of the drug administration fluid line cassette 707 are primed by activating the pumps 732, either sequentially or simultaneously, which causes a portion of the drug to be drawn from each of the vials 116, 118. During the priming process, each pump 732 remains on until the drug from its associated vial 116, 118 is detected by the bubble detector 128, at which point the pump 732 is stopped and pinches off or occludes that feeder line 122. If the drug is not detected by one of the bubble detectors 128, an alarm can be activated prompting the operator to replace or adjust the drug administration fluid line cassette 707 and repeat the priming process.

After priming the feeder lines 122, Venofer® is delivered from the Venofer® vial 116 to the drip chamber 106 by activating the pump 732 associated with the Venofer® vial 116 (while leaving all of the other pumps off). Upon determining that the prescribed dosage of Venofer® has been delivered to the drip chamber 106, the control unit causes the pump 732 associated with the Venofer® feeder line to be turned off.

The pump associated with the first Epogen® vial 118 (i.e., the Epogen® vial directly to the right of the Venofer® vial 116) is then activated such that Epogen® is delivered to the drip chamber 106. When the bubble detector 128 detects air in the feeder line 122, a signal is sent to the control unit, indicating that the first Epogen® vial 118 is empty. The control system then sends a signal causing the pump associated with the first Epogen® vial 118 to be turned off after assuring that an additional known volume is pumped so that the Epogen® in the line downstream of the bubble detector 128 is flushed down to a segment where the delivery of drug from the next vial can push that Epogen® remaining in the line to the drip chamber 106. In particular, the control unit ensures that the additional pumped volume is sufficient to push the Epogen® past the pump 732 and into the passage of the manifold 168 such that the next volume of drug delivered will push the Epogen® to the drip chamber 106. The control unit also sends a signal to activate the pump 732 associated with the second Epogen® vial 118 (i.e., the Epogen® vial directly to the right of the first Epogen® vial). The Epogen® delivery process described above is then repeated for the second and third Epogen® vials.

After delivering the desired amounts of Venofer® and Epogen® to the drip chamber 106, the drug delivery device 703 is deactivated and the drug administration fluid line cassette 707 and vials 116, 118 are removed from the drug delivery device 703 and discarded.

In some implementations, an air bubble is pulled into the passage of the manifold 168 via the feeder line 122 and delivered to the drip chamber 106 when transitioning from one drug vial to the next. This technique, as described above, can help to clear any remaining medicament from the previously used vial out of the manifold passage and drug delivery line 104 to help ensure that all of the drug evacuated from the vial is delivered to the patient and to reduce (e.g., eliminate) mixing of two distinct drugs both of which are delivered to the drip chamber 106 via the manifold passage and drug delivery line 104.

In certain implementations, the operating speed of each of the pumps 732 is gradually increased as the quantity of drug in the vial from which the drug is being withdrawn decreases. As the quantity of drug in the vial decreases, a slight vacuum is produced in the vial. This vacuum can result in a decreased flow rate of the drug from the vial if the pump speed remains constant. Thus, gradually increasing the pump speed as the drug is drawn from the vial can help to maintain a substantially constant flow rate of the drug from the vial throughout the drug delivery process.

While the raceway members 716 that are exposed on the inner surface of the door 704 of the drug delivery device 703 and receive the rollers 733 of the peristaltic pumps 732 have been described as being connected to the door 704 via springs located at the top and bottom regions of the raceway members 716, alternative configurations are possible. In some implementations, for example, only a single spring is used to connect each raceway member 716 to the door 704. The single spring can, for example, be connected to a mid-region of the raceway member.

While the door 704 of the drug delivery device 703 has been described as including hexagonal projections 706 that mate with hexagonal holes 780 formed in the cassette 707, the reverse configuration is also possible. For example, the cassette 707 can be provided with hexagonal projections and the door 704 of the drug delivery device 703 can include hexagonal holes that mate with those projection. Similarly, as an alternative to including these mating features on the inner surface of the door 704 and the front surface of the cassette 707, the mating features can be provided on the inner face of the drug delivery device 703 and the rear surface of the cassette 707. Also, as an alternative to hexagonal holes and projections, holes and projections of various other shapes, such as pentagons, octagons, stars, logos, etc., can be used. In certain implementations, the mating holes and projections are irregularly shaped to further ensure that only cassettes intended for use with the drug delivery device can be properly disposed in the cassette compartment of the drug delivery device.

While the spikes 736 of the drug administration fluid line cassette 707 have been illustrated as having sharp, tapered ends, the spikes can alternatively be shaped similar to those spikes 236, 336 described above with respect to FIGS. 10 and 11.

While the top members 738, 742 of the drug vial holders 708, 710 described above are configured to contact the upward facing bottom surfaces of the inverted drug vials 116, 118, the top members can be configured to contact other portions of the vials. In some implementations, for example, the drug vial holders include top members in the form of clamps that grasp the neck portions 121 of the vials 116, 118 during use. The clamp mechanisms, when clamping the neck portions 121 of the vials 116, 118, can be moved in the downward direction toward the bottom members 740, 744 such that the rubber seals 123 of the vials 116, 118 are compressed between the caps 119 and neck portions 121 of the vials 116, 118. While the bodies of drug vials come in a variety of shapes and sizes, most drug vials have similarly sized and shaped caps and neck portions. Thus, this arrangement can advantageously allow the drug vial holders to accommodate various differently sized and shaped vials, which can allow the drug delivery device to be used to delivery a variety of different drugs.

While the bottom members 740, 744 of the drug vial holders 708, 710 have been described as supporting the caps 119 of the inverted drug vials 116, 118, other arrangements are possible. In certain implementations, for example, the bottom members of the drug vial holders include openings that are sized to allow the caps 119 of the vials 116, 118 to pass therethrough and to prevent the neck portions 121 and/or the body portions 125 of the vials 116, 118 from passing therethrough. Each of the openings can, for example, be a circular opening that has a diameter greater than the maximum outer diameter of the cap 119 to be inserted therethrough and less than the maximum outer diameter of the neck portion 121 and/or the body portion 125 of the vial 116, 118. Such vial holders can be used in combination with other mechanisms, such as drug vials spikes 120, that help to prevent the rubber seals of the drug vials from bulging inwardly into the vial when pierced by the spikes.

While the drug vial holder drive mechanisms 746, 747 illustrated in FIG. 18 include linear guides 757 that extend from the vertical support wall 751 and along which the top member extensions 752 and bottom member extensions 753 slide during use, the top and bottom member extensions can alternatively be configured to slide along the side surfaces of the vertical support wall 751 itself.

Figure 19:
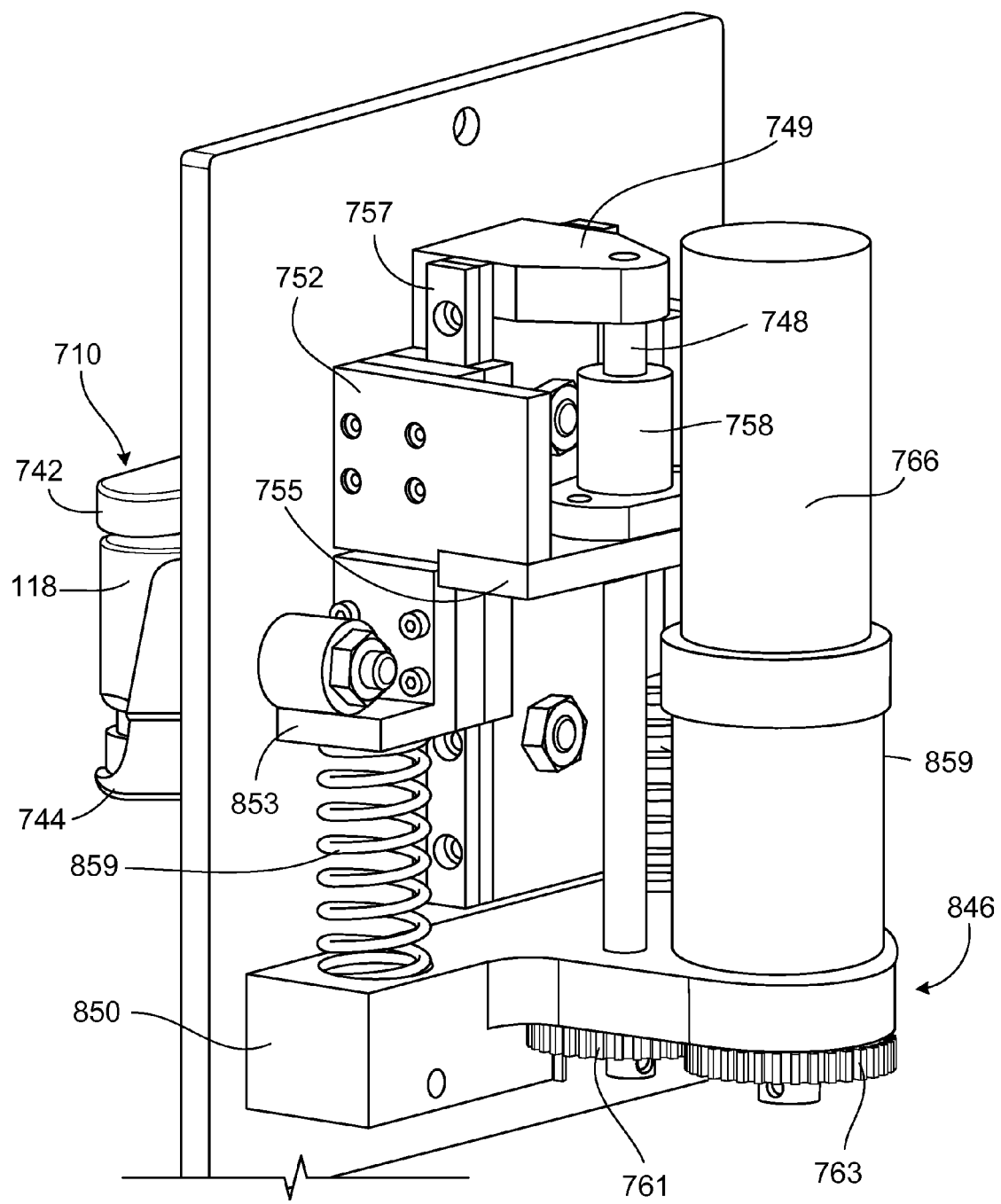
FIG. 19 is a perspective view of another type of drive mechanism that can be used to drive the drug vial holders of the drug delivery device of FIG. 14.

While each of the drug vial holder drive mechanisms 746, 747 illustrated in FIG. 18 include a single spring 759 that is positioned between the bottom cross bar 756 and the bottom support 750 and surrounds the drive shaft 748, in certain implementations, multiple springs are used to provide resistance to downward movement of the bottom member of the drug vial holder. As shown in FIG. 19, for example, a drug vial holder drive mechanism 846 includes a spring 859 positioned between bottom member extensions 853 and a bottom support 850. Each of the bottom member extensions 853 is L-shaped and includes a vertical member and a horizontal member. The horizontal member of each bottom member extensions 853 extends away from the drive shaft 748, toward an outer edge the drug delivery device. This portion, which supports the spring 859 is thus positioned nearer the end regions of the bottom member 744 of the drug vial holder 710. This arrangement can help to ensure that sufficient resistance to downward movement is provided to the end regions of the bottom member 744 of the drug vial holder 710 to allow the rubber seals 123 of the vials 118 located on the opposite ends of the drug vial holder 710 to be compressed before the drug vial holder 710 as a whole is moved downward toward the spikes 736 of the cassette 707. While the drive mechanism 846 may be particularly advantageous for drug vial holders that are designed to accommodate multiple vials and thus have a relatively wide bottom member, the drive mechanism can be used with drug vial holders that are designed to hold only a single vial.

Figure 20:
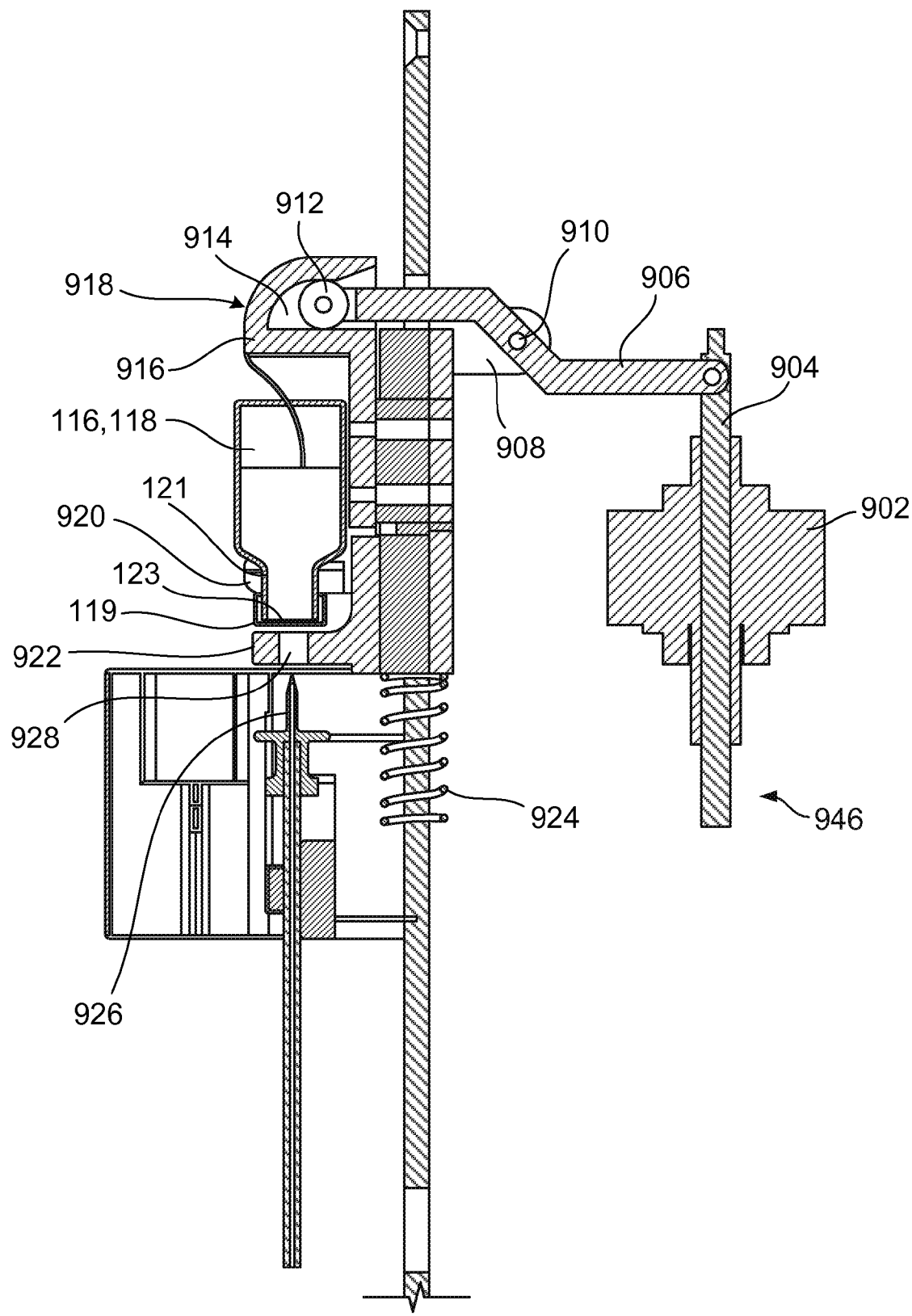
FIG. 20 is a side view of an additional type of drive mechanism that can be used to operate the drug vial holders of the drug delivery device of FIG. 14.

Other types of drive mechanisms can also be used to operate the drug vial holders 708, 710 in order to clamp and spike the drug vials 116, 118. An example of such a drive mechanism 946 is schematically illustrated in FIG. 20. As shown, the drive mechanism 946 includes a motor 902 that is configured to drive an output shaft 904 in an upward direction. The output shaft 904 is pivotally connected to a pivot arm 906, which is pivotally connected to a housing 908 of the drug delivery device via a central pivot 910. As the motor 902 drives the output shaft 904 upward, the pivot arm 906 rotates in the clockwise direction about the pivot 910. As a result, a bearing 912 attached to the end of the pivot arm 906 opposite the motor output shaft 904 moves downward. The bearing 912 is positioned in a cavity 914 of an upper member 916 of a drug vial holder 918, which is shown holding the drug vial 116, 118. The neck portion of the drug vial 116, 118 is firmly held by a fork or clamp 920 of the upper member 916. Thus, as the upper member 916 of the drug vial holder 918 is moved downward, the drug vial 116, 118 retained by the fork 920 also moves downward.

As the motor 902 continues to drive the output shaft 904 upward, which causes the upper member 916 and the drug vial 116, 118 held therein to continue to move downward, the cap 119 of the drug vial is forced downward against a lower member or shoe 922 of the drug vial holder 918. The lower member 922, like the upper member 916 is vertically moveable relative to the housing of the drug delivery device. A spring 924 is fixed to the housing of the drug delivery device and thus resists downward movement of the lower member 922. The spring 924 can, for example, be configured to withstand a downward force of about 1 pound to about 20 pounds (e.g., about 1 pound to about 10 pounds, about 1 pound to about 5 pounds, about 5 pounds to about 10 pounds). As the downward movement of the lower member 922 is resisted by the spring 924, the rubber seal 123 of the drug vial 116, 118 is compressed between the cap 119 and neck portion 121 of the drug vial 116, 118.

Further operation of the motor 902 causes the downward force applied to the lower member 922 to exceed the resistance force of the spring 924. As the spring 924 is compressed, the upper and lower members 916, 922 of the drug vial holder 918 and the drug vial holder 116, 118 itself are moved downward toward a drug vial spike 926. The drug vial spike 926 eventually passes through an aperture 928 formed in the lower member 922 and pierces the rubber seal 123 of the drug vial 116, 118 such that drug can be drawn out of the drug vial 116, 118 via the drug vial spike 926.

After the drug has been delivered from the drug vial 116, 118, the motor 902 is tuned off and the spring 924 causes the upper and lower members 916, 922 of the drug vial holder 918 and the drug vial 116, 118 to move upward, away from the drug vial spike 926.

While the drug vial holder drive mechanisms described above use one or more springs to cause the bottom members 740, 744 of the drug vial holders 708, 710 to resist downward movement and thus allow compression of the rubber seals 123 of the vials 116, 118, other types of devices or mechanisms that are capable of initially resisting vertical movement of the bottom member 740, 744 and then allowing downward movement when a sufficiently high force is applied to the bottom member 740, 744 can be used. Examples of such devices include opposing polarity magnets, elastomers, or other members that provide a force proportional to displacement.

As an alternative to or in addition to using a gear arrangement to connect the output shaft of the motor to the drive shaft of the various drug vial holder drive mechanisms described above, other connection techniques that allow the motor to rotate the drive shaft can be used. In certain implementations, for example, a pulley is connected to both the output shaft of the motor and the drive shaft of the drive mechanism in order to allow the motor to rotate the drive shaft.

Figure 21:
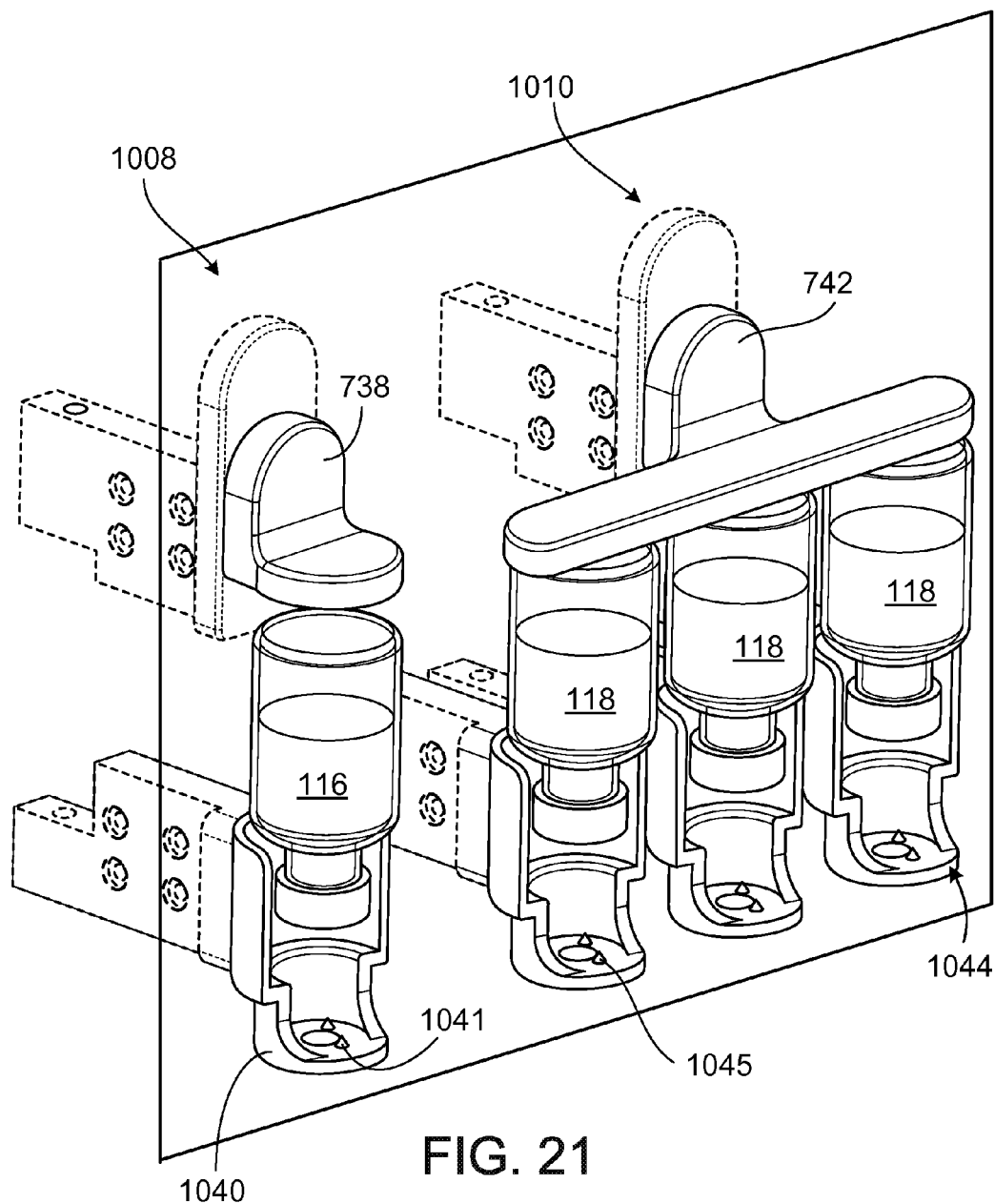
FIG. 21 is a perspective view of drug vial holders each of which includes pointed projections extending from its lower member for denting the caps of drug vials held by the drug vial holder assembly during use.
Figures 22, 23:
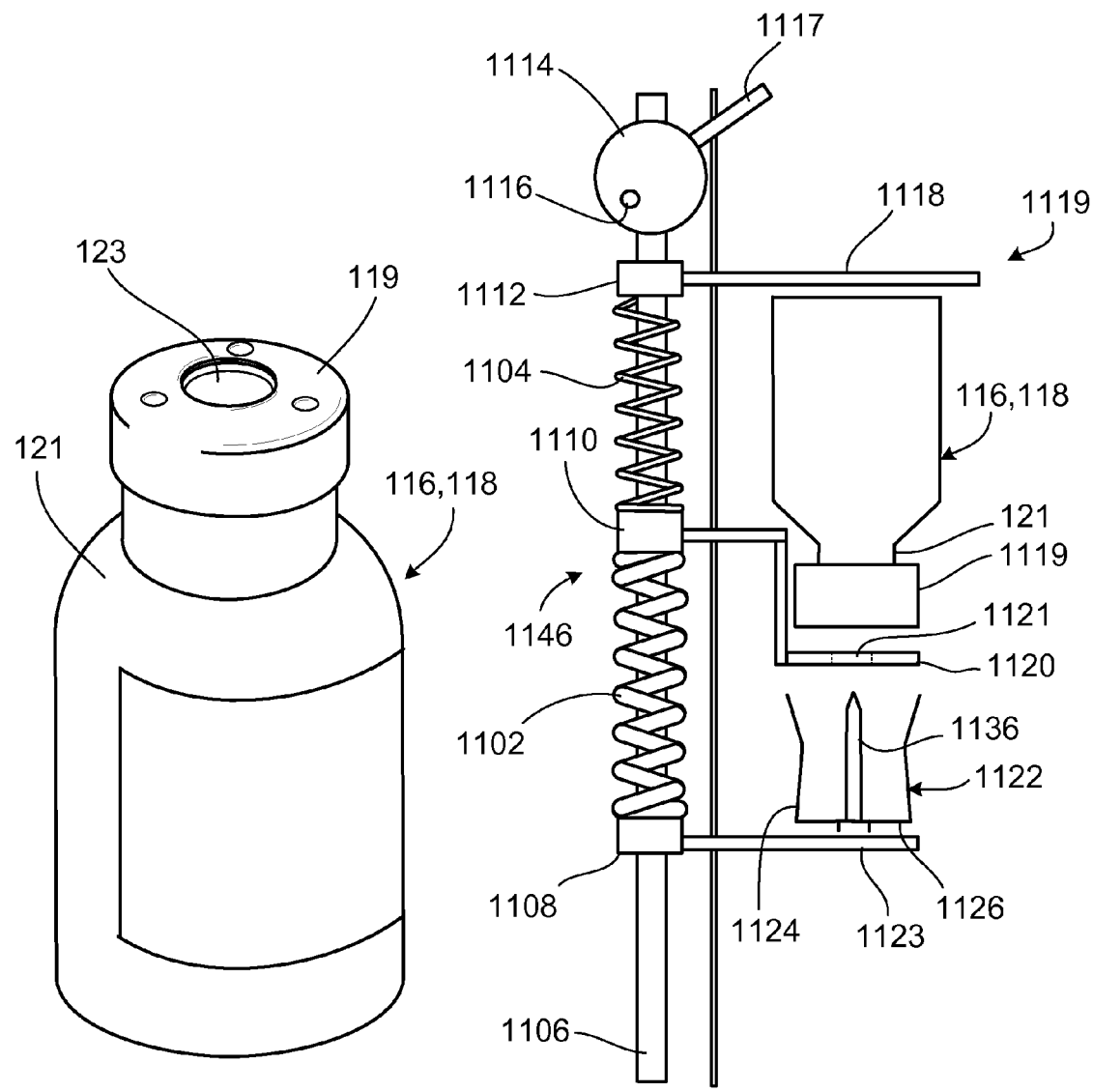
FIG. 22 is a perspective view of a drug vial including a cap that has been dented by one of the drug vial holders of FIG. 21 to help fix a rubber seal of the vial relative to the cap and body of the vial.
FIG. 23 is a schematic side view of a manually operated drive mechanism and an associated drug vial holder that can be operated by the manually operated drive mechanism.

While the bottom members 740, 744 of the drug vial holders 708, 710 have been described as having substantially flat or smooth surfaces on which the drug vials 116, 118 rest, those surfaces can alternatively include pointed projections that dent the cap 119 of the vial 116, 118 into the rubber seal 123 of the vial 116, 118 when the vial 116, 118 is squeezed between the top members 738, 742 and bottom members 740, 744 of the drug vial holders 708, 710. FIG. 21 illustrates drug vial holders 1008, 1010 that include such pointed projections. As shown in FIG. 21, each of the drug vial holders 1008, 1010 includes a bottom member 1040, 1044 with upper surfaces from which three pointed projections 1041, 1045 extend. The pointed projections 1041, 1045 only extend slightly above the upper surfaces of the bottom members 1040, 1044. In certain implementations, for example, the pointed projections 1041, 1045 extend about 0.010 inch to about 0.030 inch (e.g., about 0.020 inch) above the upper surfaces of the bottom members 1040, 1044. As the top members 738, 742 of the drug vial holders 1008, 1010 are moved toward the bottom members 1040, 1044 and the vials 116, 118 are squeezed therebetween, the force of the bottom members 1040, 1044 acting upwardly on the caps 119 of the vials 116, 118 causes each of the pointed projections 1041, 1045 to dent a discrete portion of the cap 119 into the rubber seal 123 of the vial 116, 118. An illustration of a vial 116, 118 that has been clamped in this manner is shown in FIG. 22. The discrete portions of the cap 119 that protrude into the rubber seal 123 can, in addition to the compression of the rubber seal 123, help to prevent the rubber seal 123 from moving or slipping relative to the cap 119 and neck portion 121 of the vial.

While the drive mechanisms of the drug vial holders described above include motors that cause the top members of the vial holders to move relative to the bottom member, manually operated drive mechanisms can alternatively or additionally be used. FIG. 23 is a side schematic view of such a manually operated drive mechanism 1146. The drive mechanism 1146 includes lower and upper springs 1102, 1104 disposed along a guide shaft 1106. A collar 1108 is fixed to the guide shaft 1106 below the lower spring 1102, and the bottom end region of the spring 1102 abuts the collar 1108. A collar 1110 is positioned between the lower and upper springs 1102, 1104, and a collar 1112 is positioned above the upper spring 1104. Collars 1110, 1112 are moveable along the length of the guide shaft 1106.

An upper member or plate 1118 of a drug vial member 1119 is fixed to the collar 1112, and a lower member or shoe 1120 of the drug vial holder 1119 is fixed to the collar 1110. As a result, as the collars 1110, 1112 move relative to the guide shaft 1106, the lower and upper members 1120, 1118 of the drug vial holder 1119 similarly move relative to the guide shaft 1106. Much like some of the drug vial holders described above, the lower member 1120 of the drug vial holder 1119 is configured to support the cap 119 of the inverted vial 116, 118, and the upper member 1118 is configured to move downward relative to the lower member 1120 to clamp the drug vial 1116, 1118 therebetween.

A drug vial spike assembly 1122 is fixed to the collar 1108 via a bar 1123. As a result, the drug vial spike assembly 1122 is fixed relative to the guide shaft 1106. The drug vial spike assembly 1122 includes flexible fingers 1124 that extend upward from a base 1126 and surround a central spike 1136. The flexible fingers 1124 are configured to releasably retain the lower member 1120 of the drug vial holder 1119 and the cap 119 of the drug vial 116, 118 when the lower member 1120 and the drug vial 116, 118 are moved downward such that the central spike 1136 passes through an opening 1121 formed in the lower member 1120 and pierces the rubber seal of the vial 116, 118.

An eccentric cam 1114 having a pivot point 1116 is positioned above the collar 1112 and is configured to move the collar 1112 along the guide shaft 1106 as the eccentric cam 1114 is rotated by an operator. The operator rotates the eccentric cam 1114 by pulling a lever 1117 that is connected to the eccentric cam 1114. As the cam 1114 rotates, the collar 1112 compresses the upper spring 1104, which has a lower resistance than the lower spring 1102, and causes the upper member 1118 of the drug vial holder 1119 to move downward. Further compression of the upper spring 1104 causes the upper member 1118 to contact the vial 116, 118 and to compress the vial 116, 118 between the upper and lower members 1118, 1120 of the drug vial holder 1119. The lower spring 1102 has a spring force that resists downward movement of the collar 1110 and the lower member 1120 to an extent to allow the rubber seal of the vial 116, 118 to be compressed between the cap 1119 and the neck portion 121 of the vial 116, 118. As the eccentric cam 1114 is rotated further, the spring 1102 is compressed and the drug vial holder 1119 and the vial 116, 118 are moved downward toward the drug vial spike assembly 1122. The eccentric cam 1114 is rotated until the central spike 1136 has pierced the rubber seal of the vial 116, 118, and the lower member 1120 and the vial 116, 118 abut the base 1126 of the drug vial spike assembly 1122.

While the drive mechanism 1146 has been described as being configured such that the collar 1108 is fixed relative to the guide shaft 1106, and the collars 1110, 1112 are moveable relative to the guide shaft 1106, in other implementations, the collar 1110 is fixed relative to the guide shaft 1106, and the collars 1108, 1112 are moveable relative to the guide shaft 1106. In such implementations, a downward force is applied to the collar 1112 when the eccentric cam 1114 is rotated, and an upward force is applied to the collar 1108 when the eccentric cam 1114 is rotated. Due to the different spring forces of the springs 1102, 1104, the upper spring 1104 is first to compress, causing the upper member of the drug vial holder 1119 to move toward the lower member 1120 of the drug vial holder 1119. After the drug vial 116, 118 has been sufficiently compressed between the upper and lower members 1118, 1120, the lower spring 1102 compressing, allowing the drug vial spike assembly 1122 to move upward toward the drug vial 116, 118 such that the central spike 1136 pierces the rubber seal of the drug vial 116, 118.

As an alternative to or in addition to using the mating projections 706 and openings 780 to inhibit or prevent unapproved or incorrect drug administration fluid line cassettes from being used with the drug delivery device 703 described above, the drug delivery device 703 can include a sensor (e.g., a bar code reader or RFID detector) that can identify approved or correct drug administration fluid line cassettes (e.g., by reading a bar code reader or RFID tag that identifies the cassette). The sensor can be connected to the control unit, and the control unit can be programmed to prevent operation of the drug delivery device unless an approved drug administration fluid line cassette is detected. These types of sensors can similarly be included in the other drug delivery devices described herein.

While the control unit has been described as being part of the drug delivery device 703, in certain implementations, the control unit is not physically present in the modular drug delivery device. In such implementations, for example, the drug delivery device 703 can be connected to a control unit located elsewhere in the hemodialysis machine (e.g., the main control unit of the hemodialysis machine).

Figure 24:
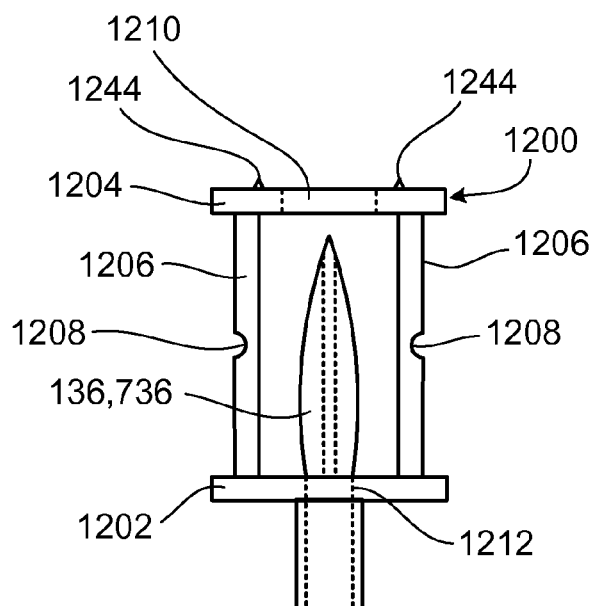
FIGS. 24-29 are front views of various different types of spike covers secured to drug vial spikes.

While the drug administration fluid line sets have been described as being provided with unitary, removable covers that protect the spikes of those fluid line sets prior to use, other types of covers can be used. In some implementations, a separate cover is attached to each spike of the administration fluid line set. As shown in FIG. 24, for example, a spike cover 1200 includes a lower disk 1202 and an upper disk 1204 that are connected to one another by multiple, circumferentially spaced columns 1206. Each of the columns 1206 includes a weakened region (e.g., an annular depression or slot) 1208 that facilitates outward bowing of the columns 1206 when a downward axial force is applied to the upper disk 1204. The upper disk 1204 includes a central aperture 1210, which is sized to receive the spike 136, 736 when the downward axial force is applied to the upper disk 1204 causing the cylinder 1206 to bend such that the upper disk moves 1204 toward the lower disk 1202. The lower disk 1202 also includes a central aperture 1212 through which the spike 136, 736 extends. The central aperture 1212 in the lower disk 1202 is smaller than the aperture 1210 in the upper disk 1204 so that the lower disk 1202 engages the spike 136, 736 and helps to fix the lower disk 1202 relative to the spike 136, 736.

Still referring to FIG. 24, pointed projections 1244 (similar to the pointed projections 1044 described with respect to FIG. 21) extend from the upper surface of the upper disk 1204. The support columns 1206 are constructed to provide sufficient axial rigidity (prior to bending) such that when the user presses the vial 116, 118 down onto the upper disk 1204, the projections 1244 deform the cap 119 of the vial 116, 118, causing discrete deformed regions of the cap 119 penetrate the rubber seal 123 of the vial 116, 118. After the projections 1244 penetrate the rubber seal 123, further axial force applied to the upper disk 1202 causes the support columns 1206 to bend outward so that the upper disk 1204 moves downward toward the lower disk 1202, allowing the spike 136, 736 to pierce the rubber seal 123 of the vial 116, 118. The penetration of the projections 1244 into the rubber seal 123 of the vial 116, 118 limits transverse movement of the rubber seal 123 relative to the cap 119 as the spike 136, 736 pierces the rubber seal 123. As a result, the distance by which the central portion of the rubber seal 123 is deformed into the vial 116, 118 is reduced or minimized. After removing the vial 116, 118 from the spike 136, 736, the columns 1206 return to their original shape such that the cover 1200 again protects the spike 136, 736. This can, for example, help to prevent a user from pricking himself or herself with the spike 136, 736 when disposing the fluid set or cassette of which the spike 136, 736 and cover 1200 are components.

The lower disk 1202, upper disk 1204, and support columns 1206 are typically formed of a relatively rigid medical grade plastic such as ABS. However, other materials that permit the cover 1200 to operate in the manner described above can alternatively or additionally be used to form those components of the cover 1200.

The lower disk 1202 can be permanently or releasably attached to the spike 136, 736. Any of various techniques can be used to attach the lower disk 1202 to the spike 136, 736. For example, the lower disk 1202 can be thermally bonded, chemically bonded, and/or adhesively bonded to the spike 136, 736. Alternatively, the lower disk 1202 can be mechanically attached (e.g., by a press-fit or interference fit) to the spike 136, 736. Any of the above-noted techniques can similarly be used to attach the support columns 1206 to the lower and upper disks 1202, 1204.

Figure 25:
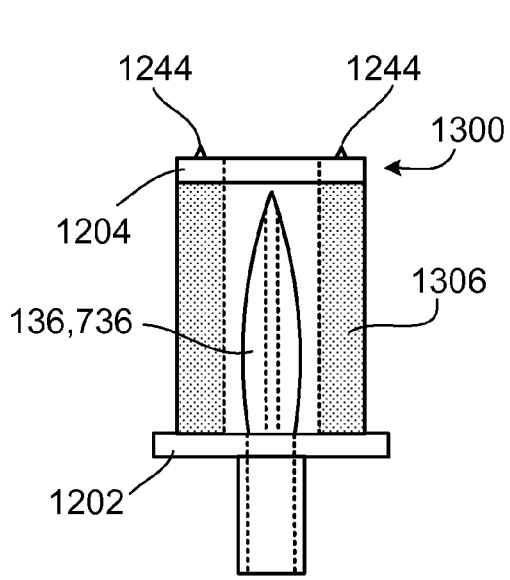

While the cover 1200 has been described as including the support columns 1206 with weakened annular regions 1208, other structures that permit a controlled collapse and subsequent expansion of the cover can alternatively or additionally be used. As shown in FIG. 25, for example, a spike cover 1300 includes a foam sleeve 1306 that is positioned between the lower and upper disks 1202, 1204 to permit the upper disk 1204 to move toward the lower disk 1202 as the user presses the vial 116, 118 downward on the upper disk 1204. In certain implementations, the sleeve 1306 is formed of polyurethane. However, other materials that provide the sleeve 1306 with the ability to collapse after a certain force (e.g., about 1 pound to about 20 pounds, about 1 pound to about 10 pounds, about 1 pound to about 5 pounds, about 5 pounds to about 10 pounds) is applied to it can be used. Examples of such materials include silicon, polyethylene, polypropylene, polyethylene/EVA block-type, polyolefin, polyether urethane, and polyester foams.

Figure 26:
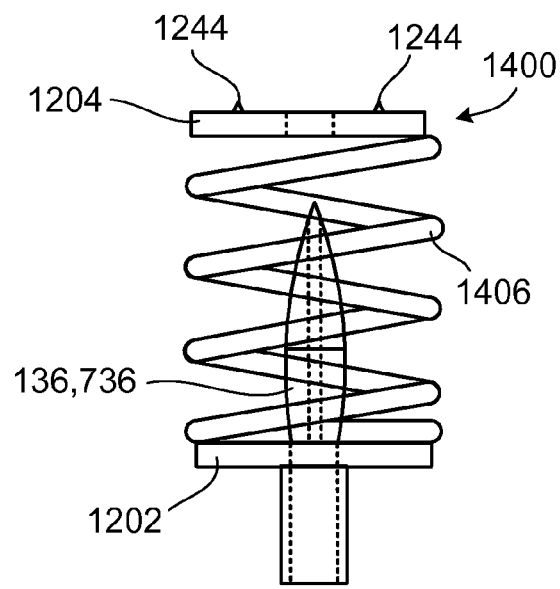

Referring now to FIG. 26, another spike cover 1400 includes a spiral spring 1406 that is disposed between the lower and upper disks 1202, 1204. In some implementations, the spring 1406 is formed of polycarbonate. However, the spring 1406 can alternatively or additionally be formed of other materials, such as ABS, polysulfone, polyethylene, and/or polypropylene.

Figure 27:
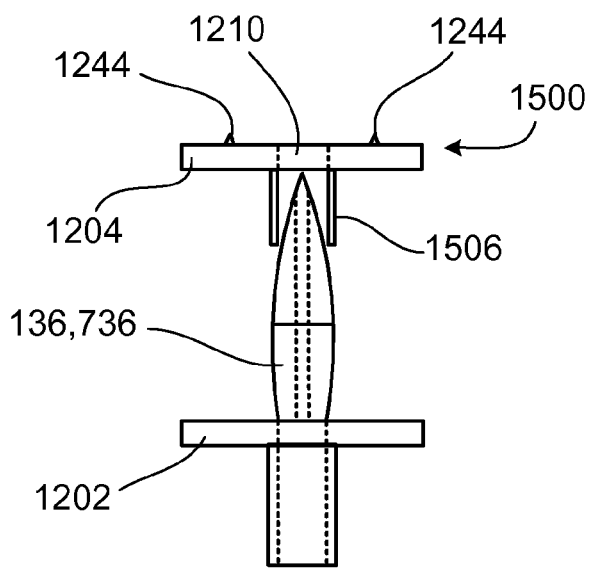

In some implementations, the lower and upper disks 1202, 1204 are not secured to one another via an intermediate member. As shown in FIG. 27, for example, a cover 1500 includes a tube 1506 that extends downward from the upper disk 1204. The tube 1506 has an inner diameter that is slightly smaller (e.g., about 0.05 mm to about 0.2 mm smaller) than the outer diameter of the spike 136, 736. The tube 1506 is typically formed of one or more polymeric materials, such as polyurethane, low density polyethylene, polyethylene, and/or polypropylene. As the user presses the vial 116, 118 down on the upper disk 1204, the larger diameter portion of the spike 136, 736 resists downward movement of the tube 1506 and the upper disk 1204 attached thereto. This initial pressure causes the projections 1244 of the upper disk 1204 to penetrate the rubber seal 123 of the vial 116, 118. The application of additional force to the vial 116, 118 then causes the tube 1506 to deform in a manner such that the inner diameter of the tube 1506 increases to a size greater than or equal to the outer diameter of the spike 136, 736 and allows the tube 1506 and upper disk 1204 to slide downward along the spike 136, 736. The length of the tube 1506 is about 20 percent the length of the spike 136, 736 to allow the spike to pass through the central aperture 1210 of the upper disk 1204 and pierce the rubber seal 123 of the vial 116, 118 as the upper disk 1204 and tube 1506 are forced downward along the spike 136, 736.

While the upper disk 1204 of the above covers has been described as having pointed projections 1244 that penetrate the rubber seal 123 of the vial 116, 118 as the vial is pressed down against the upper disk 1204, the upper disk 1204 can alternatively be provided with no such projections. It has been found that, in certain cases, the application of an axial force to the cap 119 of the vial 116, 118 using a substantially flat surface, such as that of an upper disk including no pointed projections, can sufficiently compress the rubber seal 123 between the cap 119 and neck 121 of the vial 116, 118 to resist (e.g., prevent) transverse movement of the rubber seal 123 relative to the cap 119 and neck 121 of the vial 116, 118.

Figures 28, 29:
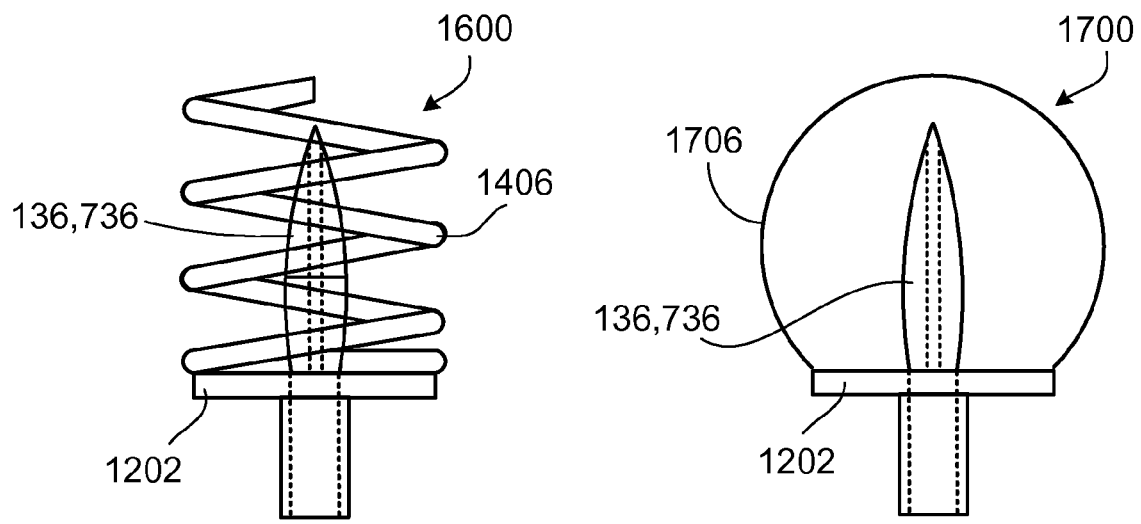

In some implementations, the spike covers include no upper disk. As shown in FIG. 28, for example, a cover 1600 includes only the spring 1406 secured to the lower disk 1202. The length of the spring 1406 in a relaxed (i.e., uncompressed) state is greater than the length of the spike 136, 736. Thus, prior to being compressed by the vial 116, 118, the spring 1406 extends along the entire length of the spike 136, 736 to prevent objects from inadvertently contacting the spike 136, 736 before the spike is inserted into the vial 116, 118. As a downward force sufficient to overcome the resistant force of the spring 1406 is applied by the vial 116, 118 to the spring 1406, the spring 1406 is compressed and the spike 136, 736 pierces the rubber seal 123 of the vial 116, 118.

Referring to FIG. 29, another cover 1700 includes an inflated or expanded balloon 1706 that is attached to the lower disk 1202 and surrounds the spike 136, 736. The balloon 1706 can be formed of one or more polymeric materials, such as PET, polyurethane, and/or ABS. To cause the spike 136, 736 to pierce the rubber seal 123 of the vial 116, 118, the user presses the vial 116, 118 down against the top of the balloon 1706 with sufficient force to compress the gas within the balloon 1706 and cause the balloon 1706 to move downward into contact with the tip of the spike 136, 736. The downward movement of the balloon 1706 causes the spike 136, 736 to pierce and thus deflate the balloon 1706.

While the spike covers described above with respect to FIGS. 24-29 are illustrated in use with spikes 136, 736, which have sharp, tapered tips, the spike covers can used with spikes of different shapes, such as the spikes 236, 336 that are described above with respect to FIGS. 10 and 11. These spike covers can be used with any of the drug vial holders or drug vial spikes described herein.

While some of the of the drug vial spiking devices, drug vial holders, and drug vial spike covers described above include projections that, during use, dent the cap 119 of the drug vial 116, 118 into the rubber seal 123 of the drug vial 116, 118, those projections can alternatively pierce the cap 119 and extend into the rubber seal 123. The projections can, for example, be formed with sharper tips such that when the vials 116, 118 are pressed against the projections using the methods described above, the projections pierce the caps 119. Alternatively or additionally, the vials 116, 118 can be pressed with greater force against the projections to ensure that the projections pierce the caps 119. As a result of the projections piercing the drug vial cap 119, sharp edges of the cap 119 surrounding the holes formed by the projections will protrude into and grip the rubber seal 123 of the drug vial 116, 118.

In addition, while some of the above-described drug vial spiking devices, drug vial holders, and drug vial spike covers have been described as including three circumferentially spaced projections that can be used to dent or pierce the caps 119 of the drug vials 116, 118, more or fewer than three projections can be used. In certain implementations, for example, the drug vial spiking devices, drug vial holders, and/or drug vial spike covers are provided with eight projections that are circumferentially spaced from one another by about 45 degrees.

Figure 30:
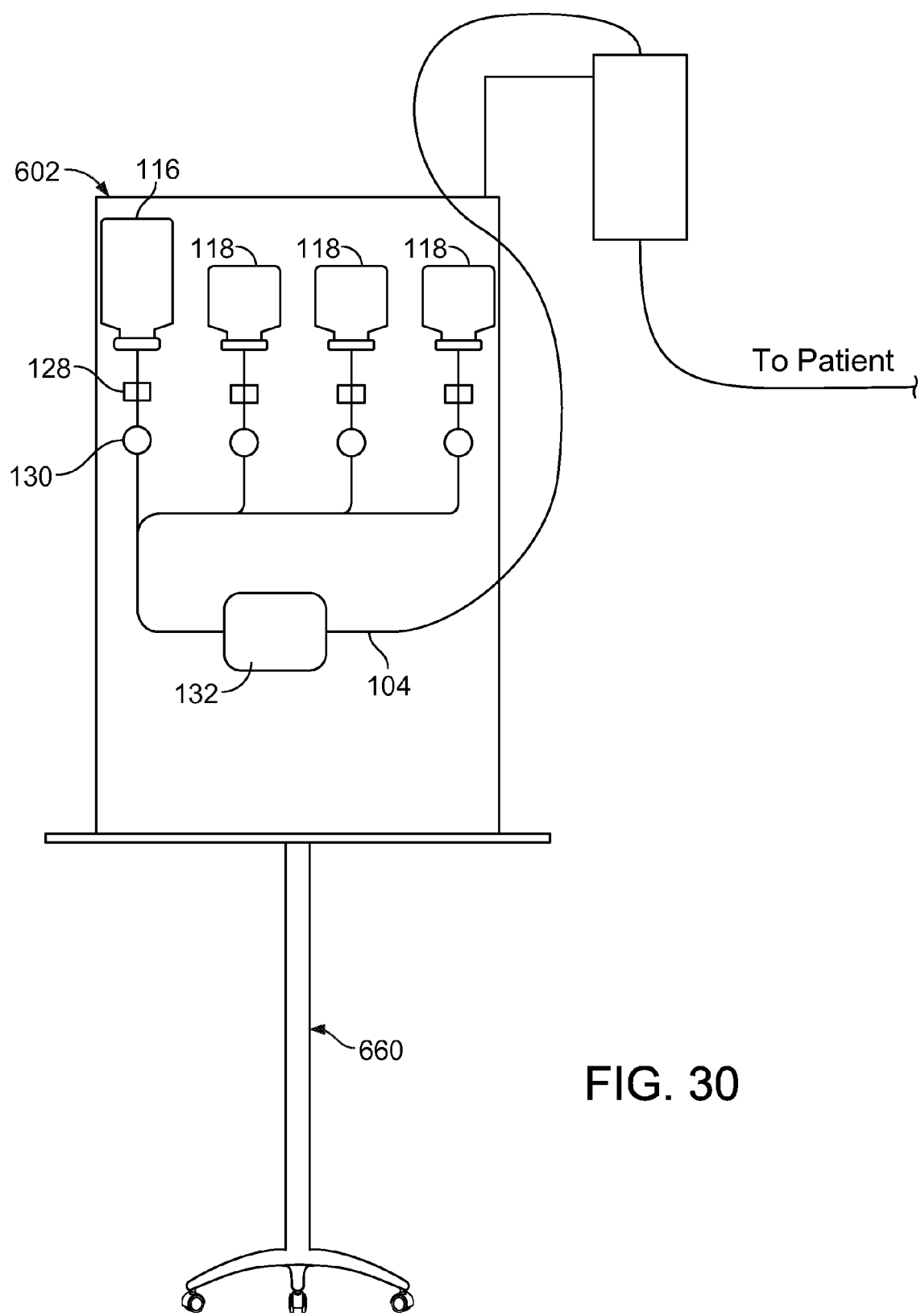
FIG. 30 is a schematic of a stand alone drug delivery system.

While certain drug delivery devices described herein are provided as components of hemodialysis systems, the drug delivery devices can be used in any type of medical device that would benefit from drug infusion capabilities. Alternatively, the drug delivery devices described herein can be configured to be operated as stand alone machines (i.e., not connected to another medical device). FIG. 30 illustrates a stand alone drug delivery device 602, which is substantially the same as the drug delivery device 103 described above but sits on a wheeled cart 660. The drug delivery line 104 of this stand alone drug delivery device 602 is connected to a drip chamber 662. During use, the drug(s) is/are delivered from the vials 116, 118 to the drip chamber 662. The drug(s) is/are then delivered from the drip chamber 662 to the patient via a fluid line 664. The drip chamber 662, similar to the above-described drip chamber 106, helps to ensure that any air pulled into the system from the vials does not reach the patient. The drug delivery device 602 can be used in a manner similar to the drug delivery device 103 described above to deliver drugs to a patient.

While the drug administration fluid line sets have generally been described as including a feeder line 122 and spike 136, 236, 336, 736 for each vial location provided in the drug vial holders, the drug administration fluid line sets can include any of various different numbers of feeder lines and spikes. Drug administration fluid line sets can, for example, be manufactured to include one, two, three, or four feeder lines and spikes, depending on the number of vials needed for treatment. As explained above, in certain cases, a treatment may not require three Epogen® vials and/or the treatment may not require a Venofer® vial. For those cases, drug administration fluid line sets including fewer feeder lines and drug vial spikes can be used.

While certain implementations above involve determining the volume of drug delivered by monitoring operation of the drug pump, other techniques can be used. In some implementations, for example, each of the vials is associated with a load scale that weighs the vial throughout the drug delivery. The change in weight of the vial during the drug delivery process can be used to determine the amount of drug delivered. In certain implementations, a drip counter is provided on the drip chamber to measure how many drips are delivered. Typically, each drop is about 0.05 ml. Thus, the total number of drops can be used to determine the total volume of drug delivered.

While the drug pumps 132, 732 have been described as peristaltic pumps, other types of mechanical pumps, including but not limited to "finger" peristaltic pumps, diaphragm pumps, solenoid pumps, syringe pumps, hydraulic pumps, piston pumps, pod pumps, and electric motor pumps, can be used.

While the drug delivery devices described above are equipped with drug vial holders capable of holding up to four vials, the drug delivery devices can alternatively be equipped with drug vial holders that are configured to hold fewer than or greater than four drug vials. Similarly, the drug administration fluid line sets/cassettes to be used with those drug vial holders can include fewer than or greater than four spikes and feeder lines.

While certain drug delivery devices described above include a vial holder configured to hold one vial and another vial holder configured to hold three vials, the drug delivery devices can be provided with any desired number of vial holders depending on the number of vials desired to be used during the particular type or types of treatment for which the drug delivery devices are designed. In certain implementations, the drug delivery device includes four separate vial holders, each with its own drive mechanism. This can permit four vials of different shapes and sizes to be used at the same time.

Figure 31:
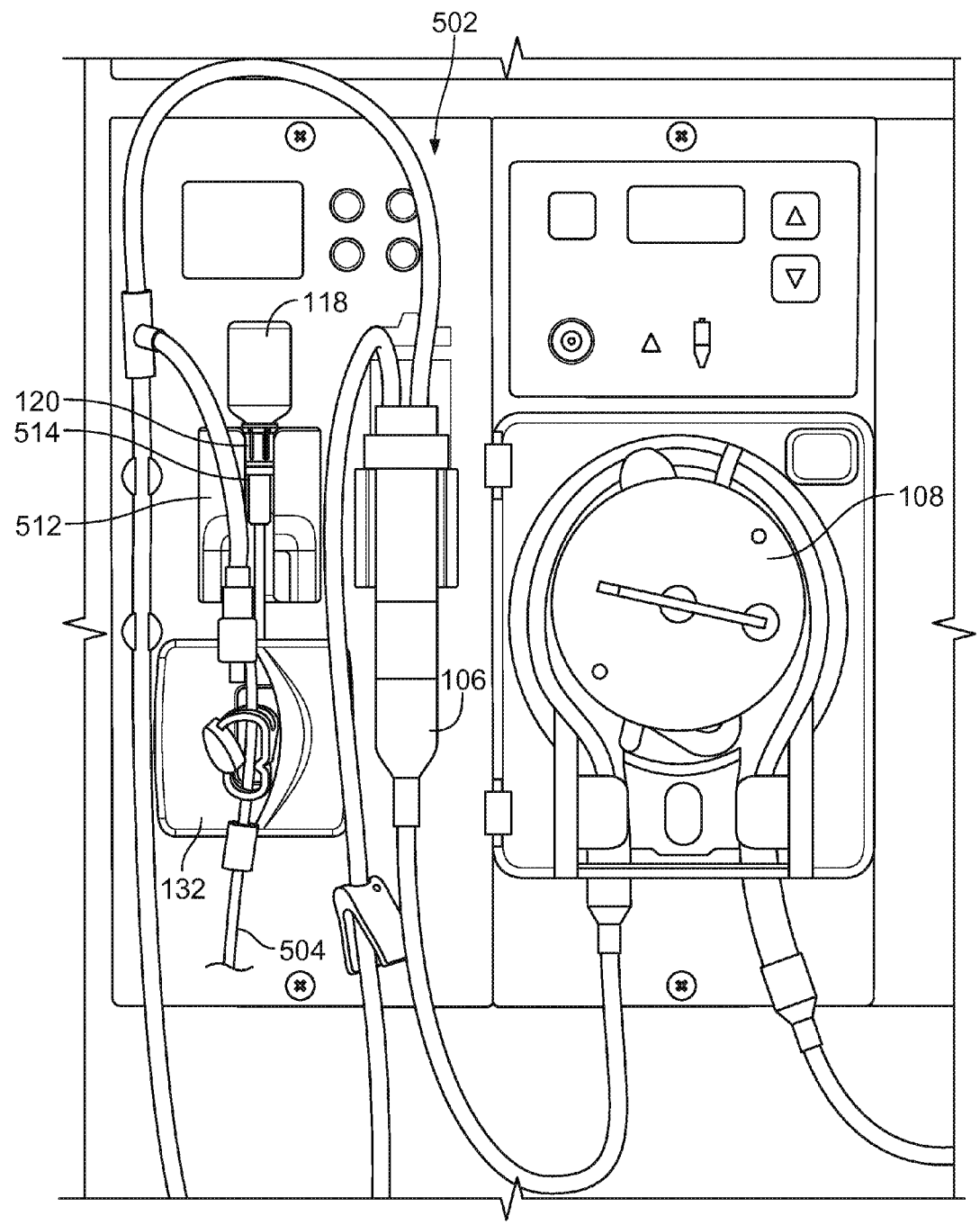
FIG. 31 illustrates a portion of a hemodialysis machine that includes a modular drug delivery device that is configured for use with a single drug vial.
Figure 32:
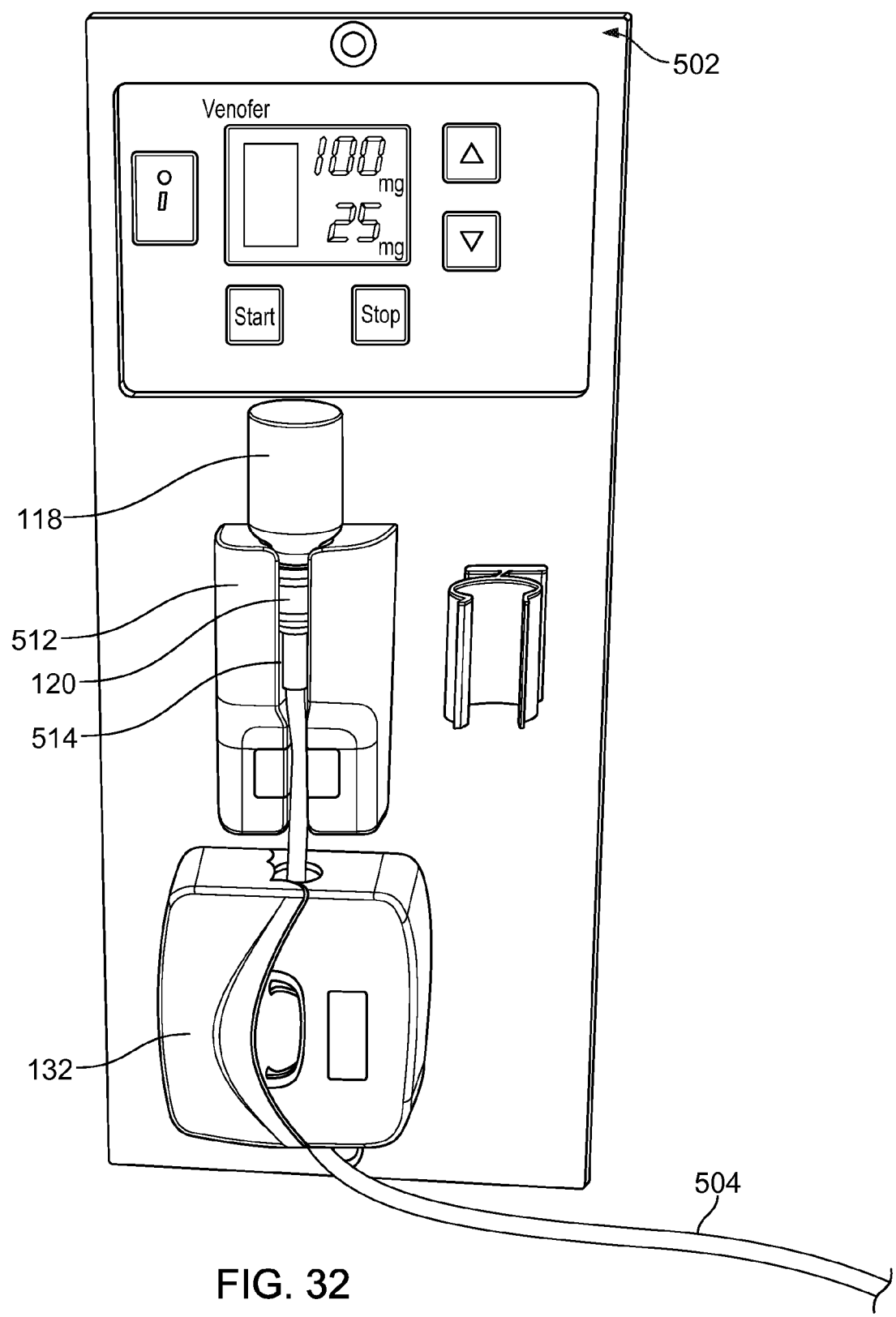
FIGS. 32 and 33 are perspective views of the modular drug delivery device of the hemodialysis machine of FIG. 31.
Figure 33:
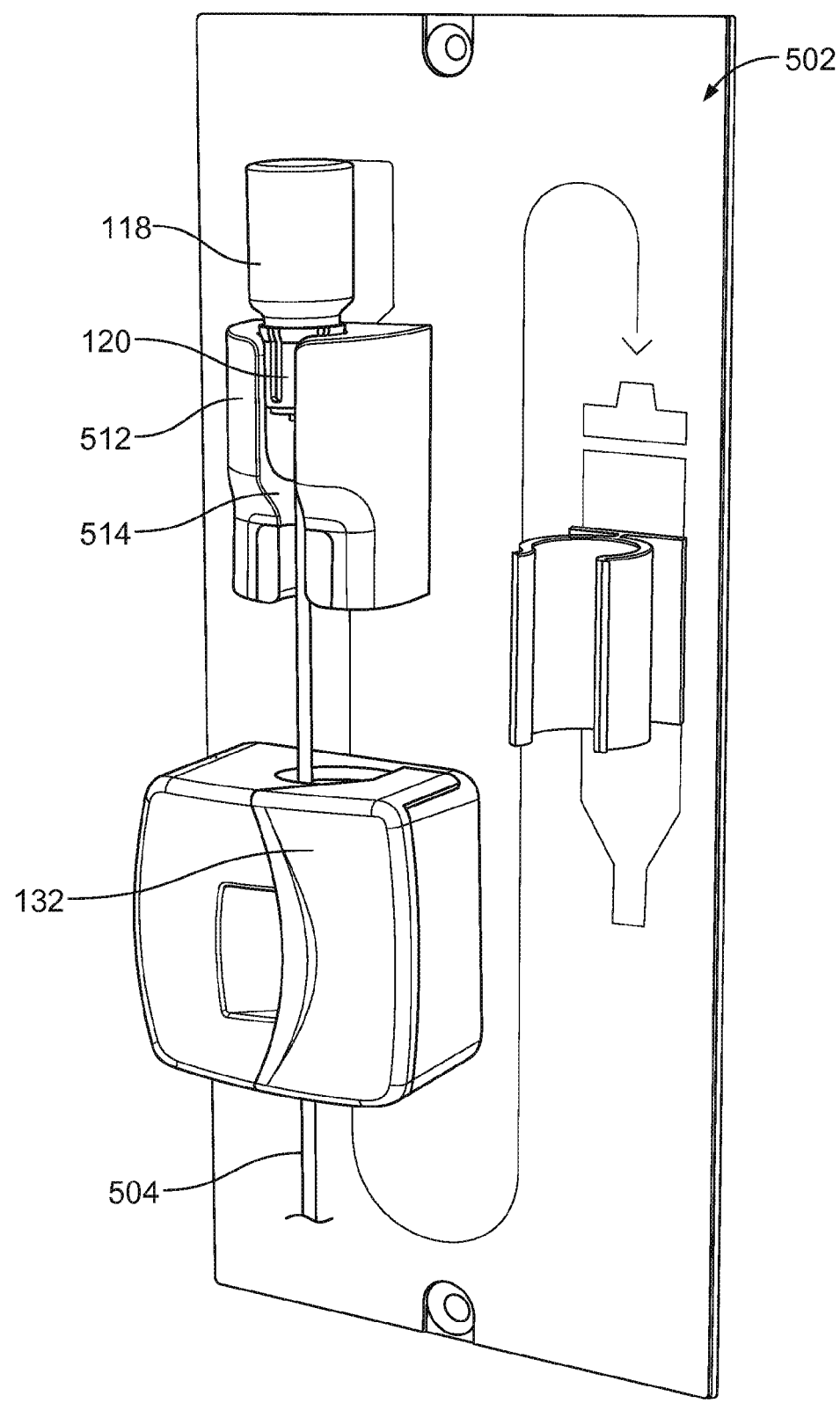
Figure 34:
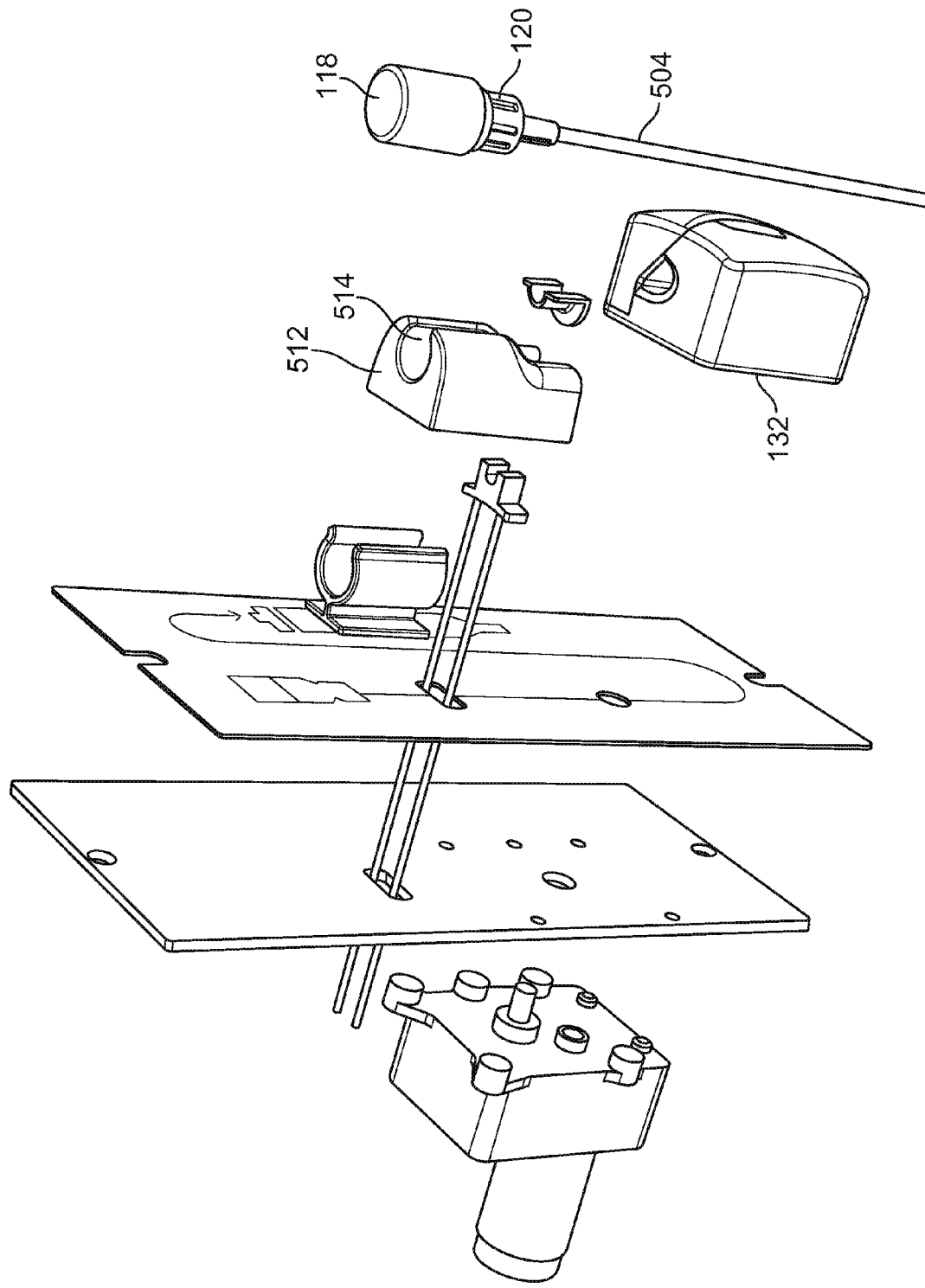
FIG. 34 is an exploded view of the modular drug delivery device of the hemodialysis machine of FIG. 31.

FIG. 31 illustrates a portion of a hemodialysis machine that includes a modular drug delivery device 502 configured to retain only a single vial. FIGS. 32 and 33 illustrate the drug delivery device 502 detached from the hemodialysis machine, and FIG. 34 illustrates an exploded view of the drug delivery device 502 and its associated drug administration fluid line set. The drug delivery device 502 is substantially the same as the drug delivery device 103 described above. However, the drug delivery device 502 illustrated in FIG. 31 includes a drug vial holder 512 that includes only one channel 514 instead of four. In addition, the drug administration fluid line set 107 that is used with the drug delivery device 520 includes a single drug delivery line 504 that is connected to the vial 118 via the drug vial spike 120. The drug delivery device 502 can be used where only one drug (e.g., Epogen®) is being administered to the patient and the prescribed dosage of that drug can be achieved with a single vial.

While the drip chamber 106 of the hemodialysis systems described above is illustrated as an arterial drip chamber (i.e., connected to the arterial patient line that draws blood into the dialysis machine from the patient), the drip chamber can alternatively be positioned as a venous drip chamber (i.e., connected to the venous patient line that returns blood from the dialysis machine to the patient). In certain implementations, the dialysis system includes both an arterial drip chamber and a venous drip chamber. In some implementations, the drug delivery line 104 of the drug administration fluid line set/cassette is connected to a venous drip chamber located between the dialyzer 110 and the patient.

While drug delivery devices have been described above as including their own control unit, the drug delivery device can alternatively or additionally be configured to communicate with a control unit of the hemodialysis machine. In certain implementations, for example, the various components of the dialysis machine, including the drug delivery device components, are controlled by a single control unit of the hemodialysis machine.

While certain drug delivery devices discussed above have been described as having user interfaces by which the operator can input information, such as prescribed drug dosages, those drug delivery devices can alternatively be provided with no user interface. In such implementations, for example, the drug delivery device can be in communication with a user interface of the hemodialysis machine (e.g., via a control unit of the drug delivery device or a control unit of the hemodialysis machine) such that the operator can use the user interface of the hemodialysis machine to input information, such as prescribed drug dosages, to the drug delivery device.

While the set up of the drug delivery device (e.g., the selection of the drug vials, the loading of the drug vials and the drug administration fluid line set, etc.) has been described as occurring after the hemodialysis treatment has begun, the set up of the drug delivery device can alternatively take place before the hemodialysis treatment begins.

While the methods of operating the drug delivery devices described above involve the user inputting a desired dosage prescription into the drug delivery device (e.g., typing the prescription into the touch screen of the drug delivery device), the prescription can alternatively be transmitted to the drug delivery device electronically. In certain implementations, for example, the desired prescription can be determined by a physician of the patient to be treated and the physician can input the prescription into a secured database or website. The prescription can then be automatically transmitted from the database to the control unit of the drug delivery device (e.g., to the control unit of the dialysis machine of which the drug delivery device is a part). This technique can help to prevent prescription input errors by the operator of the drug delivery device.

While the methods describe above including priming the feeder lines 122 by running the pump and sequentially opening and closing the occluders 128 or by sequentially running the pumps, in certain cases, other priming techniques can be used. In certain implementations, for example, a line connected at one end to a priming solution container is connected at its opposite end to the connector to which the drug delivery line 104 is connected during treatment, and the pump or pumps is/are operated in reverse. This draws the priming solution toward the vials. The pumps can be run in reverse until the priming solution reaches the tip of the spike and thus forces any air in the lines through the spike and into the vial or to atmosphere in the case that the vial has not yet been mounted on the spike.

While the methods described above involve delivering the Venofer® prior to the three vials of Epogen®, the drug vials can be emptied in different orders. In some implementations, for example, the Venofer® is delivered last. As a result, the delivery of the Venofer® through the various fluid lines and passages of the drug administration fluid line set/cassette can help to clear those lines and passages of any residual Epogen® remaining from the prior Epogen® deliveries. This technique can thus help to ensure that all of the Epogen® is delivered to the patient. By delivering the Venofer® last, it can also be assured that an air bubble can be fed through the various lines and passages of the drug administration fluid line set/cassette between delivery of the Venofer® and the Epogen® from the last Epogen® vial because the last Epogen® vial will be fully evacuated and thus allow air to be drawn from it. In contrast, the Venofer® vial is not always fully evacuated, so, when the Venofer® is delivered first, it may be more difficult to form the air bubble in the fluid lines and passages. For example, if the Venofer® vial is not fully evacuated, it may be necessary to remove the Venofer® vial from its spike to allow air to be drawn into the feeder line 122 associated with that spike.

While complete or substantially complete evacuation of the drug vial has been described as being achieved through the design of the drug vial spikes and/or the drug vial holders, complete evacuation of the drug from the vial can alternatively or additionally be accomplished using other techniques. In some implementations, for example, the vial is flushed with saline to help ensure complete evacuation of the drug vial. In certain implementations, pulse waves are delivered to the vial to shake loose any droplets adhered to the surface area of the vial and/or spike to help ensure complete evacuation of the vial. Liquid surface tension may cause droplets to adhere to the vial wall or the vial/seal junction. Mechanical or ultrasonic vibration tuned to a specific resonance based on the vial/spike combination may dislodge droplets and cause them to be evacuated from the vial. Agitation or mechanical tapping mechanisms can be employed to further break loose droplets. Alternatively or additionally, a non-toxic or inert surfactant could be applied to the inners surfaces of the vial and rubber seal to reduce surface tension and minimize droplet formation.

Figure 35:
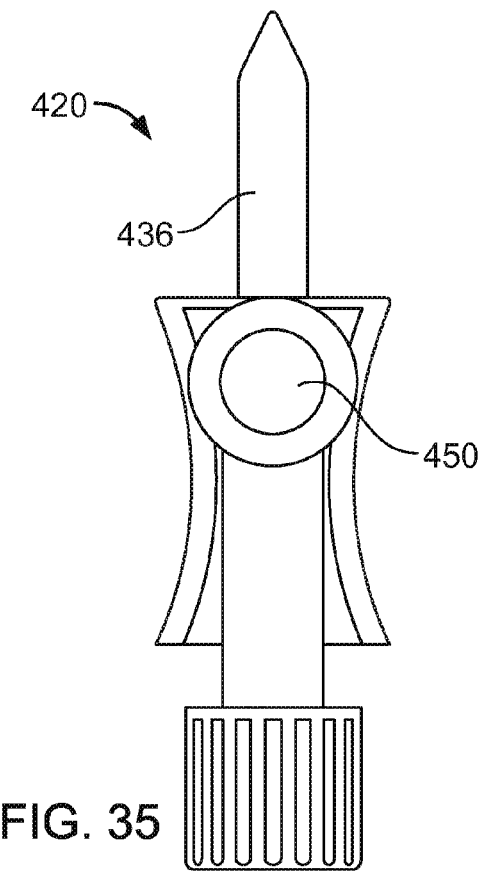
FIG. 35 illustrates a vented drug vial spike.

In some implementations, the drug vial spike can be vented. A drug vial spike 420 including a vented central spike 436 is shown in FIG. 35. The central spike 436 includes two channels extending therethrough. One of the channels extends from one end of the spike to the other to allow fluid to pass from the vial to a connected fluid line during use. The other channel is in fluid communication with the atmosphere and is equipped with a vent (e.g., a Gortex membrane) 450. The vent 450 is capable of allowing air to pass therethrough while preventing liquid from passing therethrough. As a result, when the drug vial spike 420 is being used such that the central spike 436 is disposed inside a drug vial, air can enter the vial via the vent 450 without allowing the drug to escape from the vial via the vent.

Figure 36:
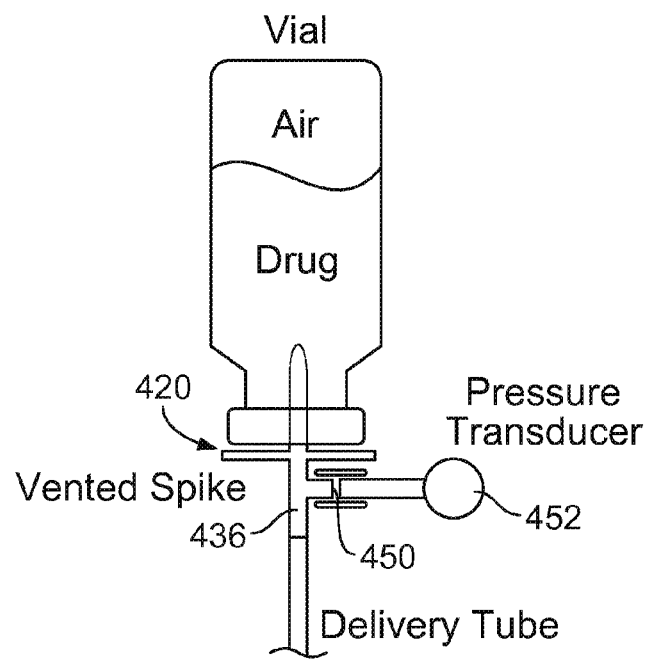
FIG. 36 is a schematic of the vented drug vial spike of FIG. 35 connected to a drug vial and a pressure transducer.

It is sometimes difficult to monitor the flow of the drug during direct vial delivery, e.g., to confirm delivery of the drug. Therefore, in certain implementations that utilize the above-described vented drug vial spike 420, drug delivery is determined by taking measurements of the air pressure in the vial. As shown in FIG. 36, a pressure transducer 452 is connected to the vent 450. As a result, air from the vial is able to pass across the vent 450 and contact the pressure transducer 452. Thus, the pressure transducer 452 is able to detect the air pressure within the vial. The air pressure is proportional to the fluid volume (or air volume) in the vial. Therefore, a detected change in air pressure indicates a change in air volume, and thus a change in the drug volume within the vial. As a result, measuring the fluid volume change in the vial allows for confirmation of delivery of the drug. In addition pressure in the vial, the temperature in the vial can be measured and conveyed to the control unit. This helps to ensure accurate volume calculations since pressure varies with temperature.

Figure 37:
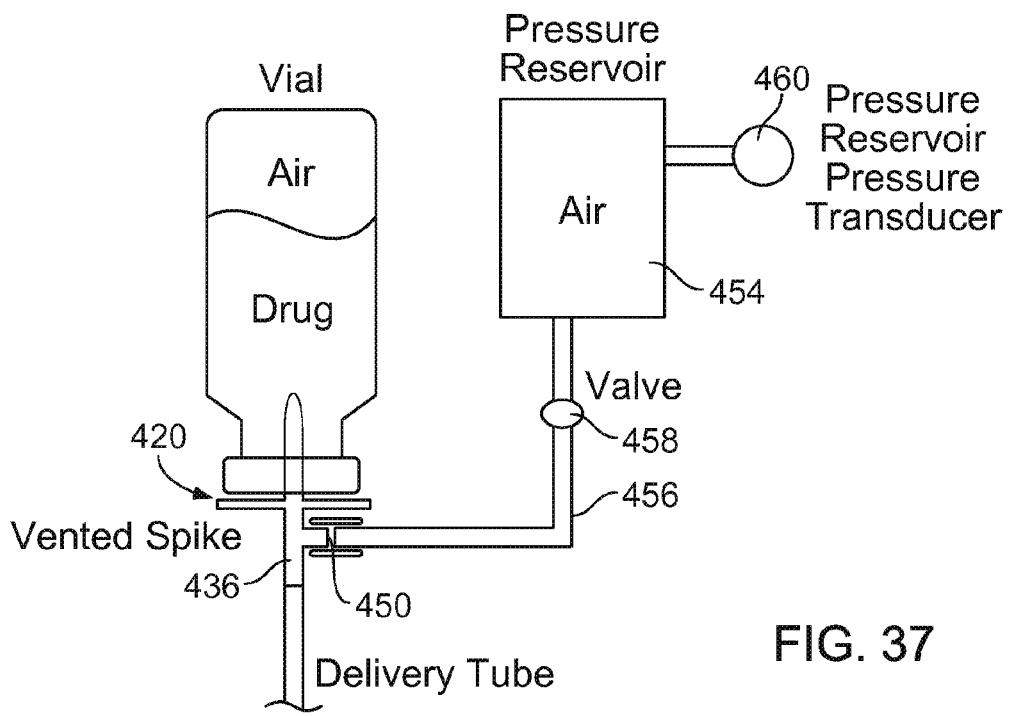
FIG. 37 is a schematic view of the vented drug vial spike of FIG. 35 connected to a drug vial and a pressure reservoir, which is connected to a pressure transducer.

In some implementations, drug delivery is provided for by forcing air into the vial via the second channel of the central spike 436, which forces the drug out of the vial via the first channel of the central spike 436 and into the patient line. Such an arrangement is illustrated in FIG. 37. As shown, a closed volume pressure reservoir 454 containing air is connected to the vent 450 via a fluid line 456. A valve 458 is positioned along the fluid line 456 to control the delivery of air to the vial, and thus control the rate at which the drug is forced out of the vial. A pressure transducer 460 is fluidly connected to the pressure reservoir 454. Drug delivery is determined by taking measurements of the air pressure in the pressure reservoir 454 using the pressure transducer 460. For example, measuring a drop in air pressure within the pressure reservoir 454 can indicate that the air volume within the vial is increasing and, therefore, that the drug volume within the vial is decreasing. It is therefore possible to conclude from a drop in pressure at the pressure transducer 460 that drug is being delivered from the vial.

While the drug vials 116, 118 have been described as including rubber seals, the seals can alternatively or additionally be formed of other resilient materials that are capable of being pierced by the drug vial spikes described herein. Examples of some such materials include silicon, rubber, and butyl rubber.

While the seals 123 of the vials 116, 118 have been described as being held between the cap 119 and the neck portion 121 of the vial 116, 118, vials of other configurations can be used. In certain implementations, for example, vials that do not include neck portions are used. Those vials include a body portion of substantial uniform diameter along its length and a seal held between the body portion and a cap of the vial.

While the drug vials have been described as being used in the drug delivery systems and methods described above, in certain implementations, other types of drug containers, such as bags, bottles, etc., are used.

While the drug delivery devices above have been described as being used to deliver Venofer® and/or Epogen®, it should be understood that the term "drug" as used herein incorporates pharmaceuticals as well as other fluids delivered to a patient intravenously. Other drugs that are contemplated to be automatically delivered to the patient in accordance with the various implementations of the invention, include but are not limited to, phosphate binders, vitamin D, and anticoagulants.

Other implementations are within the scope of the following claims.

What is claimed is:

1. A drug vial spiking device, comprising:
   a cup-shaped member having a base and a sidewall, the base and the sidewall at least partially forming a recess configured to receive at least a portion of a drug vial;
   a spike extending from a central region of the base, the spike defining a channel extending therethrough; and
   a plurality of springs extending from the base of the cup-shaped member into the recess, the springs configured to apply a force to the drug vial in a direction away from the base of the cup-shaped member when at least a portion of the drug vial is positioned in the recess such that a seal of the drug vial bulges away from the drug vial and forms a concave shape.

2. The drug vial spiking device of claim 1, wherein the springs are leaf springs.

3. The drug vial spiking device of claim 2, wherein at least one of the leaf springs comprises a projection extending from a surface thereof, the projection being arranged to contact a cap of the drug vial when the drug vial is inserted into the recess.

4. The drug vial spiking device of claim 3, wherein the projection and the at least one leaf spring are configured in a manner such that the projection dents a cap of the drug vial when the drug vial is inserted into the recess.

5. The drug vial spiking device of claim 1, wherein the base defines a plurality of openings configured to receive the plurality of springs when the drug vial is fully inserted into the recess.

6. The drug vial spiking device of claim 1, wherein at least one of the springs comprises a projection extending therefrom, the at least one of the springs and the projection being configured such that the projection dents a cap of the drug vial when the drug vial is inserted into the recess with sufficient force to cause the cap of the vial to contact the base of the cup-shaped member.

7. The drug vial spiking device of claim 1, further comprising at least one bi-stable member attached to the base, the bi-stable member positioned above an aperture defined in the base.

8. The drug vial spiking device of claim 7, wherein the bi-stable member is configured to be stably positioned in a first position and a second position, and at least a portion of the bi-stable member is visible to a user when the bi-stable member is in the second position.

9. The drug vial spiking device of claim 8, wherein the bi-stable member in the second position indicates that a drug vial has been fully inserted into the recess.

10. The drug vial spiking device of claim 8, wherein the portion of the member visible to the user protrudes from an outer surface of the base.

11. The drug vial spiking device of claim 8, wherein the bi-stable member comprises a projection extending from its upper surface.

12. The drug vial spiking device of claim 11, wherein the projection is configured to push the bi-stable member from the first position to the second position when the drug vial is fully inserted into the recess such that the vial contacts the base of the cup-shaped member.

13. The drug vial spiking device of claim 1, wherein the spike comprises a portion configured to engage an inner surface of a seal of a drug vial after the spike is inserted into the drug vial.

14. The drug vial spiking device of claim 13, wherein the portion of the spike extends laterally in at least one direction to a greater extent than a remainder of the spike.

15. The drug vial spiking device of claim 14, wherein the portion of the spike is substantially conical.

16. The drug vial spiking device of claim 14, wherein the portion of the spike comprises a barb.

17. The drug vial spiking device of claim 1, wherein the spike defines a plurality of openings along an outer surface of the spike, and each of the openings is in fluid communication with the channel.

18. The drug vial spiking device of claim 1, wherein a portion of the sidewall forms a flange that retains the portion of the vial within the recess.

19. The drug vial spiking device of claim 18, wherein the flange is configured to contact a cap of the vial.

20. A fluid line set, comprising:
a plurality of fluid lines;
a plurality of drug vial spiking devices, each of the drug vial spiking devices being connected to one of the fluid lines, and each of the drug vial spiking devices comprising
a cup-shaped member having a base and a sidewall, the base and the sidewall at least partially forming a recess configured to receive at least a portion of a drug vial;
a spike extending from a central region of the base, the spike defining a channel extending therethrough; and
a plurality of springs extending from the base of the cup-shaped member into the recess, the springs configured to apply a force to the drug vial in a direction away from the base of the cup-shaped member when at least a portion of the drug vial is positioned in the recess such that a seal of the drug vial bulges away from the drug vial and forms a concave shape.

* * * * *